(12) United States Patent
Chatterjee et al.

(10) Patent No.: US 10,669,306 B2
(45) Date of Patent: Jun. 2, 2020

(54) SOLID SUPPORTS FOR USE IN SOLID-PHASE PEPTIDE SYNTHESIS, KITS, AND RELATED METHODS

(71) Applicant: UNIVERSITY OF WASHINGTON, Seattle, WA (US)

(72) Inventors: Champak Chatterjee, Seattle, WA (US); Patrick M. Shelton, Seattle, WA (US); Caroline E. Weller, Seattle, WA (US)

(73) Assignee: University of Washington, Seattle, WA (US)

(*) Notice: Subject to any disclaimer, the term of this patent is extended or adjusted under 35 U.S.C. 154(b) by 151 days.

(21) Appl. No.: 16/067,727

(22) PCT Filed: Feb. 3, 2017

(86) PCT No.: PCT/US2017/016455
§ 371 (c)(1),
(2) Date: Jul. 2, 2018

(87) PCT Pub. No.: WO2017/136690
PCT Pub. Date: Aug. 10, 2017

(65) Prior Publication Data
US 2019/0010186 A1    Jan. 10, 2019

Related U.S. Application Data

(60) Provisional application No. 62/291,061, filed on Feb. 4, 2016.

(51) Int. Cl.
*C07K 1/00* (2006.01)
*C07K 1/02* (2006.01)
(Continued)

(52) U.S. Cl.
CPC ............ *C07K 1/026* (2013.01); *C07C 323/10* (2013.01); *C07K 1/042* (2013.01); *C07K 1/107* (2013.01); *C07K 17/08* (2013.01); *C40B 50/18* (2013.01)

(58) Field of Classification Search
CPC ...... C07K 1/042; C07K 17/08; C07C 323/10; C40B 50/18
See application file for complete search history.

(56) References Cited

U.S. PATENT DOCUMENTS

| | | | |
|---|---|---|---|
| 6,448,058 B1* | 9/2002 | Patel | C12N 9/18 435/197 |
| 7,718,598 B1* | 5/2010 | Smythe | C07K 1/04 514/1.1 |

(Continued)

OTHER PUBLICATIONS

International Search Report and Written Opinion dated Apr. 12, 2017 for Application No. PCT/US201716455.
(Continued)

*Primary Examiner* — Robert C Boyle
(74) *Attorney, Agent, or Firm* — Christensen O'Connor Johnson Kindness PLLC

(57) ABSTRACT

Solid supports for use in solid-phase peptide synthesis (SPPS) are provided. The solid supports may include a resin and a protected linker coupled to the resin. The linker may be an N-mercaptoethoxyglycine, an N-mercaptopropoxyglycine, an N-mercaptobutoxyglycine, and/or another suitable linker. Kits for use in SPPS are also provided. The kits may include a solid support, a solution including a thiol or a selenol, one or more pluralities of protected amino acids, and/or a wash buffer. Methods of SPPS are also provided. The methods may include providing a solid support including a resin coupled to a protected linker.

20 Claims, 52 Drawing Sheets
Specification includes a Sequence Listing.

(51) Int. Cl.
   C07K 1/04     (2006.01)
   C40B 50/18    (2006.01)
   C07C 323/10   (2006.01)
   C07K 1/107    (2006.01)
   C07K 17/08    (2006.01)

(56) References Cited

U.S. PATENT DOCUMENTS

| | | | |
|---|---|---|---|
| 8,058,394 B2 | 11/2011 | Kajihara et al. | |
| 2005/0164339 A1* | 7/2005 | van der Donk | C12N 9/52 435/68.1 |
| 2011/0184148 A1 | 7/2011 | Hojo et al. | |
| 2012/0149868 A1* | 6/2012 | Kornbeck | C07K 1/16 530/308 |
| 2016/0002286 A1 | 1/2016 | Brik et al. | |

OTHER PUBLICATIONS

Botti, et al.,Native Chemical Ligation Through in Situ O to S Acyl Shift. Org. Lett. 2004; 6: 4861-4864; DOI:10.1021/ol10481028.

Canne, et al.,Extending the Applicability of Native Chemical Ligation, J. Am. Chem. Soc. 1996; 118: 5891-5896; DOI:10.1021/ja960398s.

Crich, et al.,Solid-Phase Synthesis of Peptidyl Thioacids Employing a 9-Fluorenylmethyl Thioester-Based Linker in Conjunction with Boc Chemistry, Journal of Organic Chemistry vol. 74 Issue 19 pp. 7383-7388, published 2009.

Dawson, et al.,Synthesis of Protein by Native Chemical Ligation, Science. 1994; 266: 776-779.

Evans, et al.,Semisynthesis of Cytotoxic Proteins Using a Modified Protein Splicing Element, Protein Sci. 1998; 7: 2256-2264; DOI:10.1002/pr0.5570071103.

Hackeng, et al.,Protein Syntheses by Native Chemical Ligation: Expanded Scope by Using Straightforward Methodology, Proc. Natl. Acad. Sci. U.S.A. 1999; 96: 10068-10073; DOI:10.1073/pnas.96.18.10068.

Haubner, et al.,Structural and Functional Aspects of RGD-Containing Cyclic Pentapeptides as Highly Potent and Selective Integrin aVB3 Antagonists, J. Am. Chem. Soc. 1996; 118: 7461-7472; DOI:10.1021/ja9603721.

Hou, et al.,Peptidly N, N-Bis (2-Mercaptoethyl)-Amides and Thioester Precursors for Native Chemical Ligation, Org. Lett. 2011; 13: 386-389.

Lee, et al.,A One-Pot Approach to Neoglycopeptides Using Orthogonal Native Chemical Ligation and Click Chemistry, Org. Lett. 2009; 11: 5270-5273; DOI:10.1021/ol902131n.

Ling, et al.,Protein Thioester Synthesis Enabled by Sortase, J. Am. Chem. Soc. 2012; 134: 10749-10752; DOI:10.1021/0302354v.

Liu, et al.,An FMOC Compatible, O to S Shift-Mediated Procedure for the Preparation of C-Terminal Thioester Peptides, J. Org. Chem. 2013; 78: 9848-9856; DOI:10.1021/jo4015112.

Ludwig, et al.,Ligation of a Synthetic Peptide to the N Terminus of a Recombinant Protein Using Semisynthetic Protein Trans-Splicing, Angew. Chemic—Int. Ed. 2006; 45: 5218-5221: DOI:10.1002/anie.200600570.

MacMillan, et al.,Shifting Native Chemical Ligation into Reverse Through N—S Acyl Transfer, Israel Journal of Chemistry, 2011, 51 (8-9): 885-899.

Malins, et al.,Recent Extensions to Native Chemical Ligation for the Chemical Synthesis of Peptides and Proteins, Current Opinion in Chemical Biology, 2014, 22:70-78.

Ollivier, et al.,Bis (2-Solfanylethyl) Amino Native Peptide Ligation, Org. Left. 2010; 12: 5238-5241; DOI:10.1021/ol102273u.

Sato, et al.,N-Sulfanylethylanilide Peptide as a Crypto-Thioester Peptide, ChemBioChem 2011; 12: 1840-1844.

Schnolzer, et al.,In Situ Netralization in Boc-Chemistry Solid Phase Peptide Synthesis, Int. J. Pept. Res. Ther. 2007; 13: 31-44; DOI:10.1007/s10989-006-9059-7.

Shao, et al.,A Novel Method to Synthesize Cyclic Peptides, Tetrahedron Lett. 1971; 39: 1-2.

Sharma, et al., Direct FMOC-Chemistry-Based Solid Phase Synthesis of Peptidyl Thioesters, Journal of Organic Chemistry vol. 76 Issue 16 pp. 6518-6524, published 2011.

Sharma, et al.,Tandem Thiol Switch Synthesis of Peptide Thioesters via N—S Acyl Shift on Thiazolidine, Org. Lett. 2011; 13: 5176-5179; DOI:10.1021/ol202147q.

Tan, et al.,An Enzymatic Approach to the Synthesis of Peptide Thioesters: Mechanism and Scope, ChemBioChem 2007; 8: 1512-1515; DOI:10.1002/cbic.200700284.

Thongyoo, et al.,Chemical and Biomimetic Total Syntheses of Natural and Engineered MCoTI Cyclotides, Org. Biomol. Chem. 2008; 6: 1462-1470; DOI:10.1039/b810667d.

Tulla-Puche, et al.,On-Resin Native Chemical Ligation for Cyclic Peptide Synthesis, J. Org. Chem. 2004; 69: 4101-4107: DOI:10.1021/jo049839d.

Wang, et al.,Peptide O-Aminoanilides as Crypto-Thioesters for Protein Chemical Synthesis, Chemie Int. Ed. 2015; 54: 2194-2198; DOI:10.1002/anie.201408078.

Wang, et al.,Theoretical Analysis of the Detailed Mechanism of Native Chemical Ligation Reactions, Chem. Asian J. 2011; 6: 1241-1251; DOI:10.1002/asia.201000760.

Yan, et al.,Synthesis of Peptides and Proteins without Cysteine Residues by Native Chemical Ligation Combined with Desulfurization, J. Am. Chem. Soc. 2001; 123: 526-533; DOI:10.1021/ja003265m.

Zheng, et al.,A New Method for Synthesis of Peptide Thioestiers via Irriversible N-to-S Acyl Transfer, Org. Lett. 2014; 16: 4908-4911; DOI:10.1021/ol5024213.

Zheng, et al.,FMOC Synthesis of Peptide Thioesters Without Post-Chain-Assembly Manipulation, Journal of the American Chemical Society, vol. 133 Issue 29 pp. 11080-11083, published 2011.

* cited by examiner

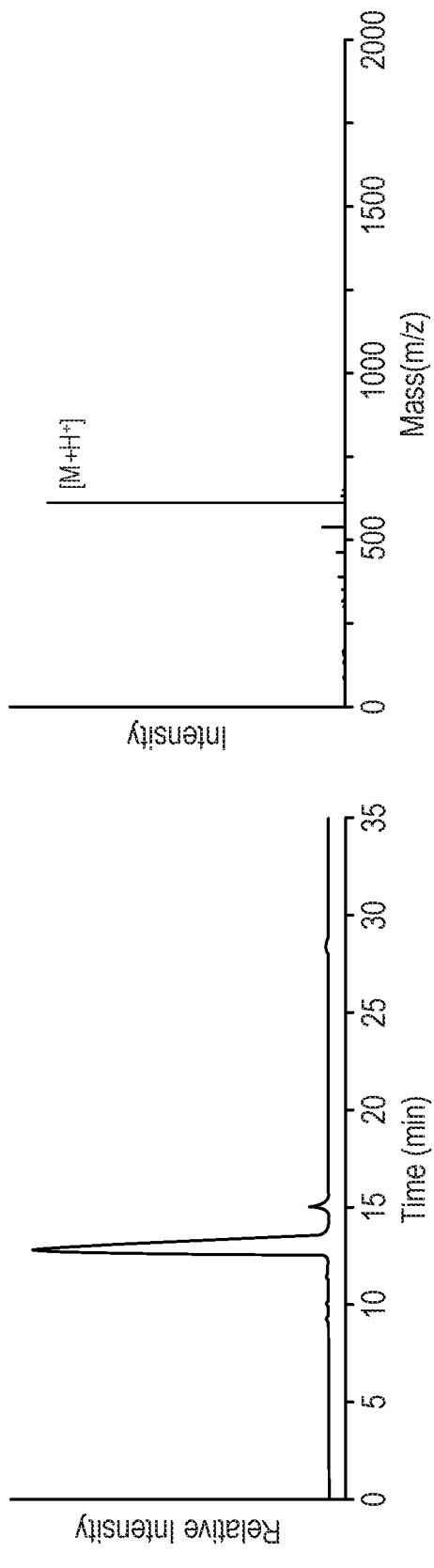
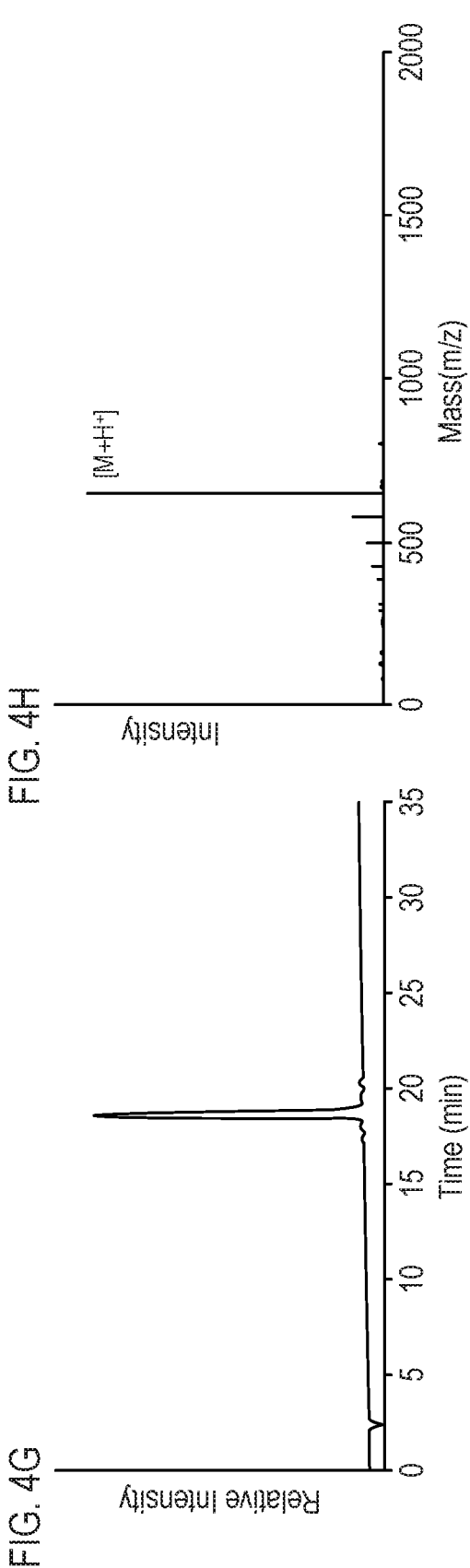

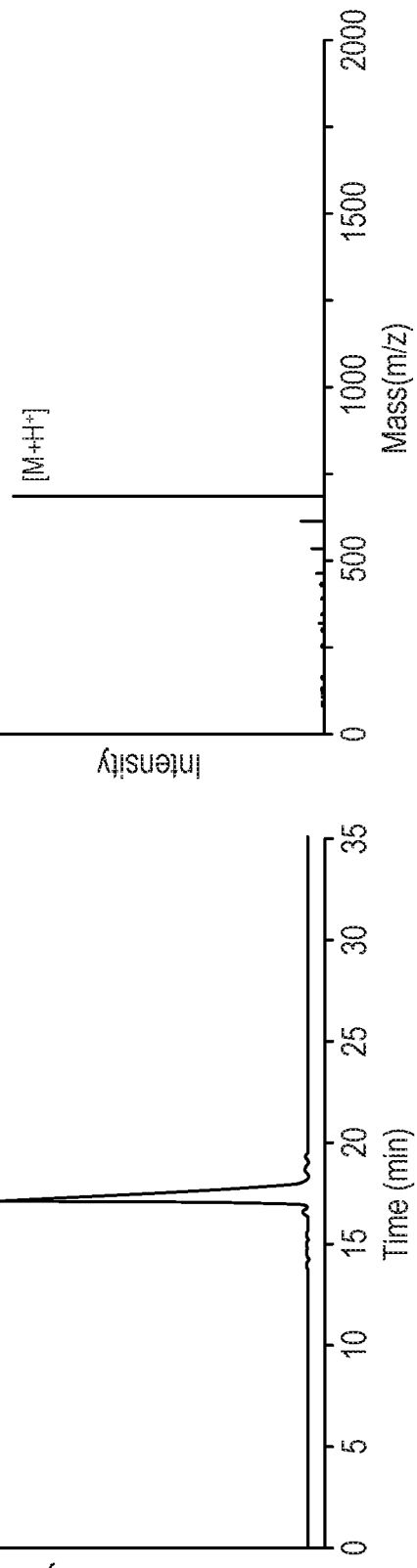
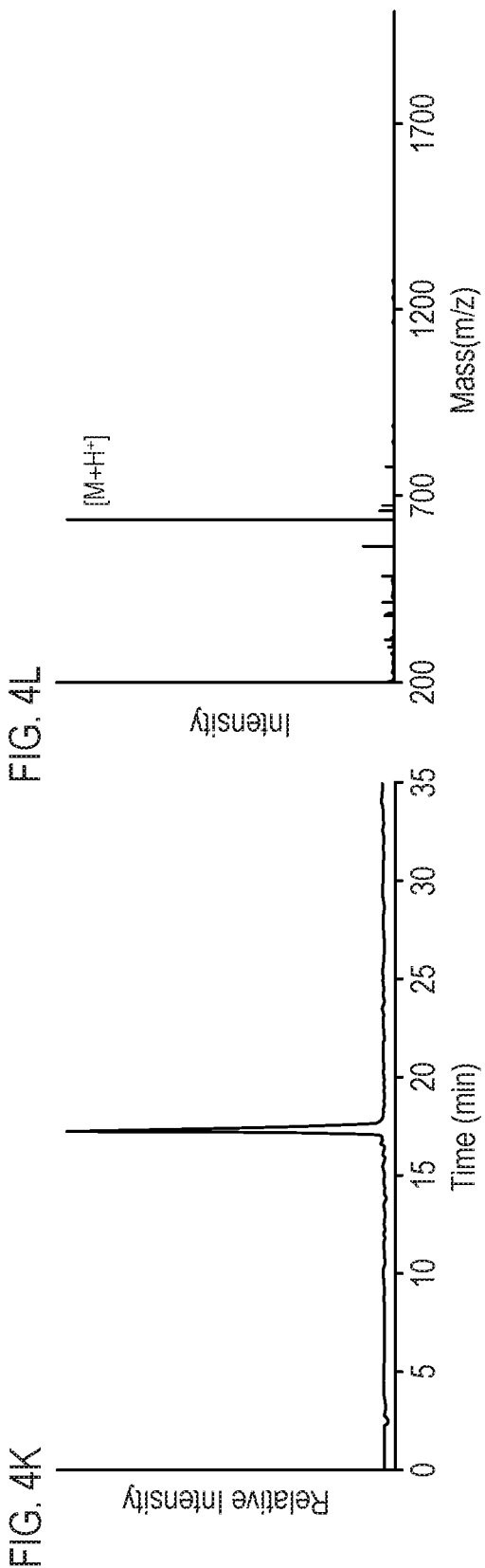
FIG. 4I  FIG. 4J  FIG. 4K  FIG. 4L

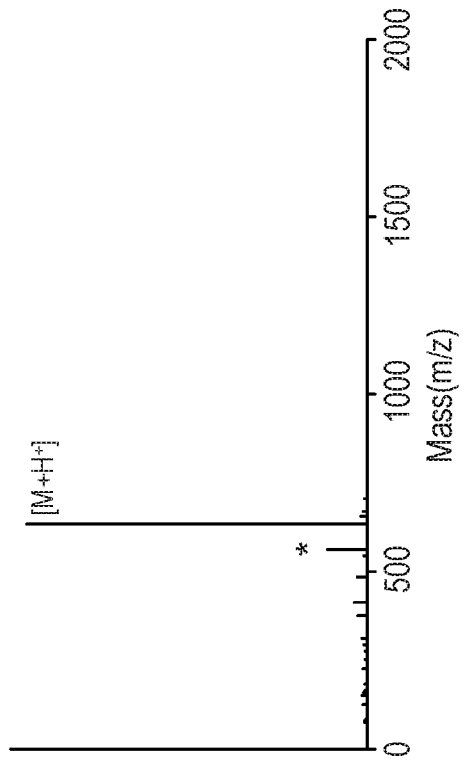
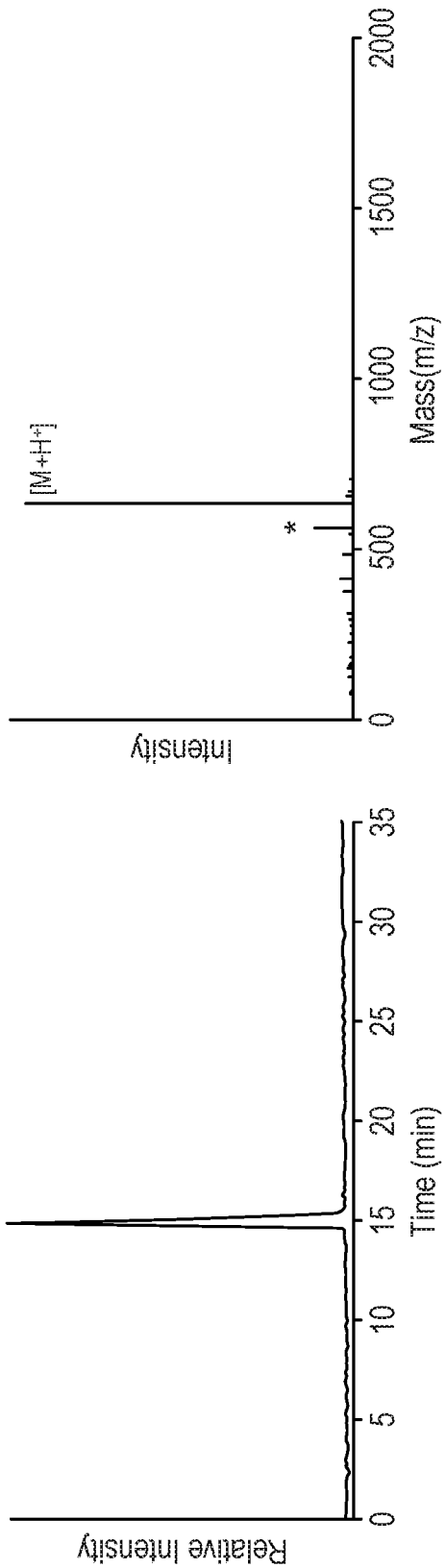
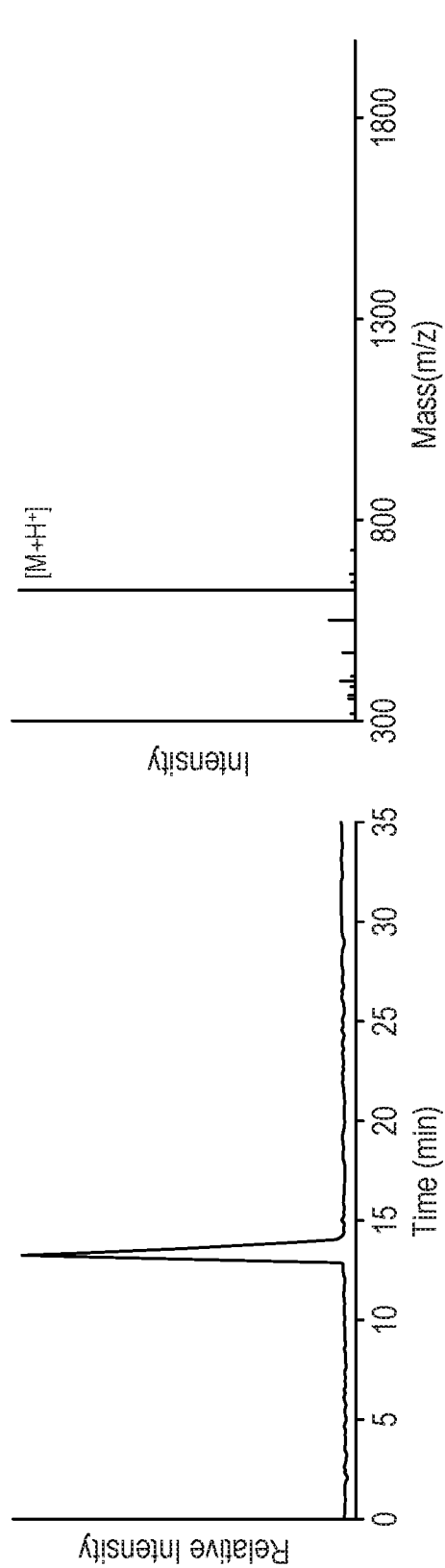

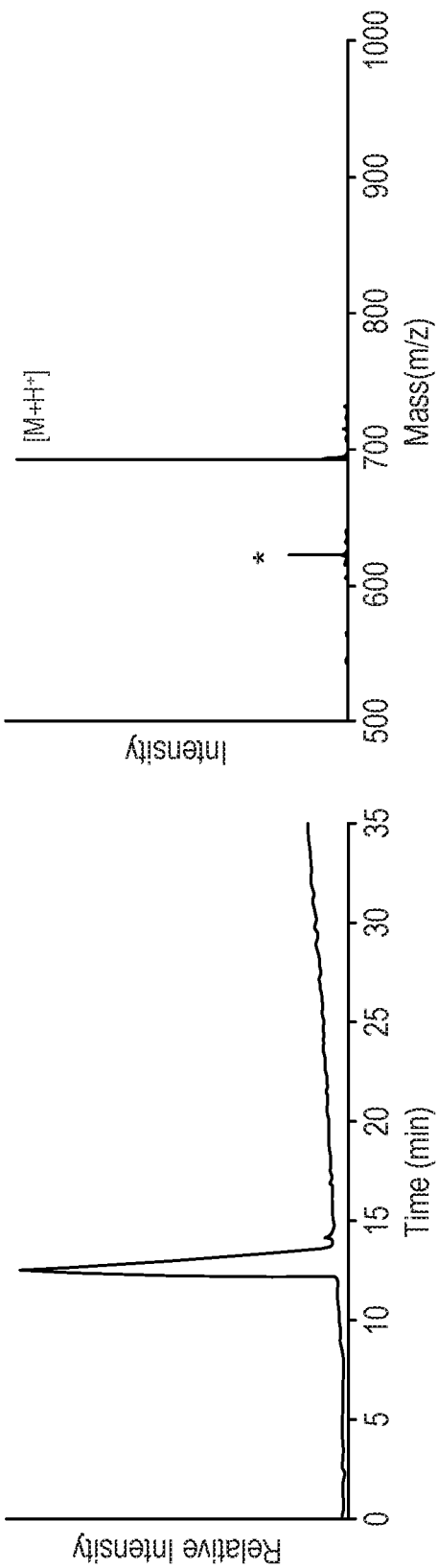
FIG. 4Q
FIG. 4R
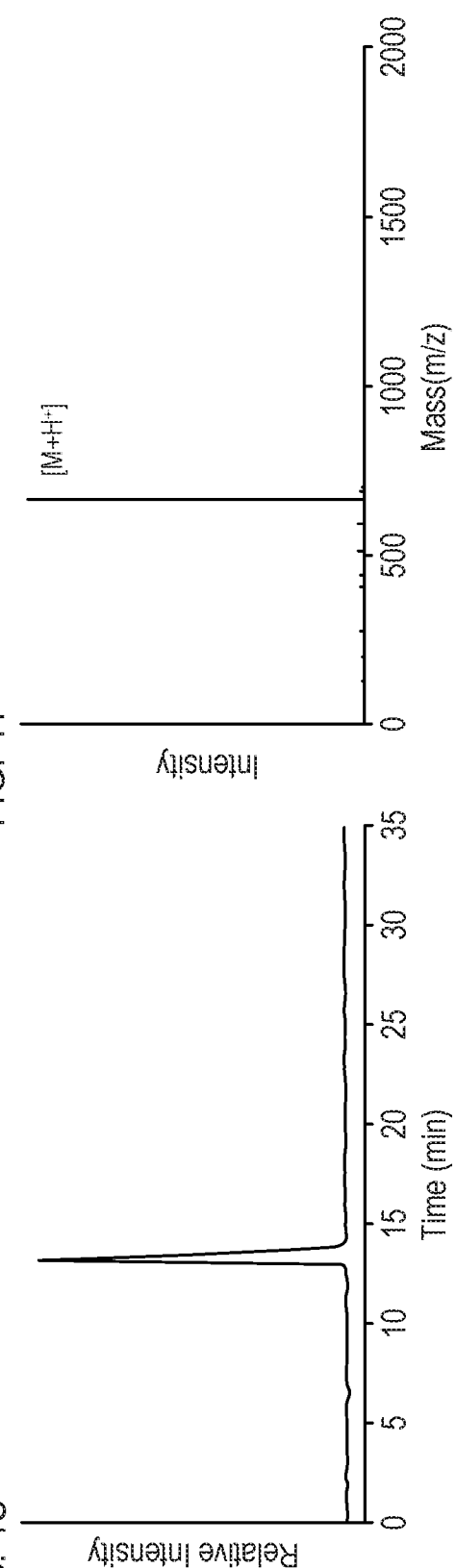
FIG. 4S
FIG. 4T

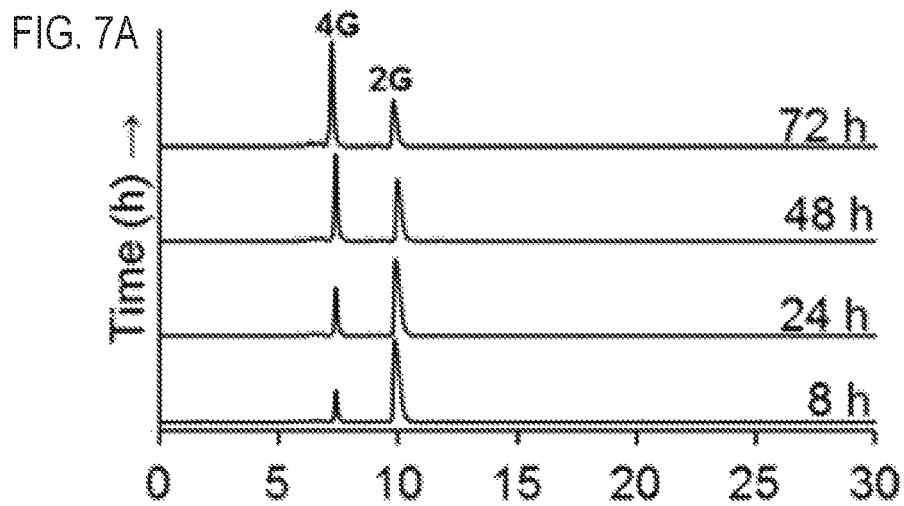
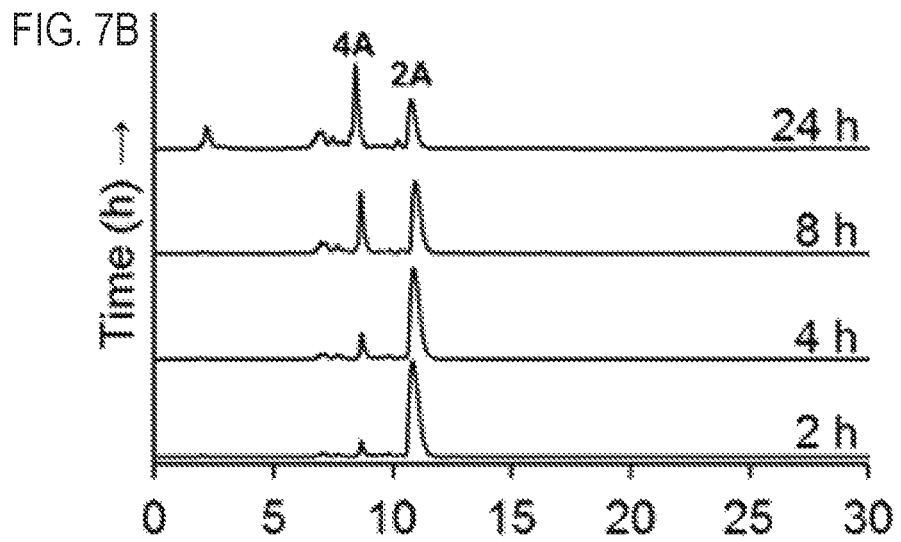
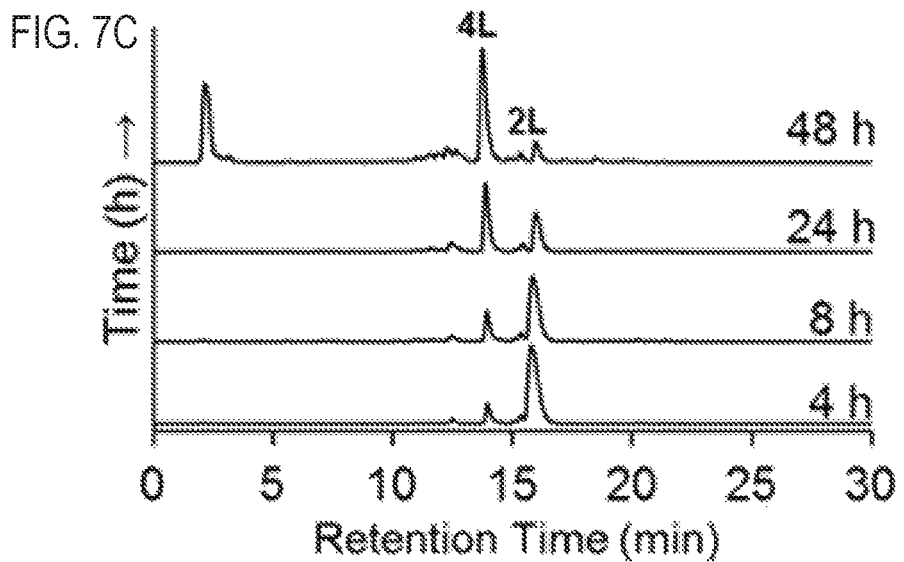

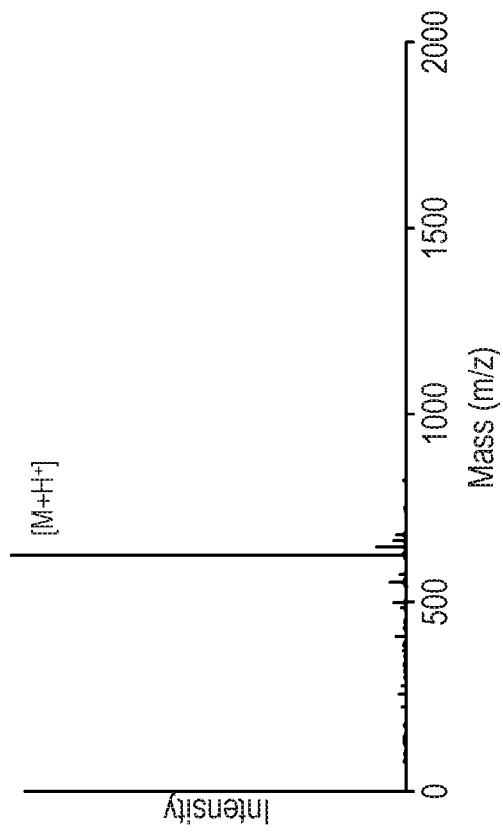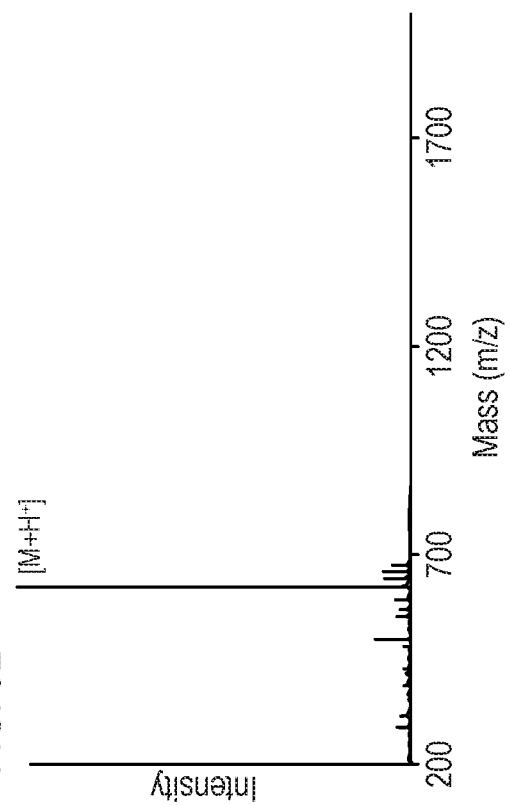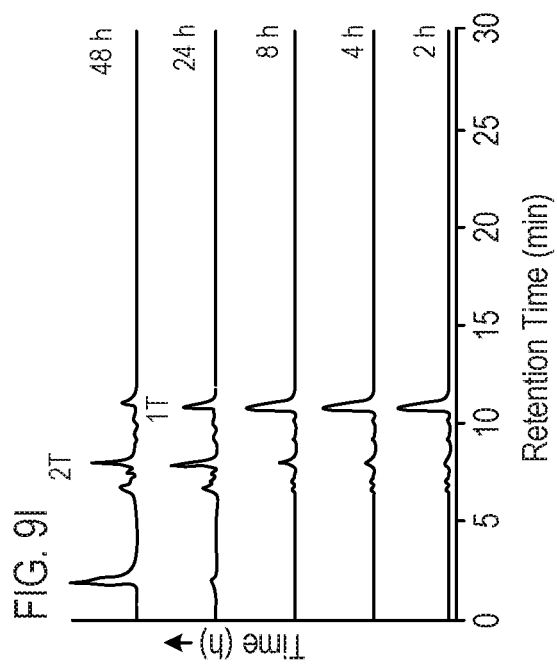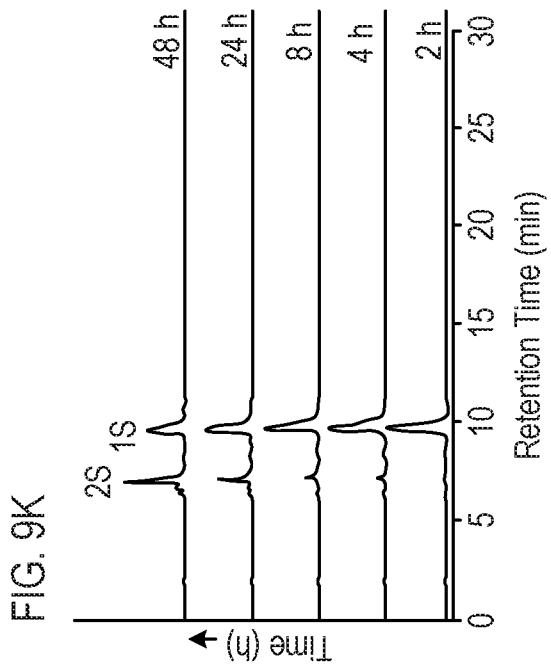

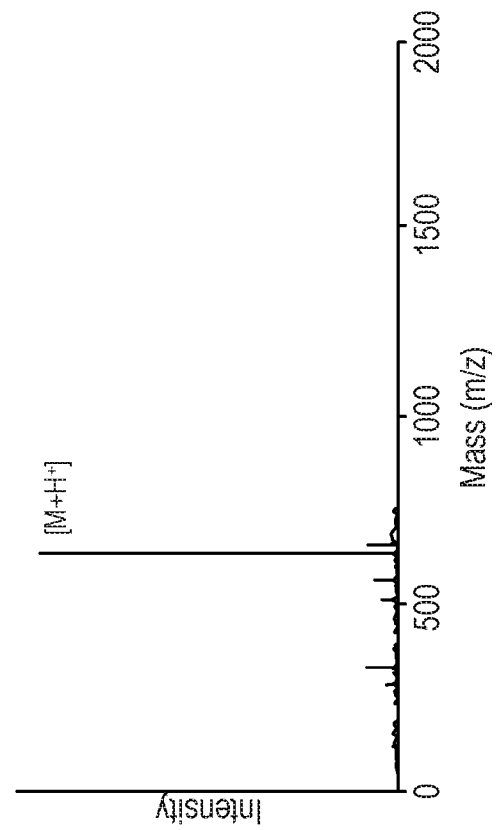
FIG. 9U
FIG. 9V
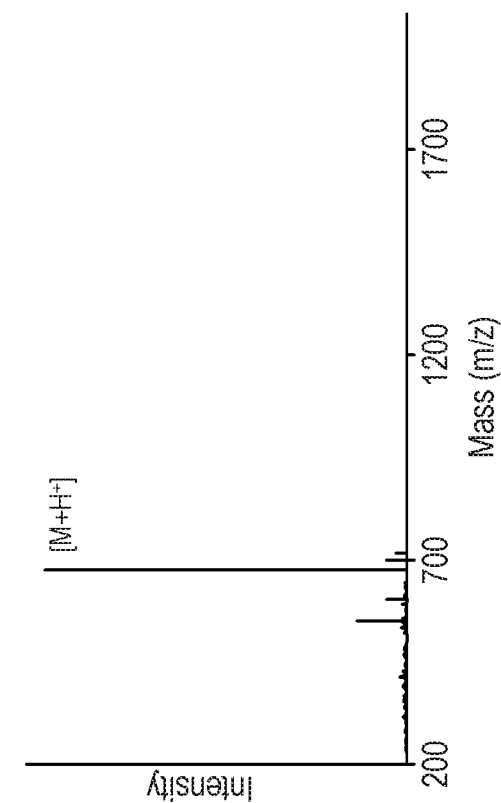
FIG. 9W
FIG. 9X

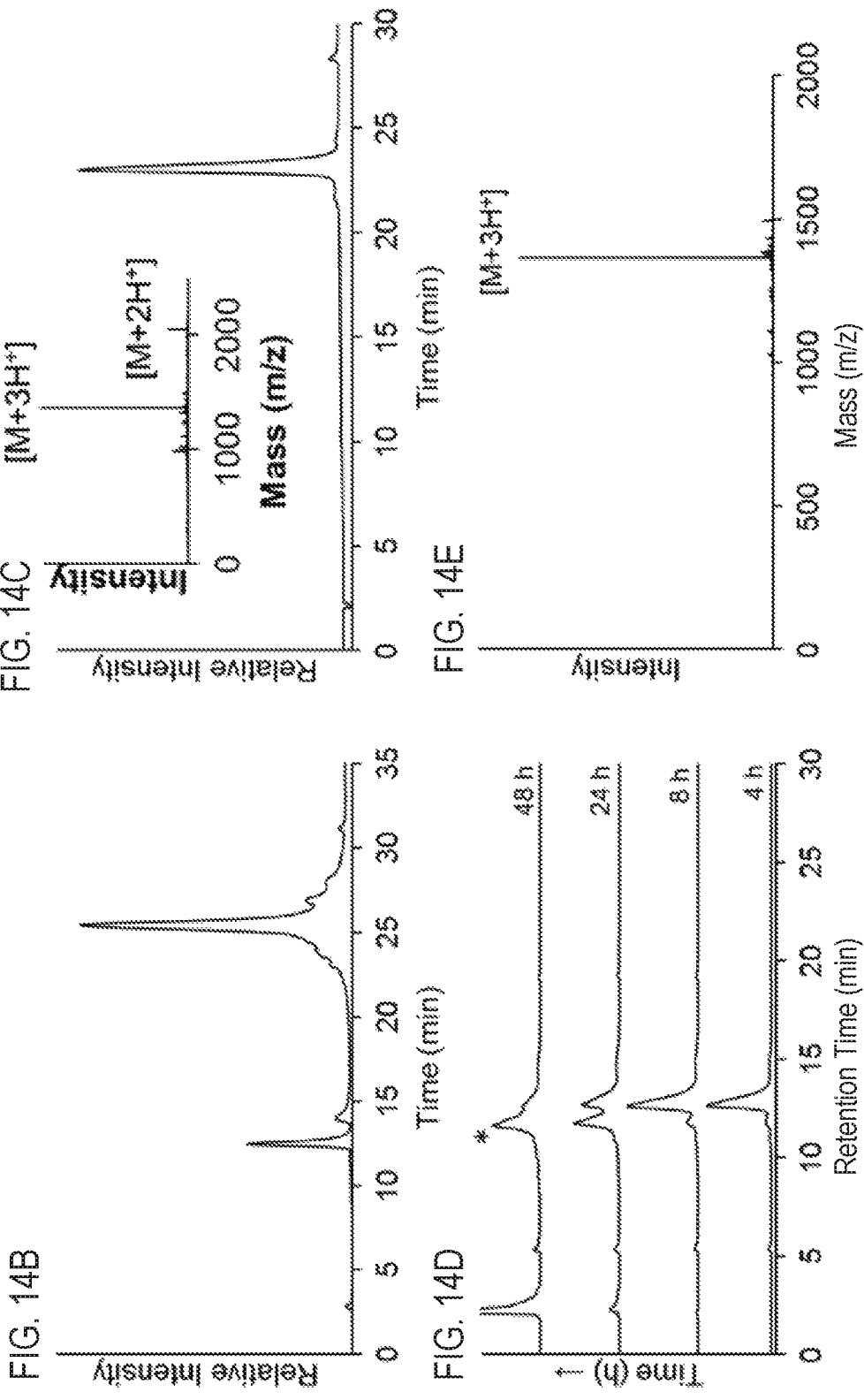
FIG. 14A  H2N — MEEPQSDPSVEPPLSQETFSDLWKLLPENNVLSPL — MEGA  (SEQ ID NO:21)

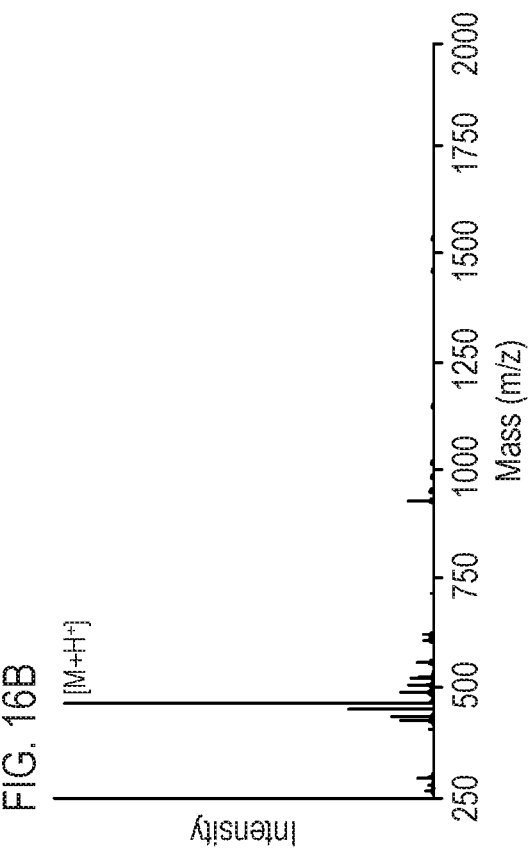
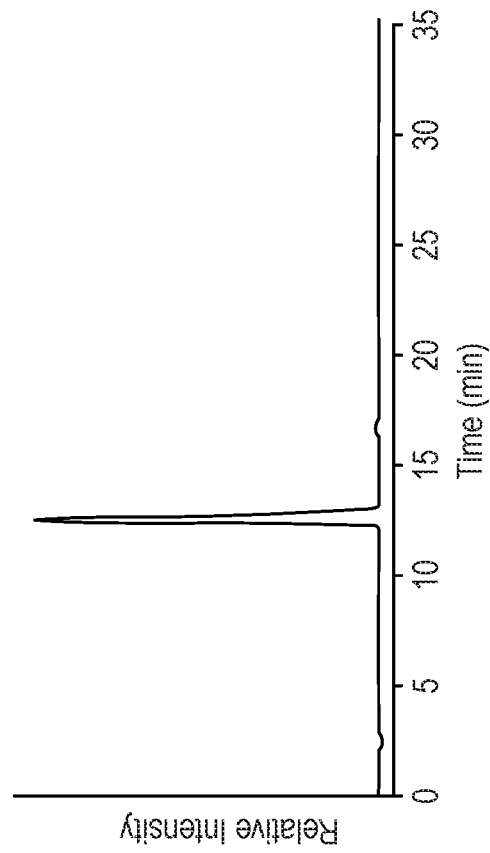
FIG. 16B
FIG. 16A

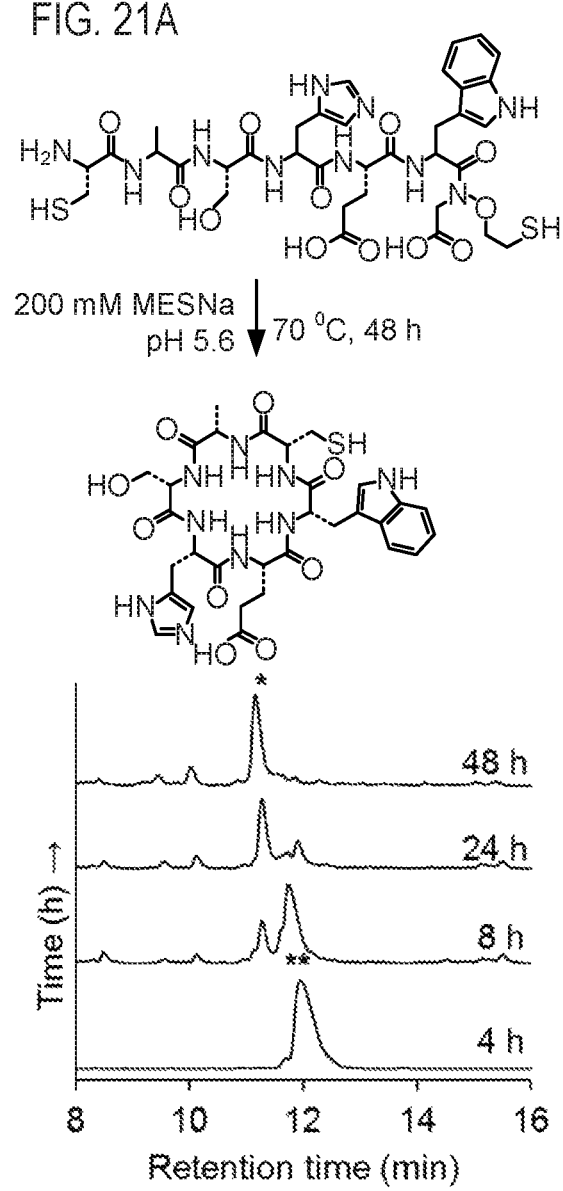
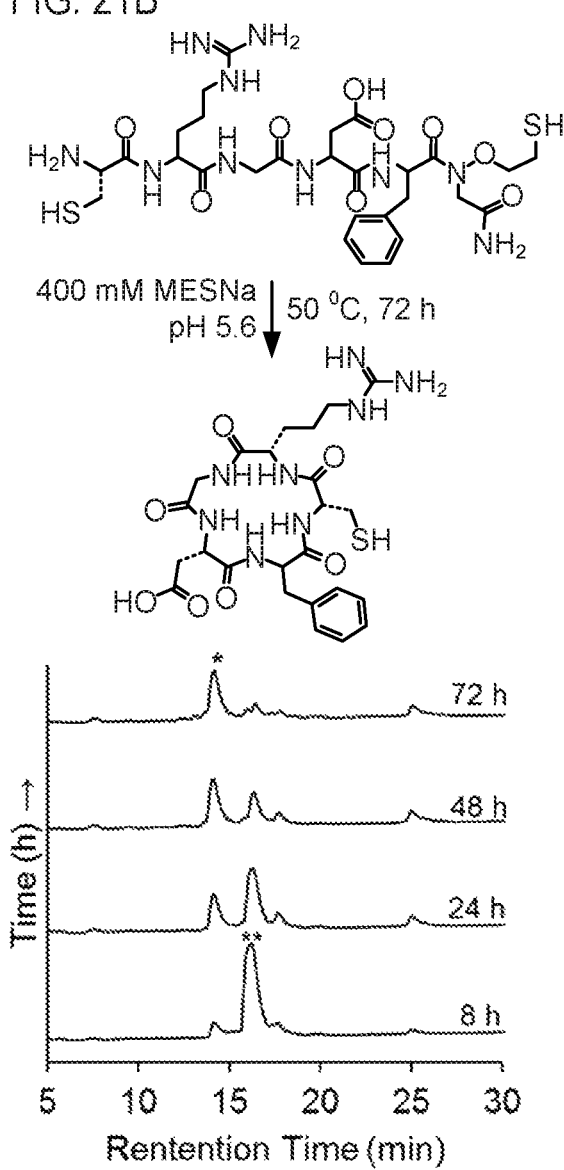

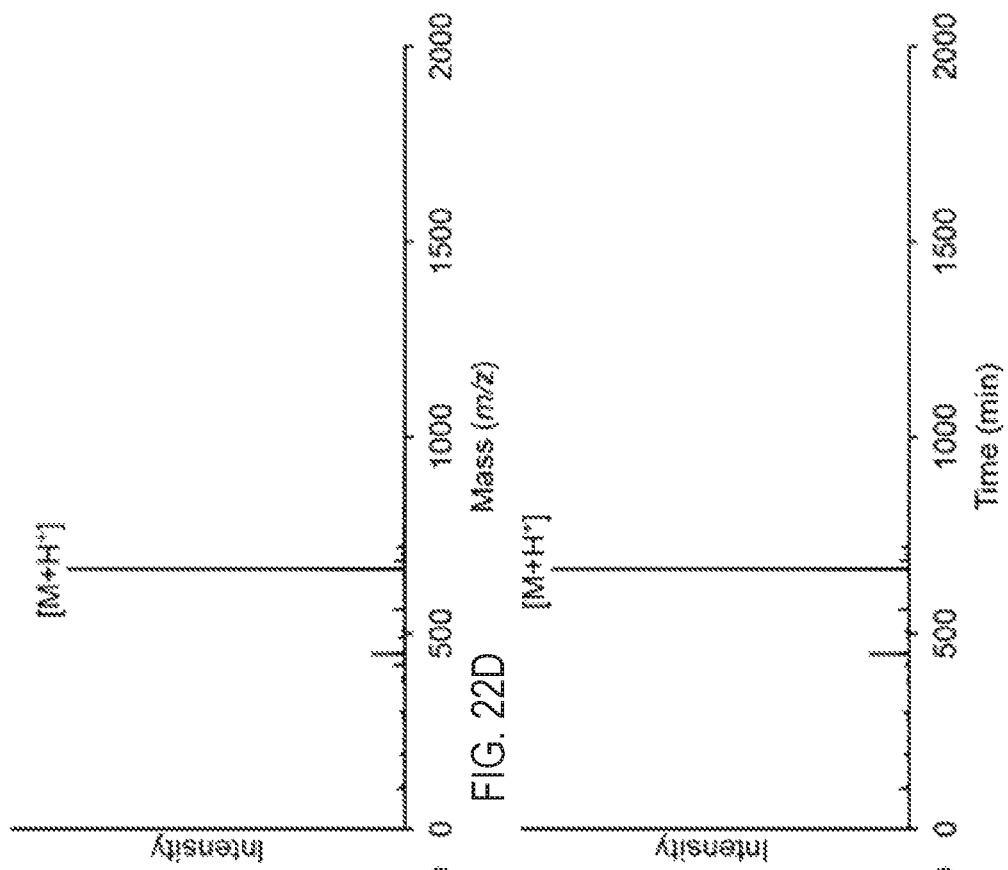
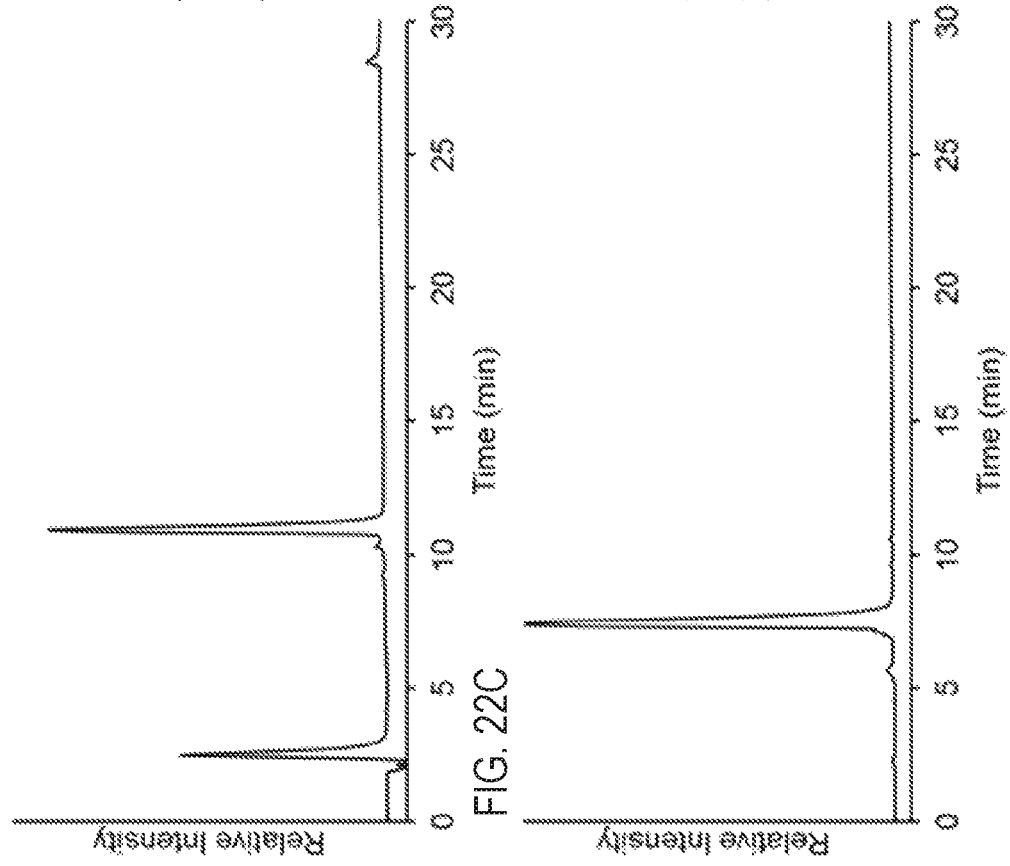
FIG. 22A
FIG. 22B
FIG. 22C
FIG. 22D

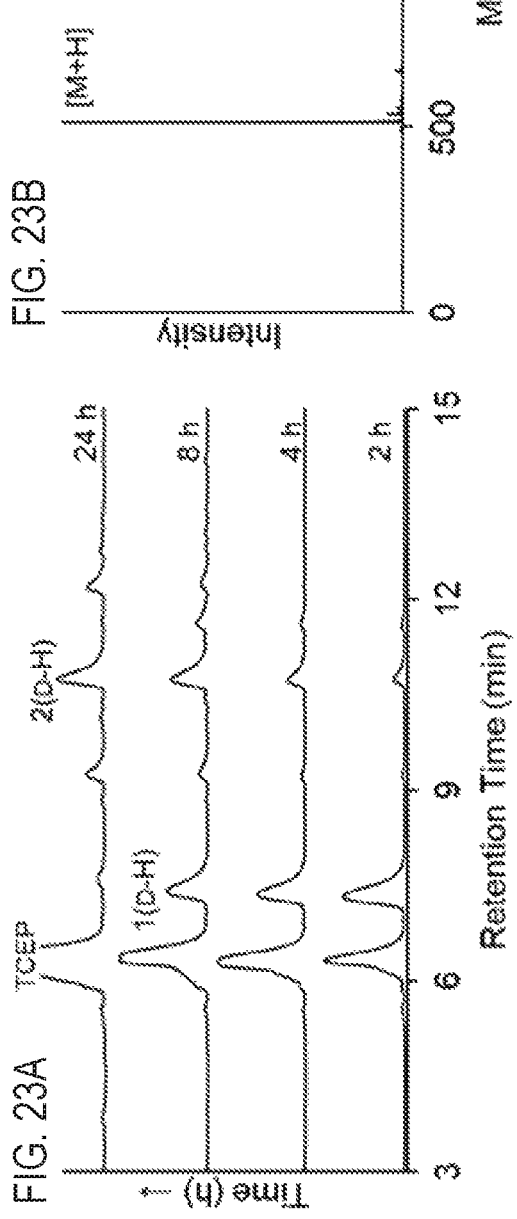
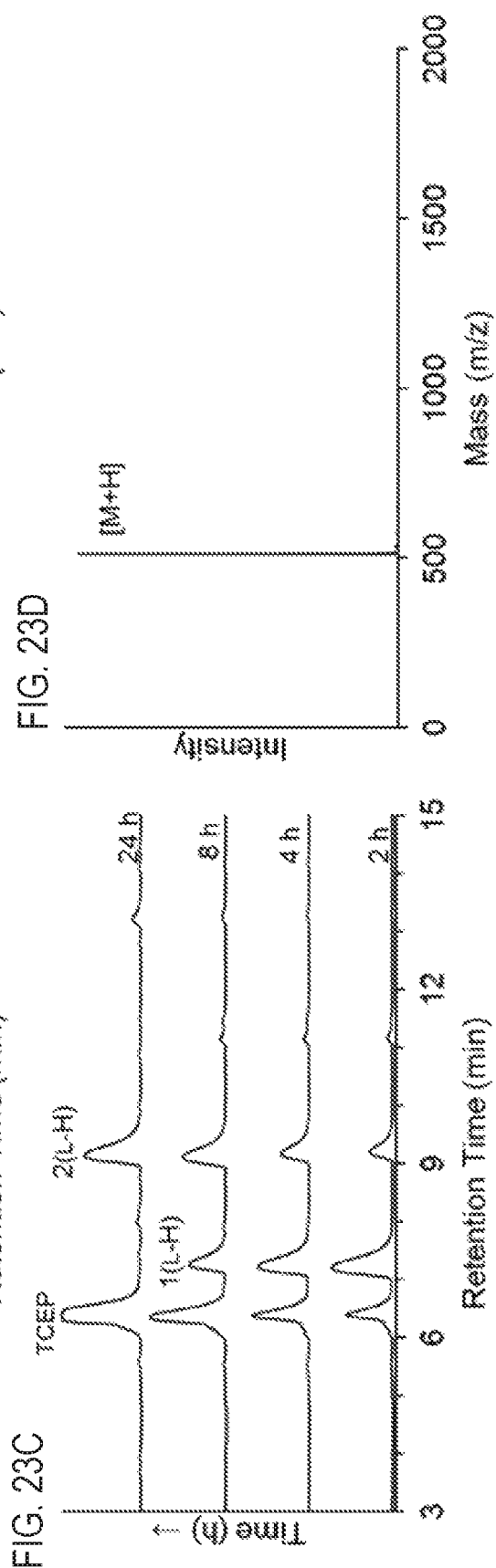
FIG. 23A  FIG. 23B  FIG. 23C  FIG. 23D

H$_2$N-MEEPQSDPSVEPPLSQETFSDLWKLLPENNVLSPL-MEGA
(SEQ ID NO:21)
FIG. 29A
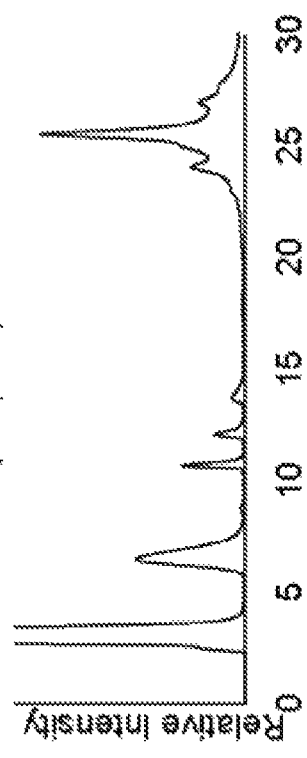
Crude p53(1-35)-MEGA
FIG. 29B
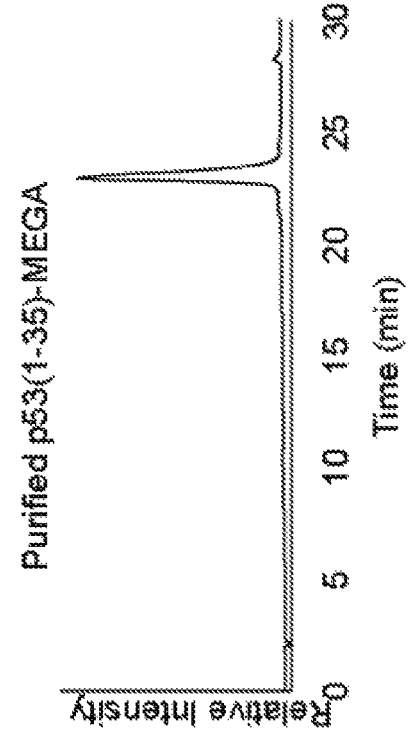
Purified p53(1-35)-MEGA
FIG. 29C
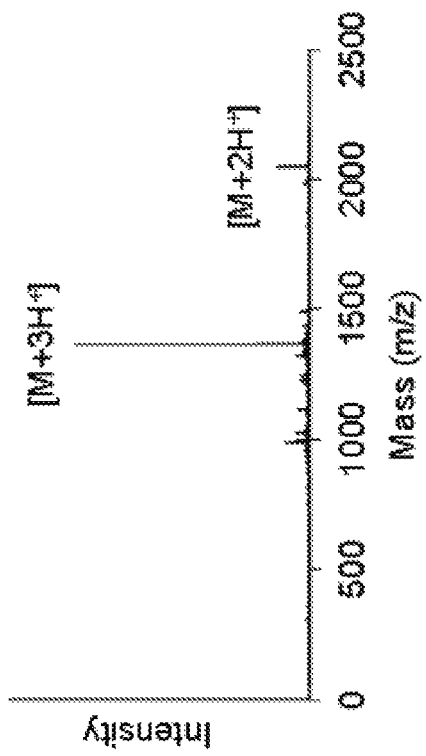
FIG. 29D

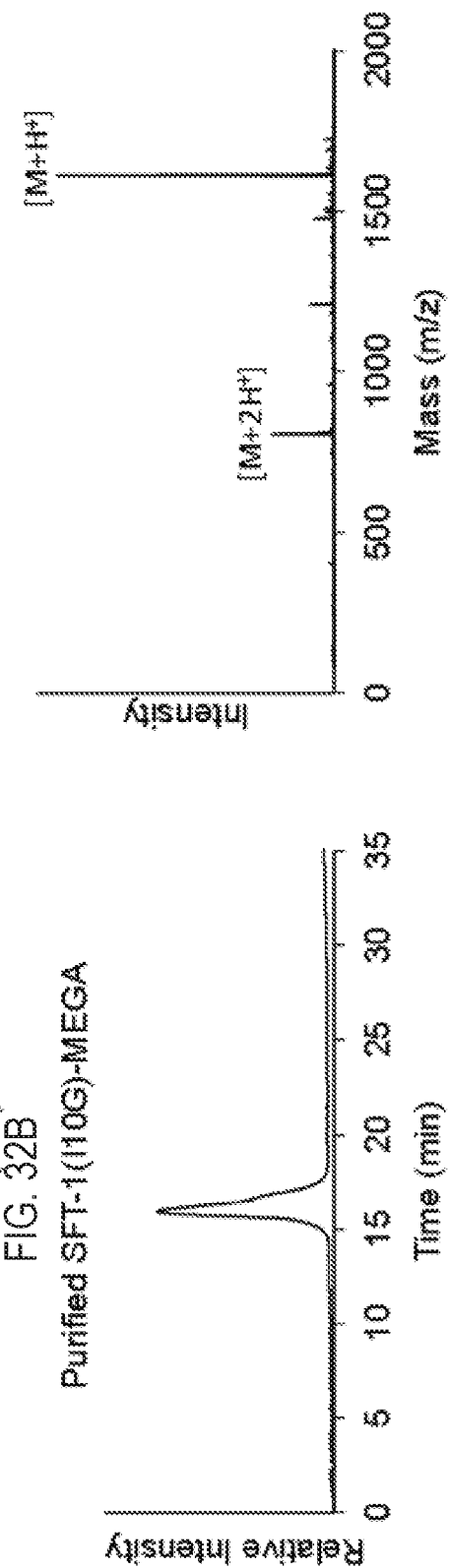
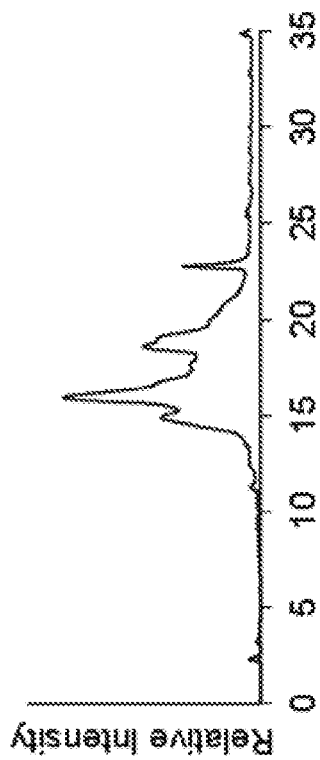
H₂N-CFPDGRCTKSIPPG-MEGA (SEQ ID NO: 25)
FIG. 32A
FIG. 32B
FIG. 32C
FIG. 32D

SEQUENCE LISTING

<160> NUMBER OF SEQ ID NOS: 26

<210> SEQ ID NO 1
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Ala Trp Lys Xaa
1

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Ala Trp Lys Gly
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Ala Trp Lys Ala
1

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 4

Ala Trp Lys Leu
1

<210> SEQ ID NO 5
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 5

Ala Trp Lys Val
1

<210> SEQ ID NO 6
<211> LENGTH: 4
<212> TYPE: PRT
<213> ORGANISM: Artificial Sequence
<220> FEATURE:
<223> OTHER INFORMATION: Synthetic polypeptide

```
<400> SEQUENCE: 6

Ala Trp Lys Asp
1

<210> SEQ ID NO 7
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 7

Ala Trp Lys Phe
1

<210> SEQ ID NO 8
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 8

Ala Trp Lys Gln
1

<210> SEQ ID NO 9
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 9

Ala Trp Lys Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Ala Trp Lys Ser
1

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 11

Ala Trp Lys Thr
1

<210> SEQ ID NO 12
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
```

```
<222> LOCATION: (4)..(4)
<223> OTHER INFORMATION: Xaa is D-Alanine

<400> SEQUENCE: 12

Ala Trp Lys Xaa
1

<210> SEQ ID NO 13
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 13

Ala Trp Lys Lys
1

<210> SEQ ID NO 14
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 14

Ala Trp Lys Cys
1

<210> SEQ ID NO 15
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Xaa is D-Cysteine

<400> SEQUENCE: 15

Ala Trp Lys Xaa
1

<210> SEQ ID NO 16
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 16

Cys Ala Ser Trp
1

<210> SEQ ID NO 17
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 17

Ala Trp Lys Gly Cys Ala Ser Trp
1               5

<210> SEQ ID NO 18
```

```
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 18

Ala Trp Lys Ala Cys Ala Ser Trp
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 19

Ala Trp Lys Leu Cys Ala Ser Trp
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 20

Cys Ala Ser His Glu Trp
1               5

<210> SEQ ID NO 21
<211> LENGTH: 35
<212> TYPE: PRT
<213> ORGANISM: Homo sapiens

<400> SEQUENCE: 21

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu
        35

<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Xaa is D-Histidine

<400> SEQUENCE: 22

Cys Leu Ala Ser Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide
```

```
<400> SEQUENCE: 23

Cys Leu Ala Ser His
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 24

Cys Leu Ala Ser His
1               5

<210> SEQ ID NO 25
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 25

Cys Phe Pro Asp Gly Arg Cys Thr Lys Ser Ile Pro Pro Gly
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 26

Ala Trp Lys Xaa Cys Ala Ser Trp
1               5
```

US 10,669,306 B2

SOLID SUPPORTS FOR USE IN SOLID-PHASE PEPTIDE SYNTHESIS, KITS, AND RELATED METHODS

CROSS-REFERENCE TO RELATED APPLICATIONS

This application is a 371 National Phase Application of International Application No. PCT/US2017/016455 filed on Feb. 3, 2017, which claims the benefit of and priority to U.S. Provisional Patent Application No. 62/291,061 filed on Feb. 4, 2016, all of which are incorporated herein by reference.

STATEMENT REGARDING FEDERALLY SPONSORED RESEARCH

This invention was made with government support under Grant No. 1 R01 GM110430-01, awarded by the National Institutes of Health, and Grant No. DGH-1256082, awarded by the National Science Foundation. The government has certain rights in the invention.

TECHNICAL FIELD

The present disclosure relates generally to solid supports for use in solid-phase peptide synthesis (SPPS). In particular, the solid supports may include a resin and a protected linker coupled to the resin. In particular embodiments, the linker may be an N-mercaptoethoxyglycine, an N-mercaptopropoxyglycine, and/or an N-mercaptobutoxyglycine. The present disclosure also relates to kits for use in SPPS. In particular, the kits may include the solid support, a solution including a thiol or a selenol, one or more pluralities of protected amino acids, and/or a wash buffer. The present disclosure also relates to methods of SPPS. In particular embodiments, the methods may include providing a solid support including a resin coupled to a protected linker.

BACKGROUND

Native chemical ligation (NCL) is a tool for the total synthesis and semi-synthesis of full-length proteins with site-specific post-translational modifications (see Dawson, P. E., et al. Science 1994, 266, 776). Application of NCL utilizes access to an N-terminal Cys-containing peptide fragment and a peptide C-terminal α-thioester. After an initial transthioesterification, whereby the Cys side-chain displaces the thiol from the C-terminal thioester fragment, a spontaneous S-to-N acyl shift leads to the thermodynamically stable amide bond (see FIG. 1A).

Peptide fragments bearing an N-terminal Cys can be obtained by SPPS using a 9-fluorenylmethoxycarbonyl (Fmoc-) α-amine protecting group strategy (see Flavell, R. R., et al. Acc. Chem. Res. 2009, 42, 107; Dhall, A., et al. ACS Chem. Biol. 2011, 6, 987; and Weller, C. E., et al. Biopolymers 2014, 101, 144) or by heterologous expression in Escherichia coli (see Erlanson, D. A., et al. Chem. Biol. 1996, 3, 981). In contrast, the direct synthesis of peptide α-thioesters by Fmoc-chemistry is limited by their inherent lability toward the organic bases employed for Fmoc-deprotection. Peptide α-thioesters may indeed be synthesized with a C-terminal thiol resin-linker using the tert-butyloxycarbonyl (Boc-) α-amine protecting group strategy (see Camarero, et al. J. Pept. Res. 1998, 51, 303 and Hackeng, T. M., et al. Proc. Natl. Acad. Sci. U.S.A. 1999, 96, 10068). However, applications of Boc-chemistry can have several limitations, including incompatibility with specific phosphorylated (see Otvos, L., et al. J. Pept. Protein Res. 1989, 34, 129) and glycosylated amino acids (see Gamblin, D. P., et al. Chem. Rev. 2009, 109, 131) and the use of hydrogen fluoride (HF) gas for peptide cleavage from the solid-phase (see Muttenthaler, M., et al. Nat. Protoc. 2015, 10, 1067). Recently, trifluoromethanesulfonic acid (TFMSA) has been reported as an alternative to HF, but the broad utility and functional group compatibility of TFMSA is currently unknown (see Gates, Z. P., et al. Chem. Commun. 2016, 52, 13979).

Common strategies to generate peptide α-thioesters generally use Fmoc-chemistry in conjunction with multi-step manipulation after SPPS (see Zheng, J. S., et al. Acc. Chem. Res. 2013, 46, 2475 and Blanco-Canosa, J. B., et al. J. Am. Chem. Soc. 2015, 137, 7197), or modification of the solid-phase linker prior to peptide assembly (see Erlich, L. A., et al. Org. Biomol. Chem. 2010, 8, 2392 and Ollivier, N., et al. Org. Lett. 2010, 12, 5238), each with its inherent limitations and synthetic challenges (see Mong, S. K., et al. ChemBioChem 2014, 15, 721). Several thioesterification strategies utilize modified C-terminal amino acids (see Erlich, L. A., et al. Org. Biomol. Chem. 2010, 8, 2392) or strongly acidic conditions and elevated temperatures with Cys (see Kang, J., et al. Org. Biomol. Chem. 2009, 7, 4918) to favor intramolecular N-to-S acyl shift of the backbone amide bond, followed by transthioesterification with external thiols. Functionalized resins containing alkyl thiols that are suitably poised for nucleophilic attack at the C-terminal amide bond (see Taichi, M., et al. Org. Lett. 2013, 15, 2620), also known as crypto-thioesters (see Sato, K., et al. ChemBioChem 2011, 12, 1840), hold promise due to the minimal chemical manipulation required post-SPPS (see Tailhades, J., et al. J. Pept. Sci. 2015, 21, 139). The complex chemistry required to install crypto-thioesters, however, can limit their accessibility to a handful of laboratories. Therefore, efforts to expand the utility of NCL may benefit from facile and high-yielding Fmoc-based strategies to access peptide α-thioesters.

BRIEF DESCRIPTION OF THE DRAWINGS

The embodiments disclosed herein will become more fully apparent from the following description and appended claims, taken in conjunction with the accompanying drawings.

FIG. 4E depicts purified AWK(D-A)-MEGA (SEQ ID NO:12).

FIG. 4F depicts ESI-MS of purified AWK(D-A)-MEGA (SEQ ID NO:12). Calcd. [M+H$^+$] 607.7 Da, obsd. 607.4 Da.

FIG. 4G depicts purified AWKL-MEGA (SEQ ID NO:4).

FIG. 4H depicts ESI-MS of purified AWKL-MEGA (SEQ ID NO:4). Calcd. [M+H$^+$] 648.8 Da, obsd. 648.5 Da.

FIG. 4I depicts purified AWKF-MEGA (SEQ ID NO:7).

FIG. 4J depicts ESI-MS of purified AWKF-MEGA (SEQ ID NO:7). Calcd. [M+H$^+$] 682.8 Da, obsd. 682.6 Da.

FIG. 4K depicts purified AWKV-MEGA (SEQ ID NO:5).

FIG. 4L depicts ESI-MS of purified AWKV-MEGA (SEQ ID NO:5). Calcd. [M+H$^+$] 634.8 Da, obsd. 634.4 Da.

FIG. 4M depicts purified AWKT-MEGA (SEQ ID NO:11).

FIG. 4N depicts ESI-MS of purified AWKT-MEGA (SEQ ID NO:11). Calcd. [M+H$^+$] 636.8 Da, obsd. 636.5 Da.

FIG. 4O depicts purified AWKS-MEGA (SEQ ID NO:10).

FIG. 4P depicts ESI-MS of purified AWKS-MEGA (SEQ ID NO:10). Calcd. [M+H$^+$] 622.7 Da. obsd. 622.6 Da.

FIG. 4Q depicts purified AWKR-MEGA (SEQ ID NO:9).

FIG. 4R depicts ESI-MS of purified AWKR-MEGA (SEQ ID NO:9). Calcd. [M+H$^+$] 691.9 Da, obsd. 691.5 Da.

FIG. 4S depicts purified AWKQ-MEGA (SEQ ID NO:8).

FIG. 4T depicts ESI-MS of purified AWKQ-MEGA (SEQ ID NO:8). Calcd. [M+H$^+$] 663.8 Da, obsd. 663.8 Da.

FIG. 4AA depicts purified AWK(D-C)-MEGA (SEQ ID NO:15).

FIG. 4BB depicts ESI-MS of purified AWK(D-C)-MEGA (SEQ ID NO:15). Calcd. [M+H$^+$] 639.8 Da, obsd. 639.5 Da. For FIGS. 4A-4BB, *=MS-fragmentation of full-length peptide corresponding to loss of N-terminal Ala. RP-HPLC performed on C18 analytical column, 0-73% B, 30 minute gradient.

FIG. 7A is a C18 RP-HPLC time-course of thioester formation for an AWKG-MEGA (SEQ ID NO:2) peptide. Buffer: 200-400 mM MESNa, 100 mM NaH$_2$PO$_4$, 25-50 mM TCEP. RP-HPLC: 10-60% CH$_3$CN in water, 30 minute gradient.

FIG. 7B is a C18 RP-HPLC time-course of thioester formation for an AWKA-MEGA (SEQ ID NO:3) peptide. Buffer: 200-400 mM MESNa, 100 mM NaH$_2$PO$_4$, 25-50 mM TCEP. RP-HPLC: 10-60% CH$_3$CN in water, 30 minute gradient.

FIG. 7C is a C18 RP-HPLC time-course of thioester formation for an AWKL-MEGA (SEQ ID NO:4) peptide. Buffer: 200-400 mM MESNa, 100 mM NaH$_2$PO$_4$, 25-50 mM TCEP. RP-HPLC: 10-60% CH$_3$CN in water, 30 minute gradient.

FIG. 9I depicts an AWKT-MEGA (SEQ ID NO:11) thioesterification time-course.

FIG. 9J depicts ESI-MS of AWKT-MES (SEQ ID NO:11) thioester. Calcd. [M+H$^+$] 628.8 Da, obsd. 628.7 Da.

FIG. 9K depicts an AWKS-MEGA (SEQ ID NO:10) thioesterification time-course.

FIG. 9L depicts ESI-MS of AWKS-MES (SEQ ID NO:10) thioester. Calcd. [M+H$^+$] 614.7 Da, obsd. 614.4 Da.

FIG. 9U depicts an AWKC-MEGA (SEQ ID NO:14) thioesterification time-course.

FIG. 9V depicts ESI-MS of AWKC-MES (SEQ ID NO:14) thioester. Calcd. [M+H⁺] 631.8 Da, obsd. 631.4 Da.

FIG. 9W depicts an AWKF-MEGA (SEQ ID NO:7) thioesterification time-course.

FIG. 9X depicts ESI-MS of AWKF-MES (SEQ ID NO:7) thioester. Calcd. [M+H⁺] 675.8 Da, obsd. 675.3 Da.

FIG. 14A is the amino acid sequence of p53(1-35)-MEGA (SEQ ID NO:21).

FIG. 14B depicts RP-HPLC of crude p53(1-35)-MEGA (SEQ ID NO:21) peptide product after TFA cleavage from solid support (0-73% B, 30 minute gradient).

FIG. 14C depicts RP-HPLC of pure p53(1-35)-MEGA (SEQ ID NO:21) (0-73% B, 30 minute gradient). Inset is ESI-MS of purified p53(1-35)-MEGA (SEQ ID NO:21). Calcd. [M+H⁺] 4,098.6 Da, obsd. 4,097.7±0.7 Da.

FIG. 14D depicts a thioesterification time-course of p53(1-35)-MEGA (SEQ ID NO:21) (C18 RP-HPLC, 30-80% B, 30 minute gradient). Buffer: 400 mM MESNa, 100 mM NaH₂PO₄, 25 mM TCEP, pH 4.5, 70° C. *=p53(1-35)-MEGA (SEQ ID NO:21) thioester.

FIG. 14E depicts ESI-MS of isolated p53(1-35) C-terminal thioester; Calcd. [M+H⁺] 4,091.6 Da, obsd. 4,090.9±2.2 Da.

FIG. 16A is a C18 analytical RP-HPLC chromatogram of purified CASW (SEQ ID NO:16), 0-73% B, 30 minute gradient.

FIG. 16B depicts ESI-MS of purified CASW (SEQ ID NO:16). Calcd. [M+H⁺] 464.2 Da, obsd. 464.2 Da.

FIG. 21A is a scheme depicting the cyclization reaction of CASHEW-MEGA (SEQ ID NO:20) (top) and RP-HPLC time-course of CASHEW-MEGA cyclization (SEQ ID NO:20) (bottom).

FIG. 21B is a scheme depicting the cyclization reaction of CRGD(D-F)-MEGA (top) and RP-HPLC time-course of CRGD(D-F)-MEGA cyclization (bottom). For FIGS. 21A and 21B, *=Cyclized peptide, **=Initial MEGA peptide. RP-HPLC performed on C18 analytical column, 10-60% B, 30 minute gradient.

FIG. 22A is a C18 analytical RP-HPLC chromatogram of purified CLAS(D-H)-MEGA (SEQ ID NO:22) peptide.

FIG. 22B depicts ESI-MS of purified CLAS(D-H)-MEGA (SEQ ID NO:22) peptide. Calcd. [M+H$^+$] 662.8 Da, obsd. 662.6 Da.

FIG. 22C is a C18 analytical RP-HPLC chromatogram of purified CLAS(L-H)-MEGA (SEQ ID NO:23) peptide.

FIG. 22D depicts ESI-MS of purified CLAS(L-H)-MEGA (SEQ ID NO:22) peptide. Calcd. [M+H$^+$] 662.8 Da, obsd. 662.5. For FIGS. 22A-22D, RP-HPLC performed on C18 analytical column, 0-73% B, 30 minute gradient.

FIG. 23A depicts a CLAS(D-H) (SEQ ID NO:22) cyclization time-course.

FIG. 23B depicts ESI-MS of purified cyclic CLAS(D-H) (SEQ ID NO:22) peptide. Calcd. [M+H$^+$] 512.2 Da, obsd. 512.4 Da.

FIG. 23C depicts a CLAS(L-H) (SEQ ID NO:23) cyclization time-course.

FIG. 23D depicts ESI-MS of purified cyclic CLAS(L-H) (SEQ ID NO:23) peptide. Calcd. [M+H$^+$] 512.2 Da, obsd. 512.4 Da.

FIG. 26A depicts an RP-HPLC time-course of SFT-1 (I10G)-MEGA (SEQ ID NO:25) thioesterification. Buffer: 400 mM MESNa, 100 mM NaH$_2$PO$_4$, 25 mM TCEP, pH 5.6, 70° C. *=Cyclized product, **=SFT-1(I10G)-MEGA (SEQ ID NO:25) peptide.

Figure 26B:
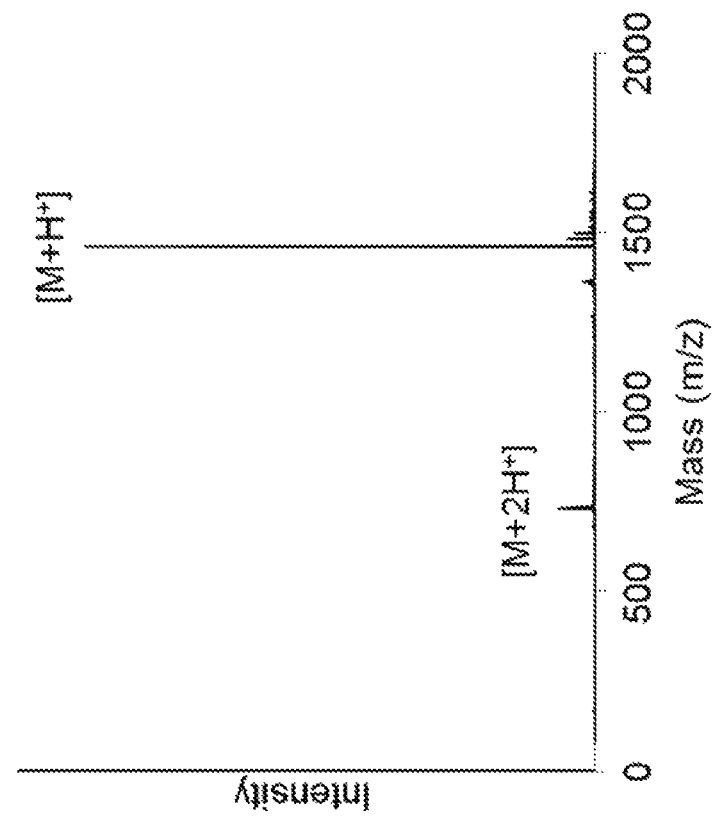

FIG. 26B depicts ESI-MS of SFT-1 (I10G) cyclized product. Calcd. [M+H$^+$] 1,459.7 Da, obsd. 1,459.4 Da. RP-HPLC performed on C18 analytical column, 10-60% B, 30 minute gradient.

Figure 27B:
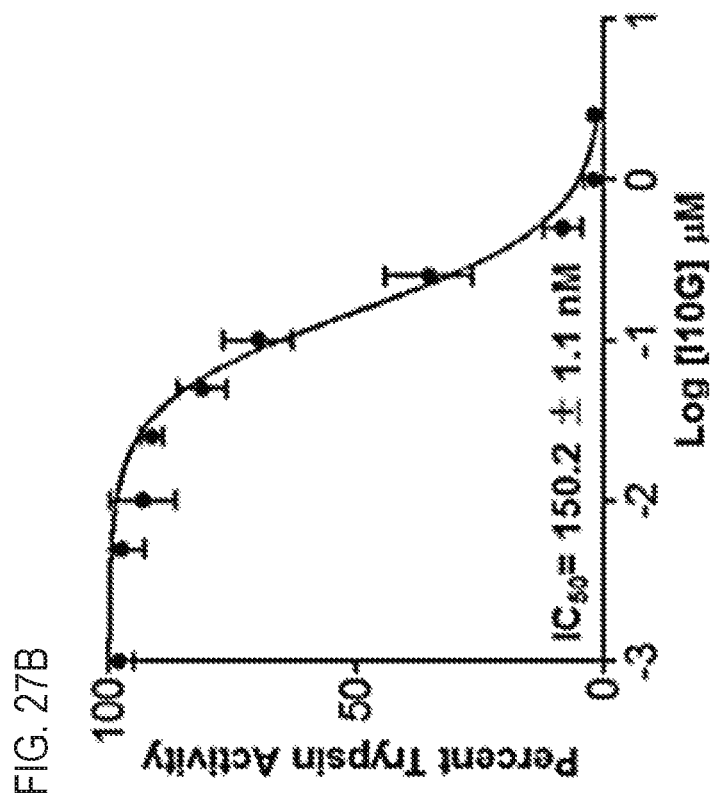
Figure 27A:
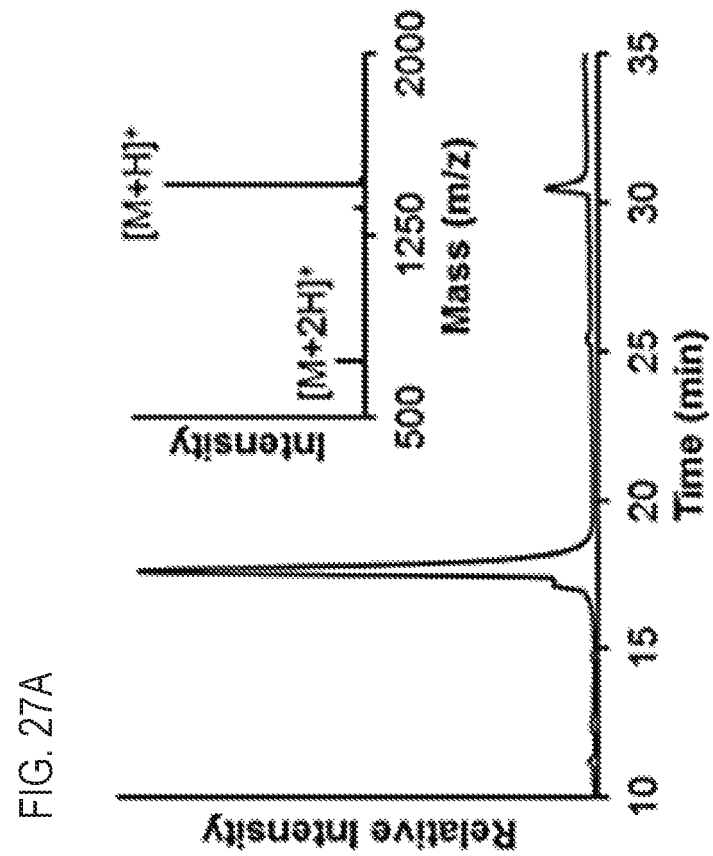

FIG. 27A is a C18 RP-HPLC of cyclized and oxidized SFT-1 (I10G) product. Inset is the ESI-MS of purified SFT-1 (I10G); Calcd. [M+H$^+$] 1,458.7 Da, obsd. 1,458.6±0.3 Da. RP-HPLC: 0-73% CH$_3$CN in water, 30 minute gradient.

FIG. 27B is a dose-response curve for the inhibition of bovine trypsin activity by SFT-1 (I10G). RP-HPLC: 0-73% CH$_3$CN in water, 30 minute gradient.

Figure 28A:
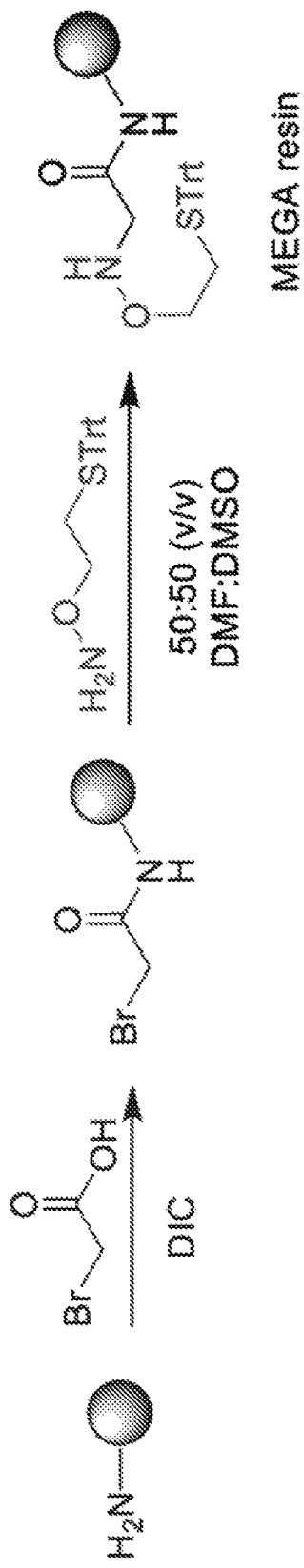

FIG. 28A depicts a scheme for the synthesis of MEGA resin.

Figure 28B:
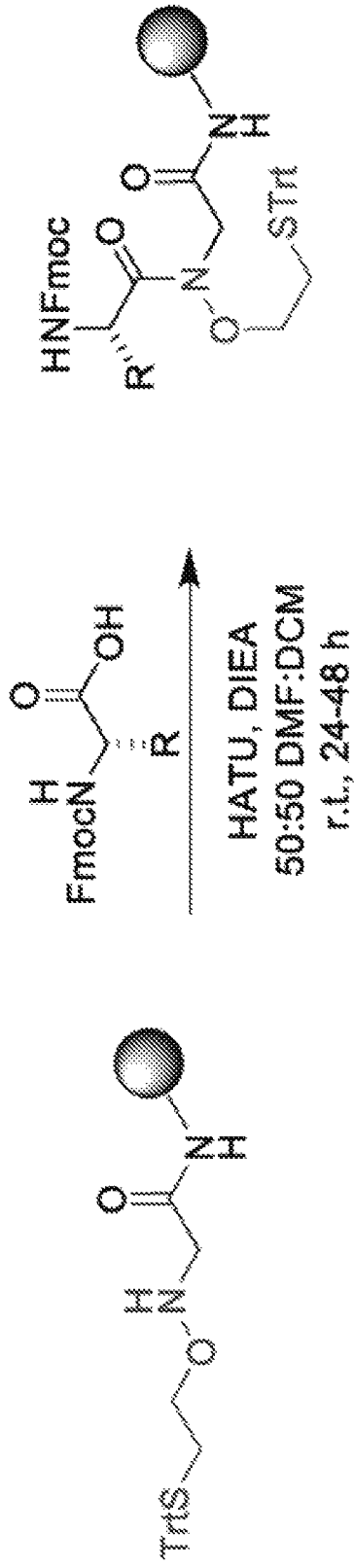

FIG. 28B depicts a scheme for first amino acid coupling.

FIG. 29A is the amino acid sequence of p53(1-35)-MEGA (SEQ ID NO:21).

FIG. 29B is a C18 RP-HPLC of crude p53(1-35)-MEGA (SEQ ID NO:21). 0-73% CH$_3$CN in water, 30 minute gradient.

FIG. 29C is a C18 RP-HPLC of purified p53(1-35)-MEGA (SEQ ID NO:21). 0-73% CH$_3$CN in water, 30 minute gradient.

FIG. 29D depicts ESI-MS of purified p53(1-35)-MEGA (SEQ ID NO:21). Calcd. [M+H$^+$] 4099.6 Da, obsd. 4099.6 Da.

Figure 30A:
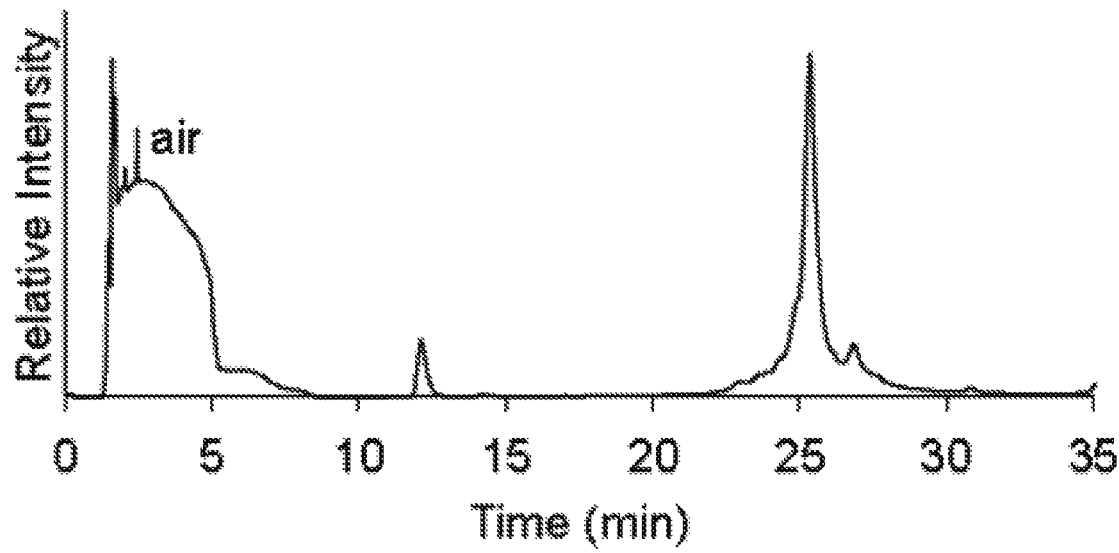

FIG. 30A is a C18 RP-HPLC of crude p53(1-35)-MEGA (SEQ ID NO:21). 0-73% CH$_3$CN in water, 30 minute gradient.

Figure 30B:
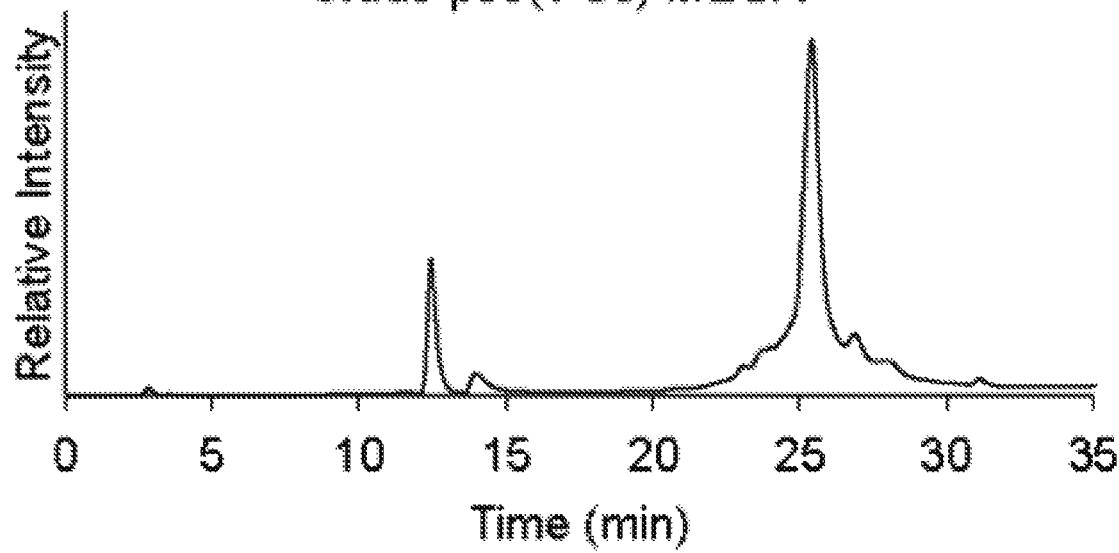

FIG. 30B is a C18 RP-HPLC of crude p53(1-35)-MEGA (SEQ ID NO:21). 0-73% CH$_3$CN in water, 30 minute gradient.

Figure 31B:
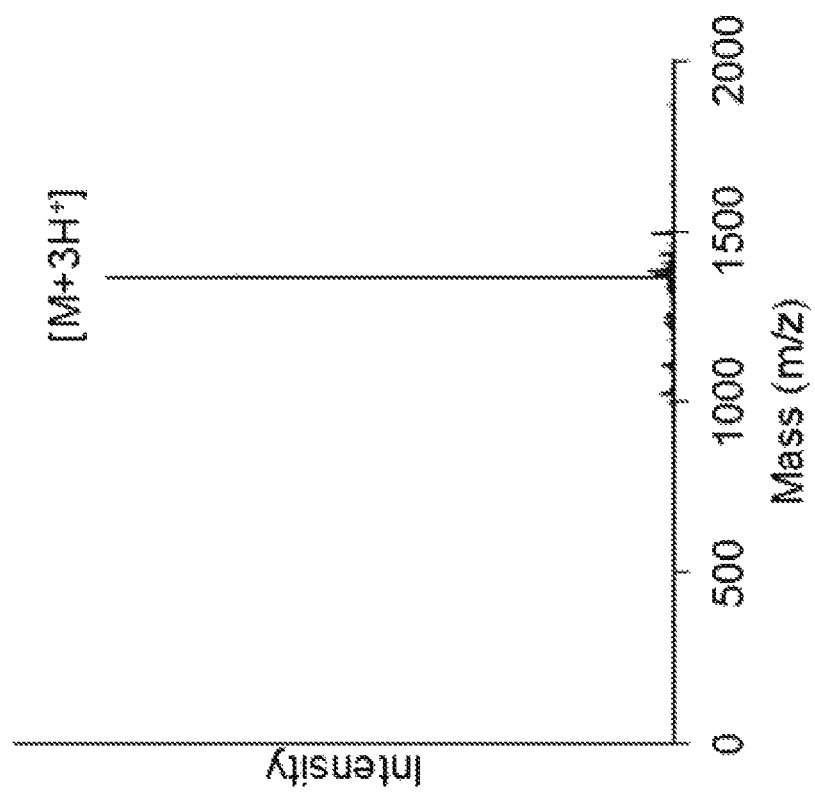
Figure 31A:
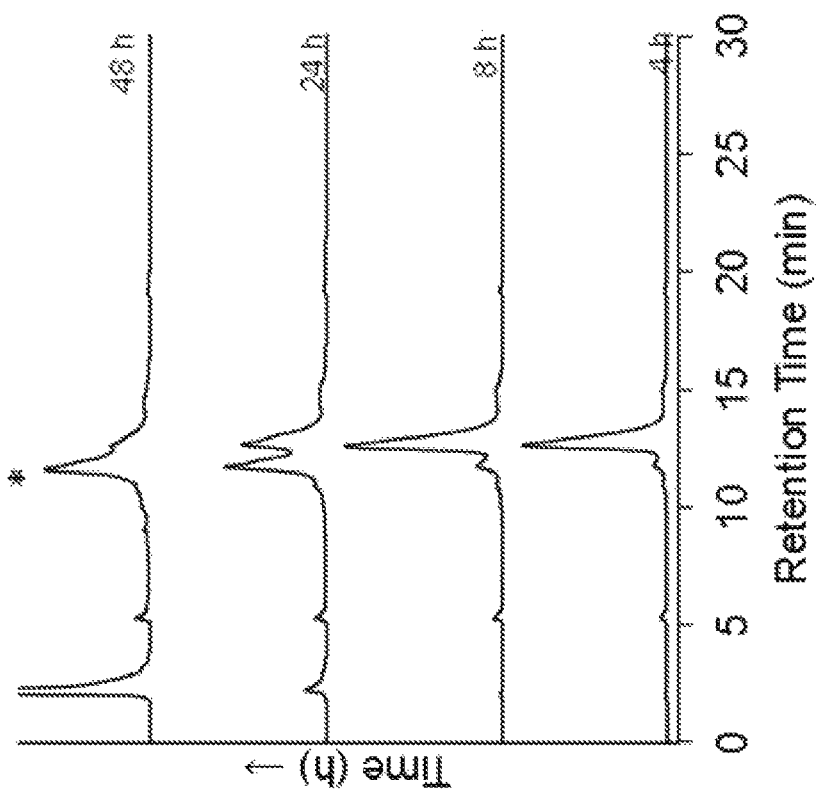

FIG. 31A depicts a C18 RP-HPLC time-course for the formation of p53(1-35) thioester (SEQ ID NO:21). 10-60% CH$_3$CN in water, 30 minute gradient.

FIG. 31B depicts ESI-MS of purified p53(1-35)-MES thioester (SEQ ID NO:21). Calcd. [M+H$^+$] 4091.6 Da, obsd. 4090.9 Da.

FIG. 32A is the amino acid sequence of SFT-1(I10G)-MEGA (SEQ ID NO:25).

FIG. 32B is a C18 RP-HPLC of crude SFT-1(I10G)-MEGA (SEQ ID NO:25). 0-73% CH$_3$CN in water, 30 minute gradient.

FIG. 32C is a C18 RP-HPLC of purified SFT-1(I10G)-MEGA (SEQ ID NO:25). 0-73% CH$_3$CN in water, 30 minute gradient.

FIG. 32D depicts ESI-MS of purified SFT-1(I10G)-MEGA (SEQ ID NO:25). Calcd. [M+H$^+$] 1609.9 Da, obsd. 1609.8 Da.

Figure 33:
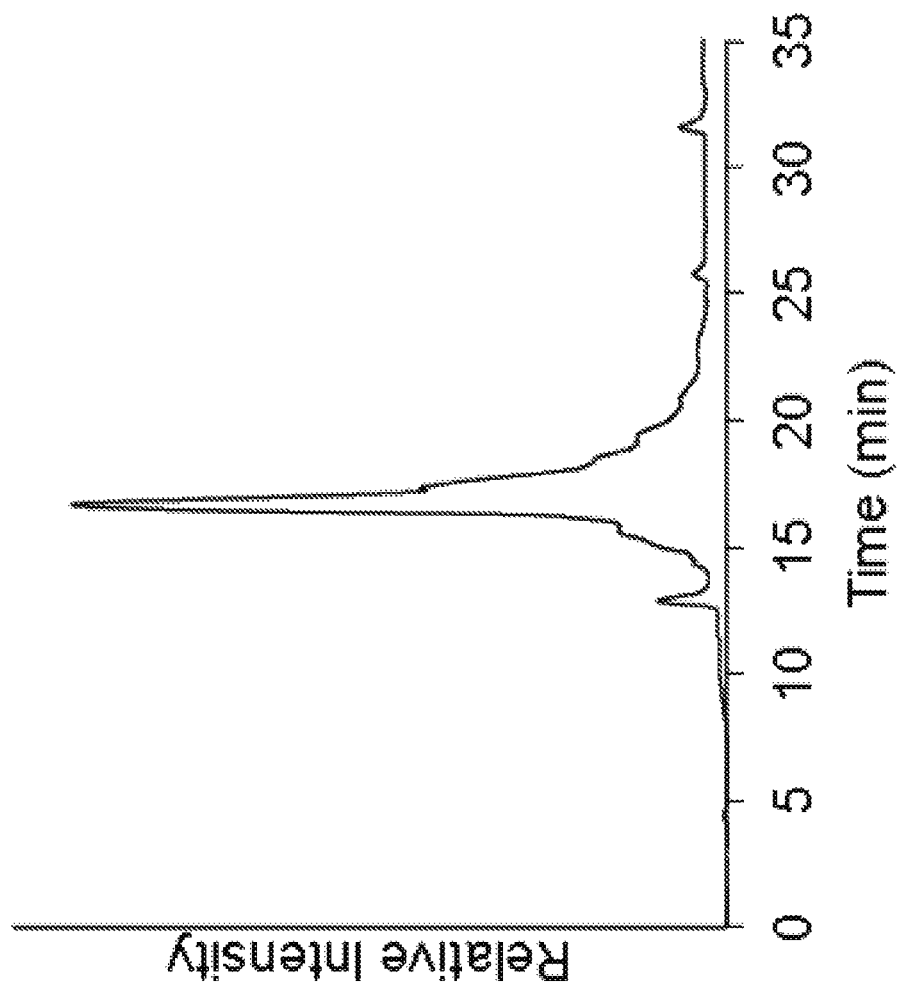

FIG. 33 is a C18 RP-HPLC of crude SFT-1(I10G)-MEGA (SEQ ID NO:25). 0-73% CH$_3$CN in water, 30 minute gradient.

Figure 34B:
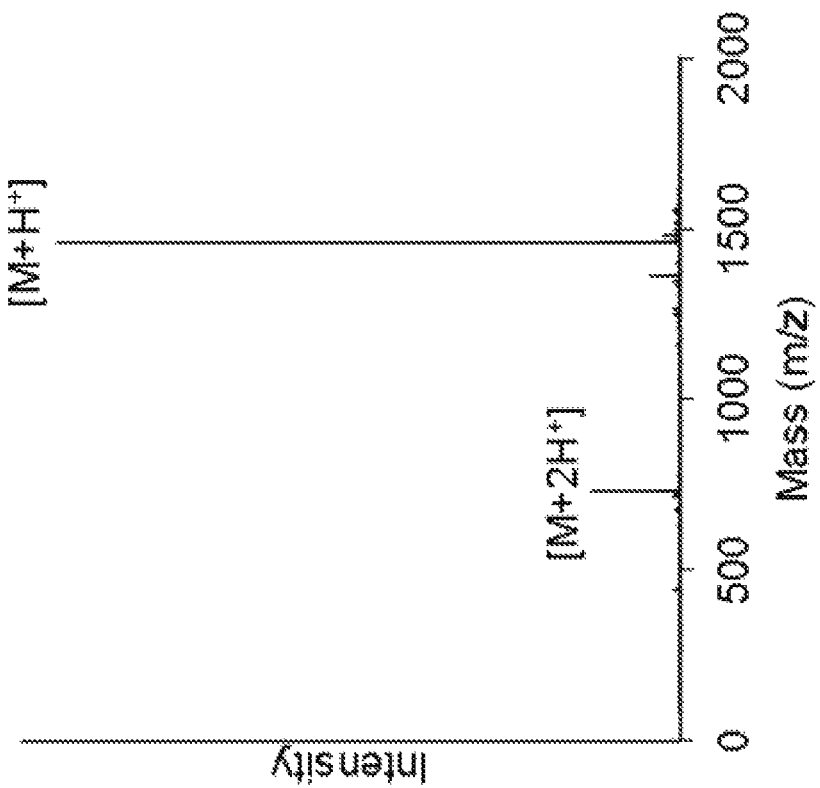
Figure 34A:
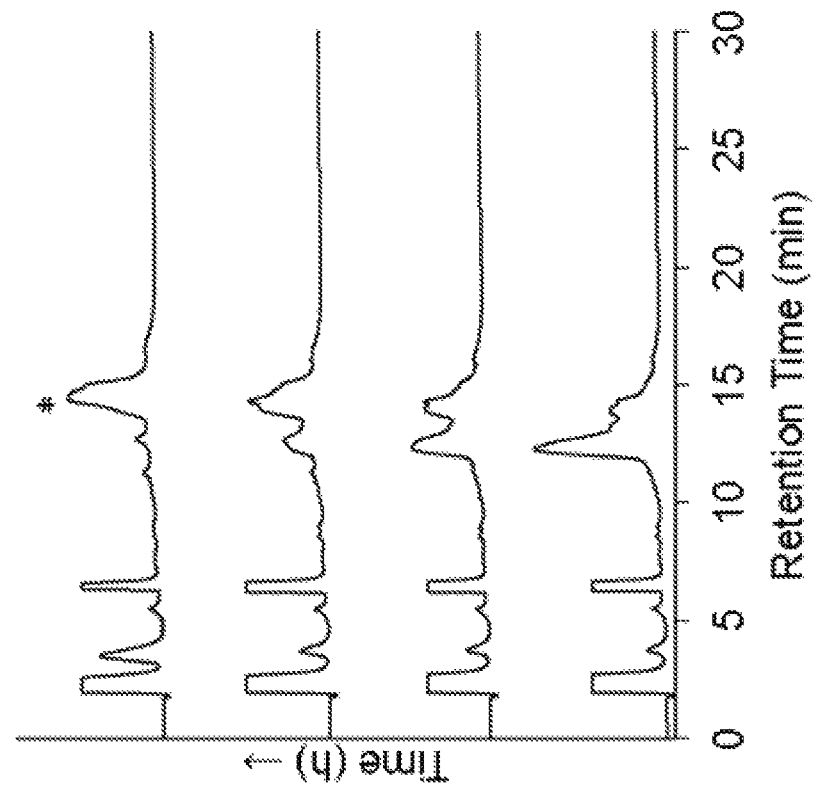

FIG. 34A depicts a cyclization time-course of SFT-1 (I10G)-MEGA (SEQ ID NO:25).

FIG. 34B depicts ESI-MS of purified cyclic SFT-1(I10G) (SEQ ID NO:25). Calcd. [M+H$^+$] 1,459.7 Da, obsd. 1,459.4 Da.

Figure 35A:
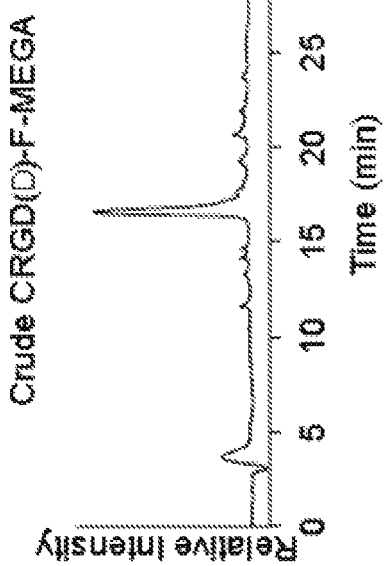

FIG. 35A depicts the chemical structure of cyclic CRGD (D)-F.

Figure 35B:
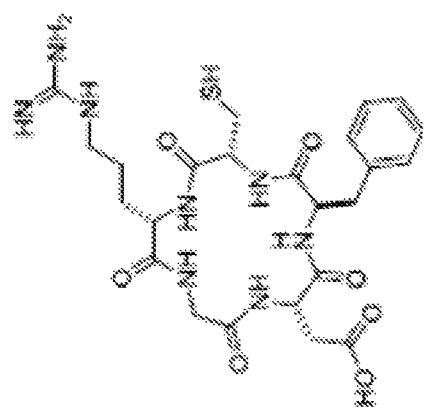

FIG. 35B is a C18 RP-HPLC of crude CRGD(D)-F-MEGA. 0-73% CH$_3$CN in water, 30 minute gradient.

Figure 35C:
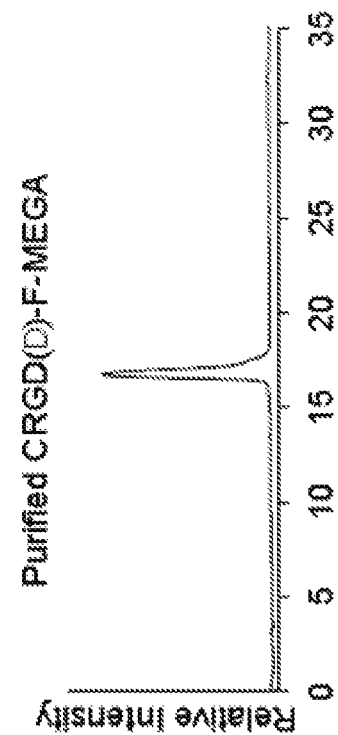

FIG. 35C is a C18 RP-HPLC of purified CRGD(D)-F-MEGA. 0-73% CH$_3$CN in water, 30 minute gradient.

Figure 35D:
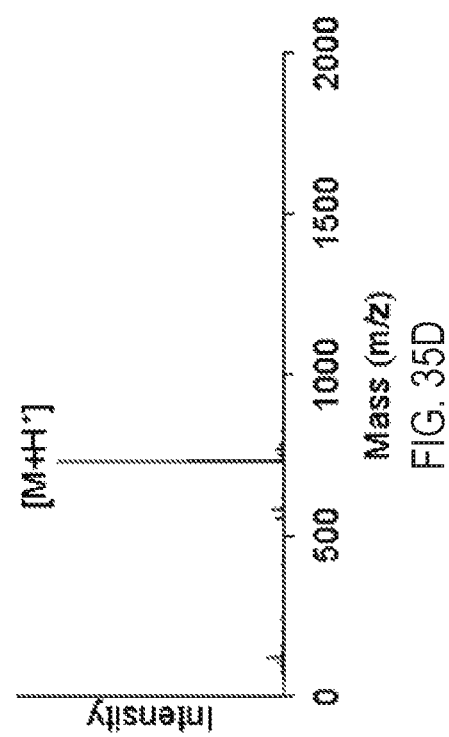

FIG. 35D depicts ESI-MS of purified CRGD(D)-F-MEGA. Calcd. [M+H$^+$] 728.8 Da, obsd. 728.7 Da.

Figures 36A, 36B:
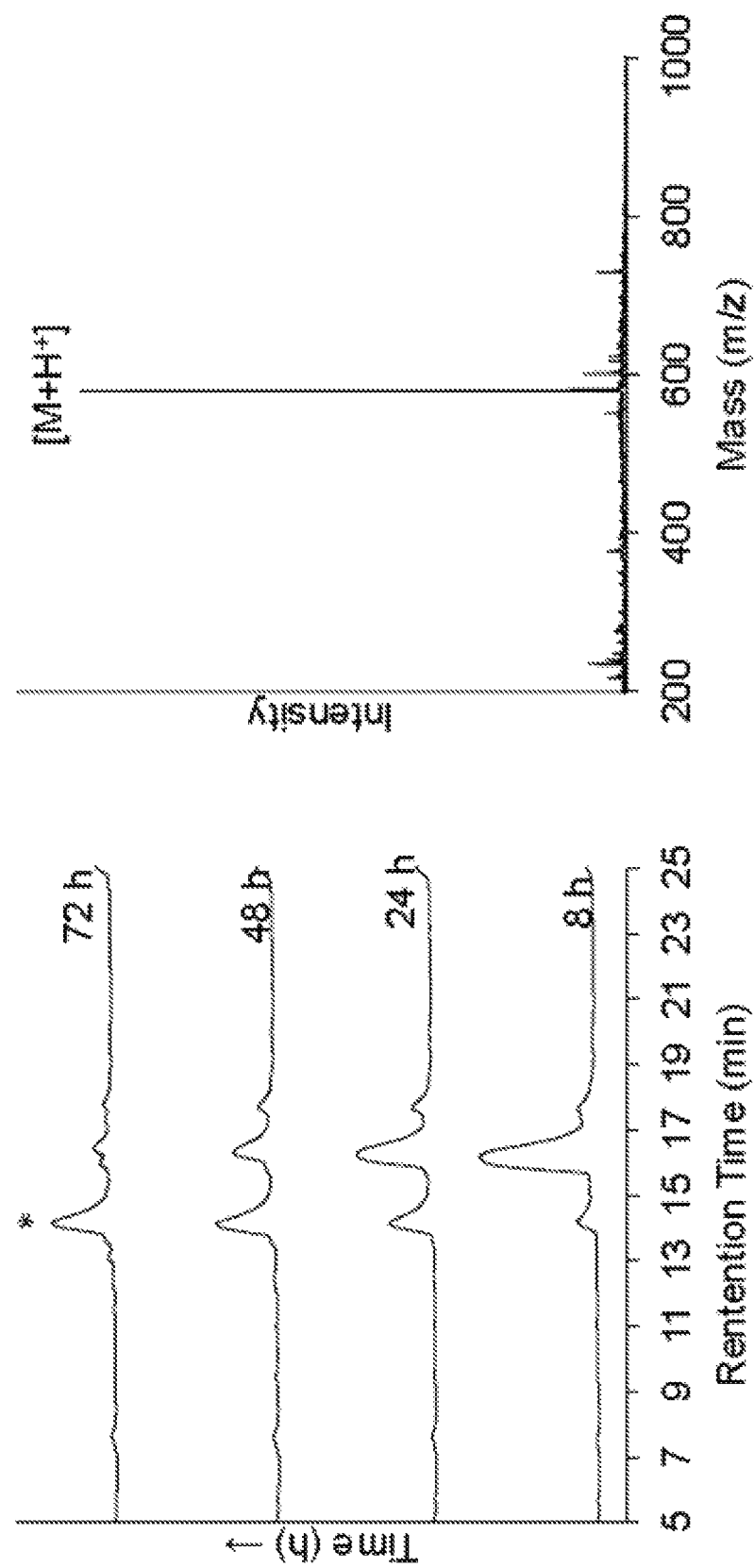

FIG. 36A depicts a cyclization time-course of CRGD(D)-F-MEGA.

FIG. 36B depicts ESI-MS of purified cyclic CRGD(D)-F. Calcd. [M+H$^+$] 579.7 Da, obsd. 579.8 Da.

DETAILED DESCRIPTION

The present disclosure relates generally to solid supports for use in SPPS. The solid supports may include a resin and a protected linker coupled to the resin. The linker may be an N-mercaptoethoxyglycine, an N-mercaptopropoxyglycine, an N-mercaptobutoxyglycine, and/or another suitable linker. The present disclosure also relates to kits for use in SPPS. The kits may include a solid support as provided herein, a solution including a thiol or a selenol, one or more pluralities of protected amino acids, and/or a wash buffer. The present disclosure also relates to methods of SPPS. The methods may include providing a solid support including a resin coupled to a protected linker.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. Unless specifically defined otherwise, the technical terms, as used herein, have their normal meaning as understood in the art.

Figure 1B:
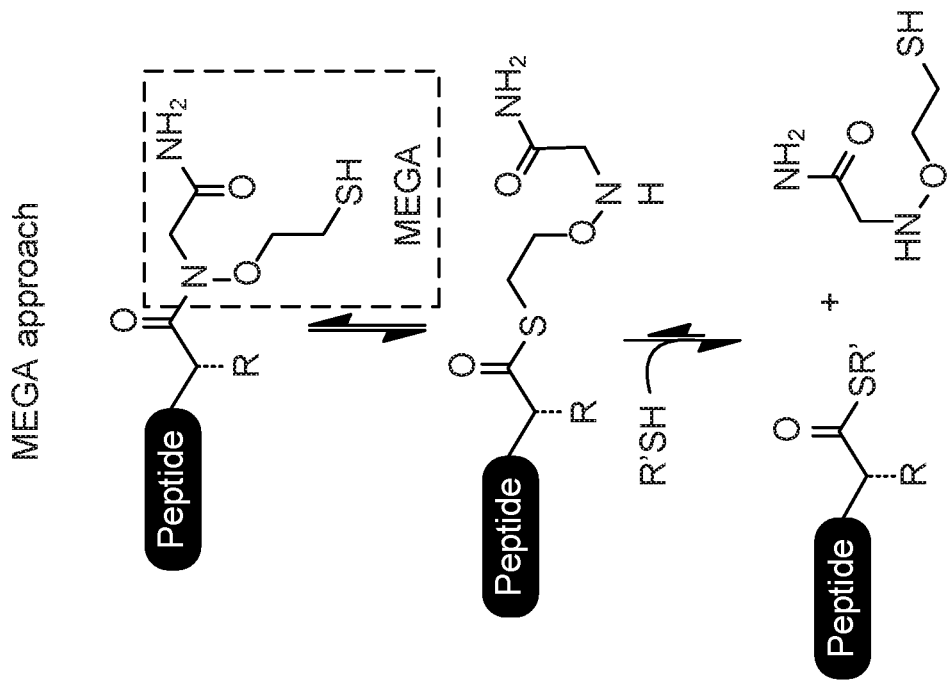
FIG. 1B depicts the N-mercaptoethoxyglycinamide (MEGA) approach to peptide thioesterification.
Figure 1A:
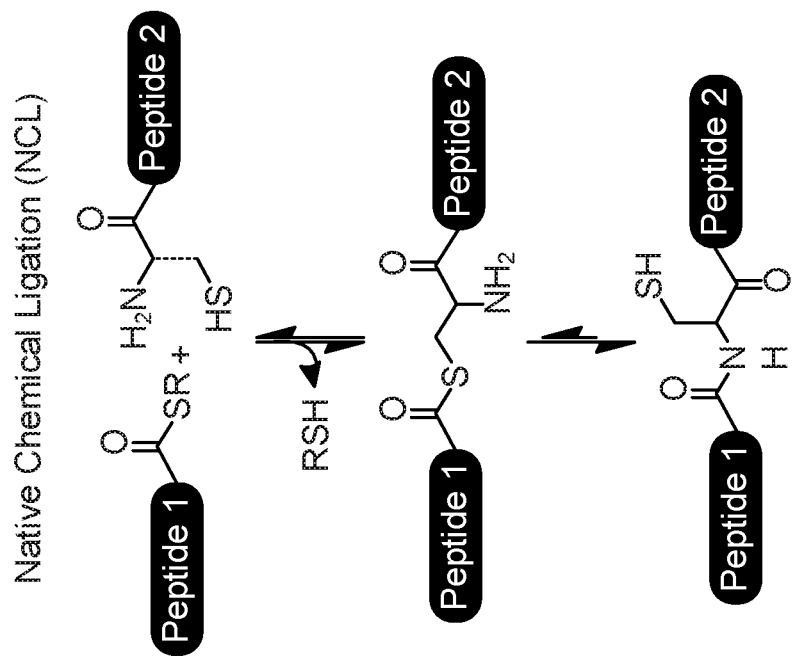
FIG. 1A depicts the principle of NCL.

An N-mercaptoethoxyglycinamide (MEGA) linker approach for the facile synthesis of peptide α-thioesters is provided herein. NCL products containing the ligation auxiliary, 2-(aminooxy)ethanethiol, may undergo thiolysis at room temperature to regenerate the initial reactive α-thioester fragment (see FIG. 1B). Peptides synthesized with the C-terminal MEGA linker can be readily converted to their α-thioester form under mildly acidic conditions and can be directly applied toward NCL without further purification. The MEGA linker strategy can be compatible with a wide-range of C-terminal amino acids, including sterically demanding β-branched amino acids. Furthermore, MEGA can be useful for the one-pot synthesis of cyclic peptides (see Korsinczky, M. L., et al. J. Curr. Protein Pept. Sci. 2004, 5, 351).

A first aspect of the disclosure relates to a solid support for use in SPPS. In some embodiments, the solid support may include a resin. In various embodiments, the resin may be insoluble or substantially insoluble. The solid support may also include a linker coupled to the resin. In certain embodiments, the linker may be at least one of an N-mercaptoethoxyglycine, an N-mercaptopropoxyglycine, and/or an N-mercaptobutoxyglycine. In various embodiments, other chalcogens, such as selenium, may be used in place of the sulfur. For example, the linker may include a selenol moiety in place of the thiol moiety. Other suitable linkers are also within the scope of this disclosure.

In some embodiments, the linker may be coupled to a protecting group. For example, the linker may be coupled to a protecting group selected from at least one of an orthonitrobenzyl group, a trityl group, an acetamidomethyl group, an alkyl thiol group, and/or an aromatic thiol group. Other suitable protecting groups are also within the scope of this disclosure. Furthermore, the protecting group may be coupled to a sulfur molecule of the linker.

In certain embodiments, the resin of the solid support may be selected from at least one of a Rink amide resin, a peptide amide linker (PAL) resin, a 4-hydroxymethyl-phenylacetamidomethyl (PAM) resin, a benzhydrylamine hydrochloride salt (BHA) resin, a 4-methylbenzhydrylamine hydrochloride salt (MBNA) resin, a Wang resin, a 4-hydroxybenzyl alcohol (PHB) resin, a 4-(hydroxymethyl)-phenoxyacetic acid (HMPA) resin, an 4-(4-hydroxymethyl-3-methoxyphenoxy)butyric acid (HMPB) resin, an aminomethyl resin, a polystyrene (PS) resin, and/or a polyethylene glycol-polystyrene (PEG-PS) resin. Other suitable resins are also within the scope of this disclosure.

Another aspect of the disclosure relates to kits for use in SPPS. In some embodiments, the kit may include a solid support as described above. For example, the kit may include a resin, wherein the resin is coupled to a linker. The resin may be coupled to at least one of an N-mercaptoethoxyglycine, an N-mercaptopropoxyglycine, an N-mercaptobutoxyglycine, and/or another suitable linker. The kit may also include a wash buffer, for example, N,N-dimethylformamide (DMF), N-methylmorpholine (NMM), dimethylsulfoxide (DMSO), and/or dichloromethane (DCM).

The kit may also include a solution comprising a thiol or a selenol. In various embodiments, the thiol may be an aliphatic thiol. In certain embodiments, the thiol may be at least one of a mercaptoethanesulfonate, an ethanethiol, and/or a glutathione. Other suitable thiols are also within the scope of this disclosure. The pH of the solution (e.g., the solution including the thiol) may be between about 4 and about 7. In certain embodiments, the pH of the solution may be between about 2 and about 9, between about 3 and about 8, between about 4 and about 6, between about 4 and about 5.6, or another suitable pH. In some embodiments, the solution may include a chalcogen that is the same as, consistent with, and/or compatible with the chalcogen in the linker. For example, in certain embodiments wherein the resin is coupled to a linker including a selenol moiety, the kit may include a solution comprising a selenol.

Furthermore, the thiol may have a pKa between about 7 and about 10. In various embodiments, the thiol may have a pKa between about 8 and about 10, between about 8.5 and about 9.5, about 9, or another suitable pKa. Additionally, the thiol may have a vapor pressure of between about 0 mmHg and about 550 mmHg at 25° C. In some embodiments, the thiol may have a vapor pressure of between about 100 mmHg and about 540 mmHg at 25° C., between about 300 mmHg and about 530 mmHg at 25° C., about 529 mmHg at 25° C., or another suitable vapor pressure.

The kit may also include a first plurality of protected amino acids. In various embodiments, the protected amino acids of the first plurality of protected amino acids may be coupled to a first protecting moiety. The first protecting moiety may be at least one of a tert-butoxycarbonyl moiety; a 9-fluorenylmethyloxycarbonyl moiety; a trityl moiety; an o-nitrobenzyl moiety; a 2,2,4,6,7-pentamethyldihydrobenzofuran-5-sulfonyl moiety; a 4-methyltrityl moiety; and/or another suitable moiety.

In some embodiments, the kit may further include a second plurality of protected amino acids. The protected amino acids of the second plurality of protected amino acids may be coupled to a second protecting moiety. The second protecting moiety may also be at least one of a tert-butoxycarbonyl moiety; a 9-fluorenylmethyloxycarbonyl moiety; a trityl moiety; an o-nitrobenzyl moiety; a 2,2,4,6,7-pentamethyldihydrobenzofuran-5-sulfonyl moiety; a 4-methyltrityl moiety; and/or another suitable moiety. In various embodiments, the first protecting moiety may be different from the second protecting moiety. In various other embodiments, the first protecting moiety may be the same as the second protecting moiety.

In certain embodiments, the kit may also include a third plurality of protected amino acids, a fourth plurality of protected amino acids, a fifth plurality of protected amino acids, a sixth plurality of protected amino acids, or another suitable number of pluralities of protected amino acids. Furthermore, the protected amino acids of the third plurality of protected amino acids may be coupled to a third protecting moiety, the protected amino acids of the fourth plurality of protected amino acids may be coupled to a fourth protecting moiety, the protected amino acids of the fifth plurality of protected amino acids may be coupled to a fifth protecting moiety, the protected amino acids of the sixth plurality of protected amino acids may be coupled to a sixth protecting moiety, and so on for each of the pluralities of protected amino acids. In various embodiments, each plurality of protected amino acids may include a different protecting moiety (e.g., the third protecting moiety may be different from the fourth protecting moiety, the fourth protecting moiety may be different from the fifth protecting moiety, etc.). In various other embodiments, two or more of the pluralities of protected amino acids may include the same protecting moiety (e.g., the third protecting moiety may be the same as the sixth protecting moiety).

In some embodiments, the kit may further include instructions. For example, the kit may include instructions for performing SPPS by using the kit. The instructions may include the steps of introducing the solution to the solid support such that a plurality of thioesters are generated on the solid support and/or introducing the first plurality of protected amino acids to the plurality of thioesters such that a first portion of the first plurality of protected amino acids is coupled to the solid support. The instructions may further include the steps of introducing the wash buffer to the solid support to remove a second portion of the first plurality of amino acids that are not coupled to the solid support, introducing a de-protecting reagent to the solid support to remove a portion of the first protecting moieties from the first portion of the first plurality of protected amino acids to generate a first plurality of de-protected amino acids, and/or introducing the second plurality of protected amino acids to the solid support such that a portion of the second plurality of protected amino acids is coupled to a portion of the first plurality of de-protected amino acids.

The instructions may also include the step of maintaining the solution at a temperature between about 25° C. and about 80° C., between about 35° C. and about 70° C., between about 45° C. and about 60° C., or another suitable temperature. In some other embodiments, the instructions may be adapted to accommodate a third plurality of amino acids, a fourth plurality of amino acids, a fifth plurality of amino acids, a sixth plurality of amino acids, or another suitable number of pluralities of amino acids.

Another aspect of the disclosure relates to methods of performing SPPS. The methods may include providing a solid support as described above. For example, the method may include providing a resin coupled to a protected linker.

The method may also include introducing a solution as described above (e.g., a solution including a thiol, having a pH of between about 4 and about 7, and a temperature of between about 25° C. and about 80° C.) to the solid support. In some embodiments, introducing the solution to the solid support may generate a plurality of thioesters on the solid support. In some embodiments, the method may include introducing a solution including a selenol.

The method may further include introducing a first plurality of protected amino acids as described above to the solid support. In various embodiments, introduction of the first plurality of protected amino acids to the solid support may couple a first portion of the first plurality of protected amino acids to the solid support. Furthermore, as discussed above the protected amino acids of the first plurality of protected amino acids may be coupled to a first protecting moiety.

In some embodiments, the method may include introducing a wash buffer to the solid support. Introduction of the wash buffer may remove a second portion of the first plurality of protected amino acids that are not coupled to the solid support. Furthermore, the method may include introducing a de-protecting reagent to the first portion of the first plurality of protected amino acids to remove a portion of the first protecting moieties from a portion of the first portion of the first plurality of protected amino acids to generate a first plurality of de-protected amino acids.

The method may also include introducing a second plurality of protected amino acids to the solid support to couple a portion of the second plurality of protected amino acids to a portion of the first plurality of de-protected amino acids. Additionally, the method may be adapted to include introducing a third plurality of protected amino acids, a fourth plurality of protected amino acids, a fifth plurality of protected amino acids, a sixth plurality of protected amino acids, or another suitable number of pluralities of amino acids.

As will be understood by one of ordinary skill in the art, each embodiment disclosed herein can comprise, consist essentially of, or consist of its particular stated element, step, ingredient, or component. As used herein, the transition term "comprise" or "comprises" means, includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Synthesis of MEGA Linked Resin

Rink amide resin (0.30-0.60 mmol/g, 0.25 mmol) was allowed to swell in a reaction vessel in 50:50 (v/v) DMF:DCM for 30 minutes followed by Fmoc-deprotection with 20% piperidine in DMF for 25 minutes. The resin was thoroughly washed by consecutive 30 second DMF, DCM, and DMF flow washes. Bromoacetic acid (2.5 mmol) and diisopropylcarbodiimide (DIC, 2.5 mmol) were dissolved in 4 mL DMF and added to the resin. The mixture was agitated with $N_{2(g)}$ for 45 minutes, then an additional 45 minutes with fresh coupling reagents. The resin was thoroughly washed and dried under vacuum. O-(2-(tritylthio)ethyl)hydroxylamine (see Weller, C. E., et al. ChemBioChem 2014, 15, 1263) (1.75 mmol) was dissolved in 7 mL of 50:50 (v/v) sieve-dried DMSO:DMF, added to the resin in a 20 mL scintillation vial, and shaken for 24-48 hours. The resin was filtered, washed, and dried under vacuum to give MEGA resin.

Example 2—Synthesis of Peptide-MEGA

First amino acid coupling: MEGA resin (0.05 mmol) was swelled in 0.5 mL sieve-dried DMF in a 20 mL scintillation vial. 1-[Bis(dimethylamino)methylene]-1H-1,2,3-triazolo[4,5-b]pyridinium-3-oxid hexafluorophosphate (HATU, 0.49 mmol), Fmoc-amino acid (0.5 mmol), and diisopropylethylamine (DIEA, 0.5 mmol) were dissolved in 2.0 mL dry DMF, added to MEGA resin, and mixed for 24 hours.

Peptide elongation/purification: Standard Fmoc-SPPS protocols were employed to extend the peptide chain (see Carpino, L. A., et al. J. Org. Chem. 1972, 37, 3404). The peptide was cleaved from the resin by mixing with 95:2.5:2.5 (v/v) TFA:$H_2O$:triisopropylsilane (TIS) for 1-2 hours. The crude peptide was precipitated from solution by mixing with 10 volumes of cold diethyl ether and centrifuged for 2 minutes at 3,500 rpm. The supernatant was discarded and the peptide lyophilized. Preparative scale RP-HPLC was used to purify the crude peptide and provide pure peptide-MEGA after lyopholization.

Microwave-assisted Synthesis of MEGA Peptides: The MEGA resin was loaded with the amino acid of choice as described herein for the first amino acid coupling. The pre-loaded MEGA resin was place in a LIBERTY BLUE™ peptide synthesizer (CEM™ Corporation, Matthews, N.C.) and automated peptide synthesis was conducted with 50° C. deprotection steps using a 5% piperazine/0.1 M hydroxybenzotriazole (HOBt) solution in DMF. 50° C. amino acid couplings were used for all coupling steps (see Bacsa, B., et al. Nat. Protoc. 2007, 2, 2222).

Example 3—Peptide Thioesterification, Ligation, and Cyclization

α-Thioesterification: Peptide-MEGA (0.5 µmol) was dissolved in 500 µL thioesterification buffer consisting of sodium 2-mercaptoethanesulfonate (MESNa, 200-400 mM), sodium phosphate ($NaH_2PO_4$, 100 mM), and tris(2-carboxyethyl)phosphine (TCEP, 25-50 mM) at pH 4-6. The reactions were agitated for 24-72 hours at 37-70° C. except where noted in Table 2 (see below). The peptide-MES α-thioester was purified by analytical or semi-preparative scale RP-HPLC.

Ligation: Peptide-MEGA thioesterification was performed as described above. The Cys-peptide, CASW (SEQ ID NO:16) (1.25 µmol), was dissolved in 50 µL $NaH_2PO_4$ (200 mM), TCEP (400 mM) buffer, and added directly to the thioesterification reaction vessel. The solution pH was adjusted to 7.5 by litmus and the reaction mixed for 8-24 hours. The reaction was analyzed by RP-HPLC after reduction of the assay mixture with additional TCEP (25-50 mM final concentration).

Cyclization: N-terminal Cys-peptide (0.5 µmol) was dissolved in MESNa (200-400 mM), $NaH_2PO_4$ (100 mM), and TCEP (25-50 mM) buffer at pH 4-6. Reactions were allowed to proceed for 8-72 hours at 50-70° C. Reaction mixtures were analyzed by C18 analytical RP-HPLC with prior treatment with additional TCEP (25-50 mM final concentration).

Example 4—Synthesis of Cyclized and Oxidized SFT-1(I10G)

The sequence CFPDGRCTKSIPPG-MEGA (SEQ ID NO:25) was prepared on Rink amide resin (0.05 mmol) via automated peptide synthesis as described above. The crude peptide was cleaved from the resin in a 95:2.5:2.5 (v/v) TFA:$H_2O$:TIS solution and precipitated with 10 volumes of cold diethyl ether and lyopholized. The linear peptide was purified by C18 preparative RP-HPLC (15-40% B, 60 minutes) and lyophilized (15.4 mg, 20%).

SFT-1(I10G)-MEGA (SEQ ID NO:25) (5 mg, 3.1 µmol) was cyclized as described above at 70° C. for 24 hours. The cyclic peptide was purified by C18 semi-preparative RP-HPLC (10-50% B, 45 minute gradient) (1.5 mg, 33%).

Cyclic SFT-1(I10G) was oxidized to form the disulfide bridge by incubating the peptide in 100 mM $(NH_4)HCO_3$ at 25° C. overnight (0.2 mg/mL). SFT-1 (I10G) was purified by C18 analytical RP-HPLC (10-50% B, 30 minute gradient) with a quantitative yield.

Example 5—Trypsin Inhibition Assays

The inhibition of bovine trypsin by the Sunflower Trypsin Inhibitor-1 analog, SFT-1(I10G), was measured spectrophotometrically. The hydrolysis of N($\alpha$)-benzoyl-L-arginine 4-nitroanilide (BAPNA) by bovine trypsin to generate the yellow colored 4-nitroaniline was followed at 410 nm in the presence of varying concentrations of SFT-1(I10G) (see Lavens, S. E., et al. J. Immunol. Methods 1993, 166, 93 and Quimbar, P., et al. J. Biol. Chem. 2013, 288, 13885). Briefly, 500 µM BAPNA and 1 nM to 2.5 µM SFT-1(I10G) were incubated for 5 minutes in a 96-well plate in the presence of assay buffer consisting of 50 mM Tris and 20 mM $CaCl_2$ at pH 8.0. BAPNA hydrolysis was initiated by the addition of 100 nM trypsin and the reaction was allowed to proceed for 20 minutes at 27° C. The final $Abs_{410}$ was measured using a BIOTEK® SYNERGY™ 4 microplate reader and plotted in GRAPHPAD PRISM™. All experiments were undertaken in triplicate and the average value reported with error being the standard deviation from the mean.

Example 6—Synthesis of AWKX-MEGA (SEQ ID NO:1) Peptides

The MEGA linker was assembled in two steps prior to peptide synthesis. Briefly, commercially available Rink amide resin was condensed with bromoacetic acid, and the bromoacetylated resin incubated with S-trityl protected 2-(aminooxy)ethanethiol (compound 1) to obtain the MEGA linked resin (see FIG. 2 and Table 1). Compound 1 was synthesized in multi-gram quantities in three high-yielding steps with a single column purification (see Weller, C. E., et al. Chem Bio Chem 2014, 15, 1263). Next, the conditions for coupling the first amino acid to the secondary amine of MEGA were explored. DIC-mediated coupling with the additive ethyl (hydroxyimino)cyanoacetate (Oxyma) sufficed for sterically unhindered amino acids Gly and Ala. Consistent with previously reported conditions for coupling onto secondary amines, coupling reagents such as HATU or bis(trichloromethyl) carbonate (BTC) were used for other amino acids (see Patgiri, A., et al. Org. Biomol. Chem. 2010, 8, 1773). However, this did not result in significant racemization during resin loading, as seen from the high purity of crude peptides released from the resin (see FIGS. 3A-3N).

TABLE 1

Synthesis of AWKX-MEGA (SEQ ID NO: 1) Peptides

| Entry | X | Crude Purity[a] [%] | Isolated Yield[b] [%] | Calcd. MW | Obsd. MW[c] |
|---|---|---|---|---|---|
| 1 | K | 85 | 51 | 664.8 | 664.6 |
| 2 | Q | 85 | 47 | 664.8 | 664.8 |
| 3 | V | 75 | 47 | 635.8 | 635.5 |
| 4 | G | 71 | 45 | 593.7 | 593.4 |
| 5 | A | 77 | 44 | 607.7 | 607.4 |
| 6 | L | 79 | 43 | 649.8 | 649.5 |
| 7 | S | 72 | 42 | 623.7 | 623.6 |
| 8 | F | 89 | 33 | 683.8 | 683.6 |
| 9 | C | 44 | 31 | 639.8 | 639.5 |
| 10 | R | 40 | 20 | 692.9 | 692.5 |
| 11 | T | 79 | 19 | 637.8 | 637.5 |
| 12 | D | 62 | 18 | 651.8 | 651.4 |
| 13 | D-A | 82 | 56 | 607.7 | 607.4 |
| 14 | D-C | 58 | 43 | 639.8 | 639.5 |

[a]Purity of peptide based on RP-HPLC peak integration at 280 nm.
[b]Isolated yield based on 0.05 mmol scale synthesis.
[c]ESI-MS [M + H]+ ion.

Example 7—Assessment of C-Terminal Amino Acid Compatibility

Figure 2:
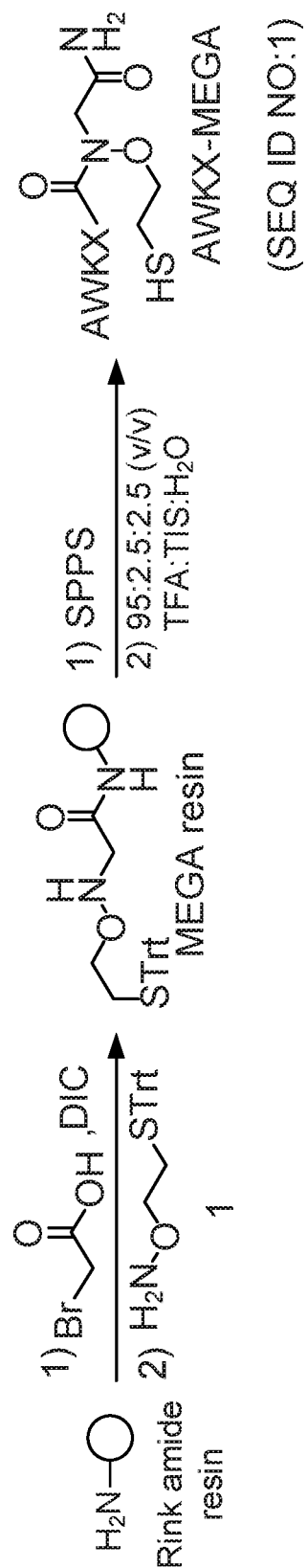
FIG. 2 is a scheme for the synthesis of AWKX-MEGA (SEQ ID NO:1) peptides.
Figure 3A:
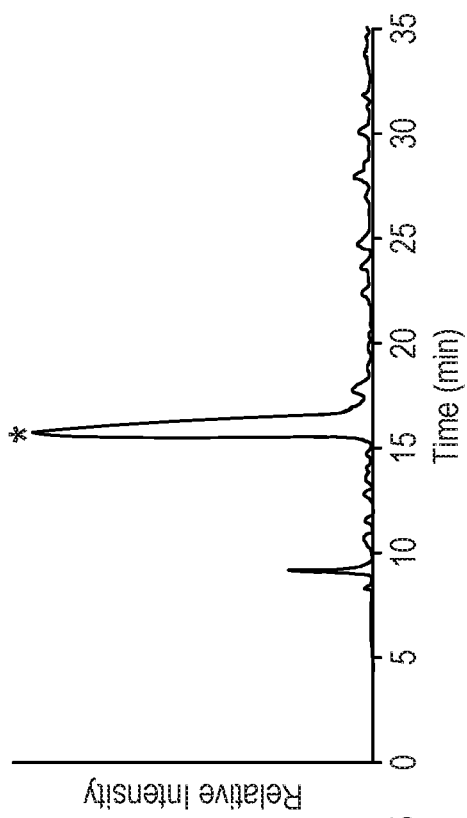
FIG. 3A is an RP-HPLC spectrum of crude AWKG-MEGA (SEQ ID NO:2) peptide after TFA-cleavage from resin.
Figure 3B:
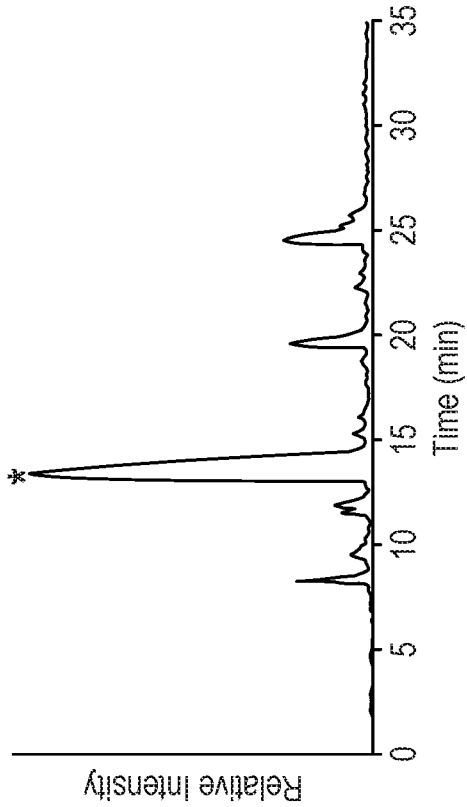
FIG. 3B is an RP-HPLC spectrum of crude AWKA-MEGA (SEQ ID NO:3) peptide after TFA-cleavage from resin.
Figure 3C:
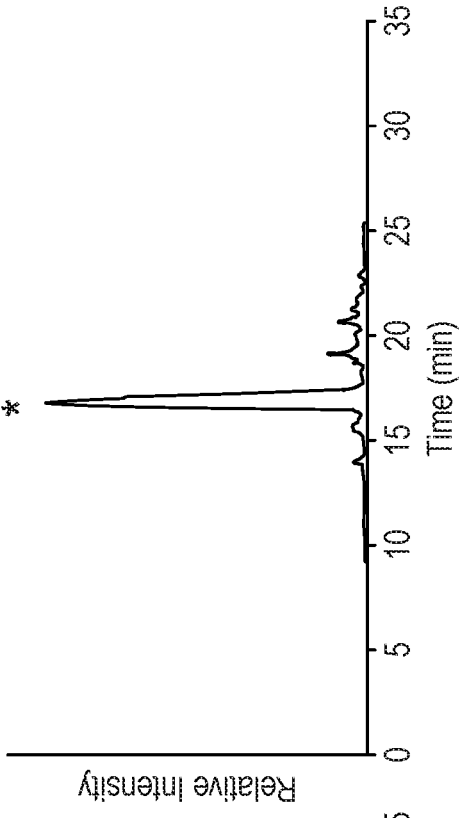
FIG. 3C is an RP-HPLC spectrum of crude AWKL-MEGA (SEQ ID NO:4) peptide after TFA-cleavage from resin.
Figure 3D:
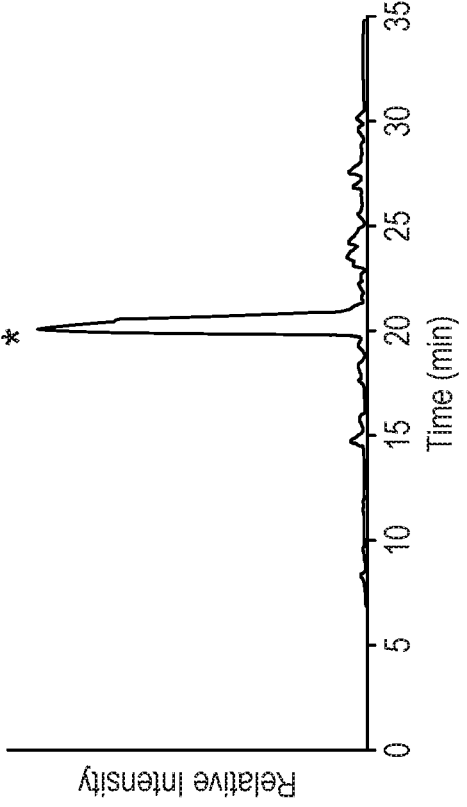
FIG. 3D is an RP-HPLC spectrum of crude AWKV-MEGA (SEQ ID NO:5) peptide after TFA-cleavage from resin.
Figure 3E:
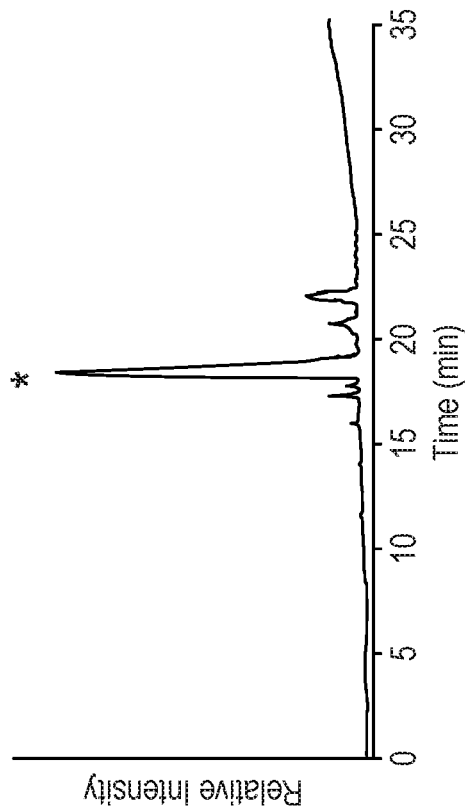
FIG. 3E is an RP-HPLC spectrum of crude AWKD-MEGA (SEQ ID NO:6) peptide after TFA-cleavage from resin.
Figure 3F:
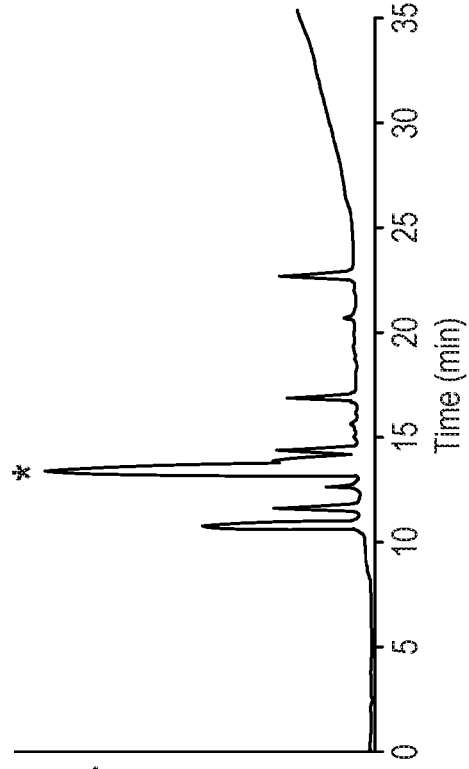
FIG. 3F is an RP-HPLC spectrum of crude AWKF-MEGA (SEQ ID NO:7) peptide after TFA-cleavage from resin.
Figure 3G:
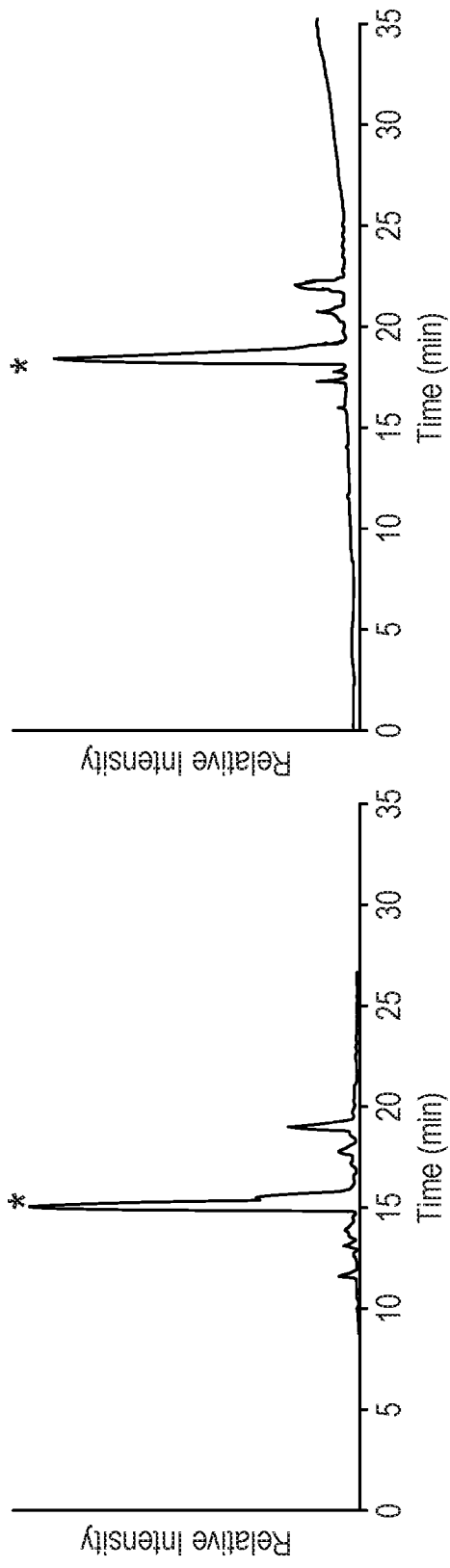
FIG. 3G is an RP-HPLC spectrum of crude AWKQ-MEGA (SEQ ID NO:8) peptide after TFA-cleavage from resin.
Figure 3H:
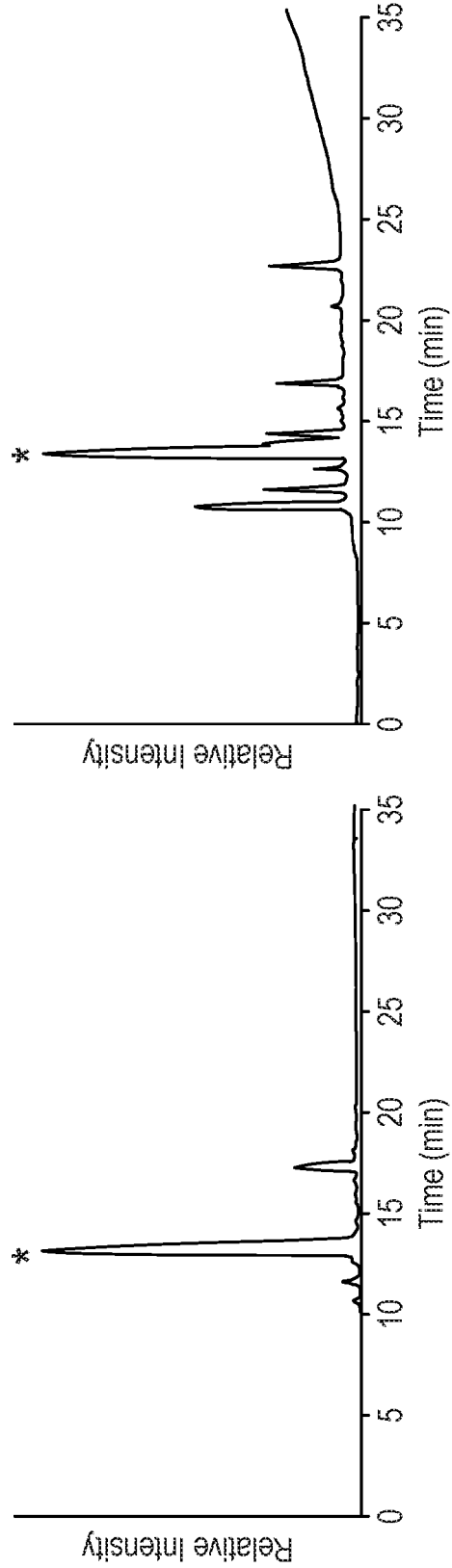
FIG. 3H is an RP-HPLC spectrum of crude AWKR-MEGA (SEQ ID NO:9) peptide after TFA-cleavage from resin.
Figure 3I:
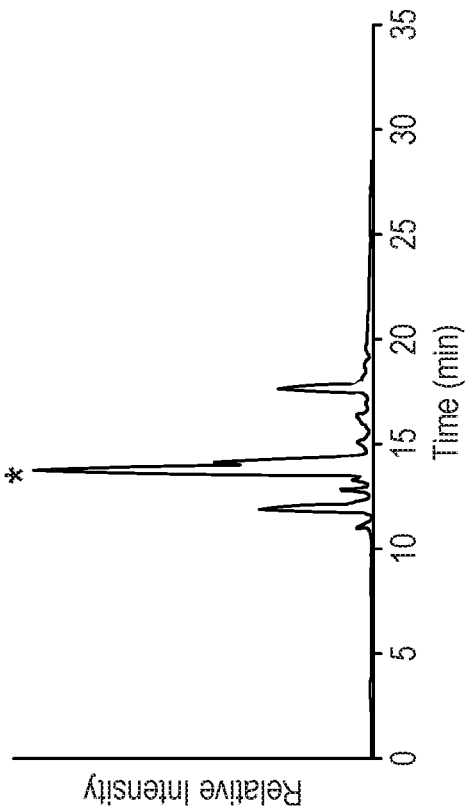
FIG. 3I is an RP-HPLC spectrum of crude AWKS-MEGA (SEQ ID NO:10) peptide after TFA-cleavage from resin.
Figure 3J:
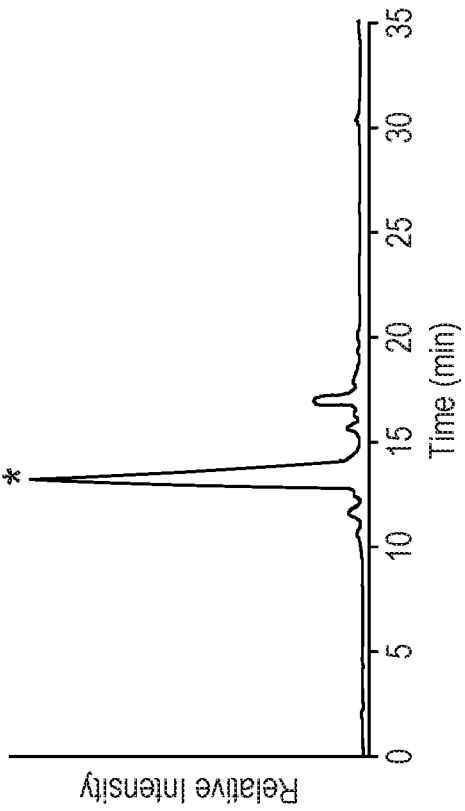
FIG. 3J is an RP-HPLC spectrum of crude AWKT-MEGA (SEQ ID NO:11) peptide after TFA-cleavage from resin.
Figure 3K:
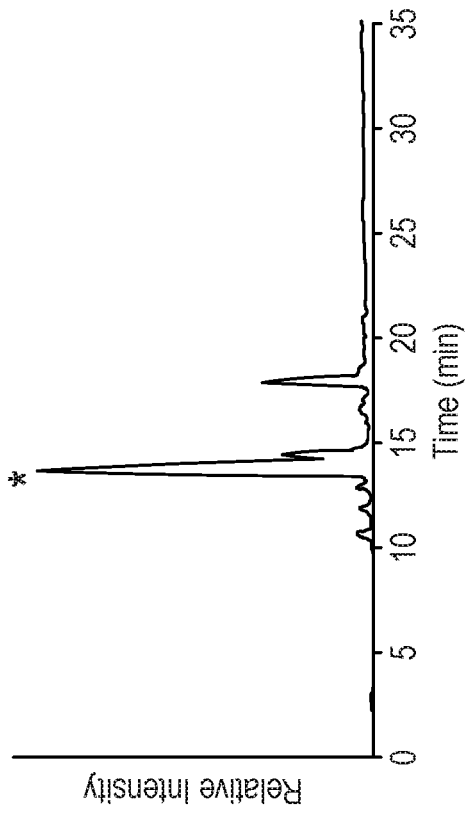
FIG. 3K is an RP-HPLC spectrum of crude AWK(D-A)-MEGA (SEQ ID NO:12) peptide after TFA-cleavage from resin.
Figure 3L:
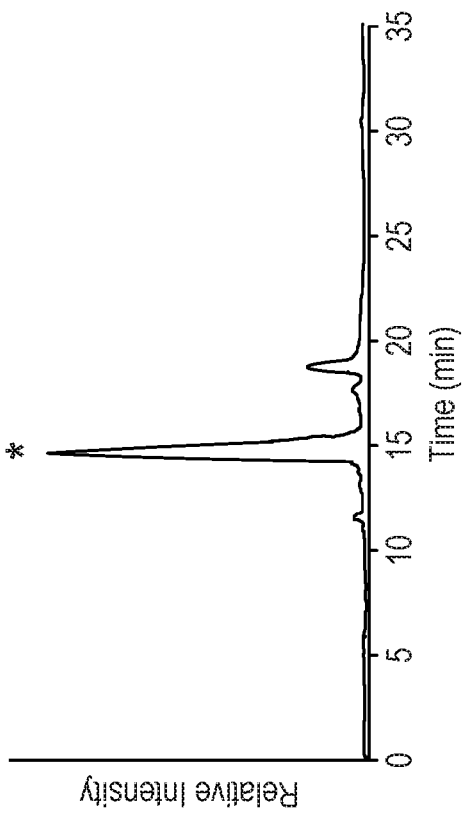
FIG. 3L is an RP-HPLC spectrum of crude AWKK-MEGA (SEQ ID NO:13) peptide after TFA-cleavage from resin.
Figure 3M:
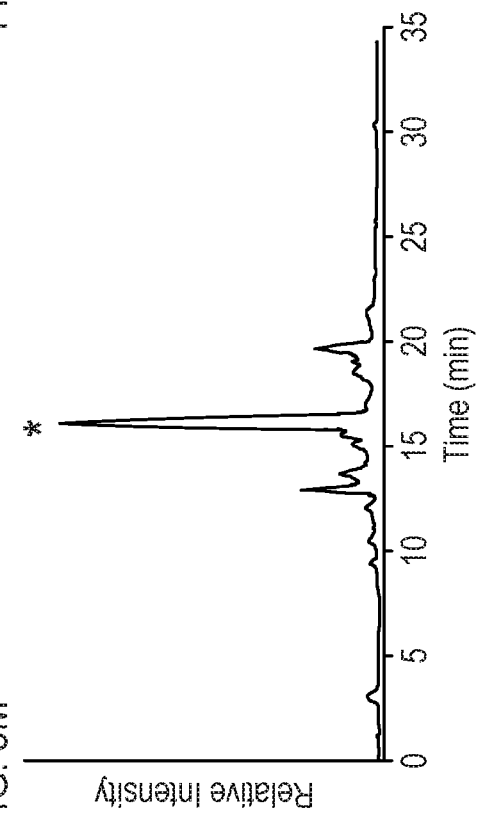
FIG. 3M is an RP-HPLC spectrum of crude AWKC-MEGA (SEQ ID NO:14) peptide after TFA-cleavage from resin.
Figure 3N:
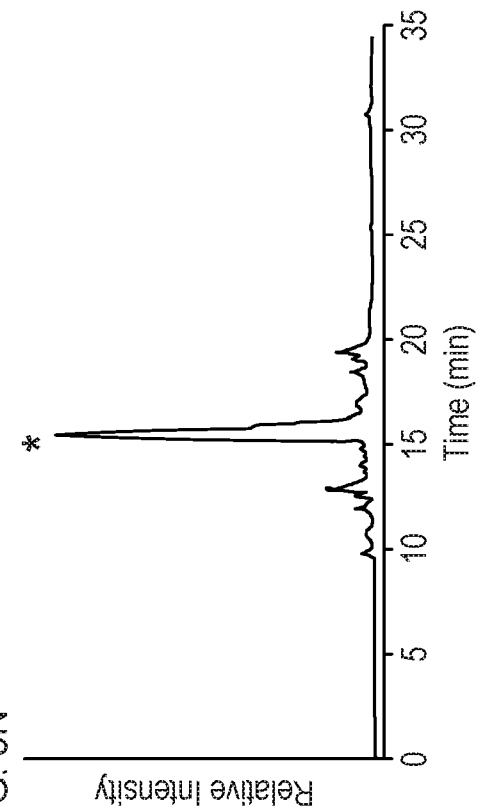
FIG. 3N is an RP-HPLC spectrum of crude AWK(D-C)-MEGA (SEQ ID NO:15) peptide after TFA-cleavage from resin. For FIGS. 3A-3N, RP-HPLC performed on C18 analytical column, 0-73% B, 30 minute gradient. *=AWKX-MEGA (SEQ ID NO:1) peptide.
Figure 4B:
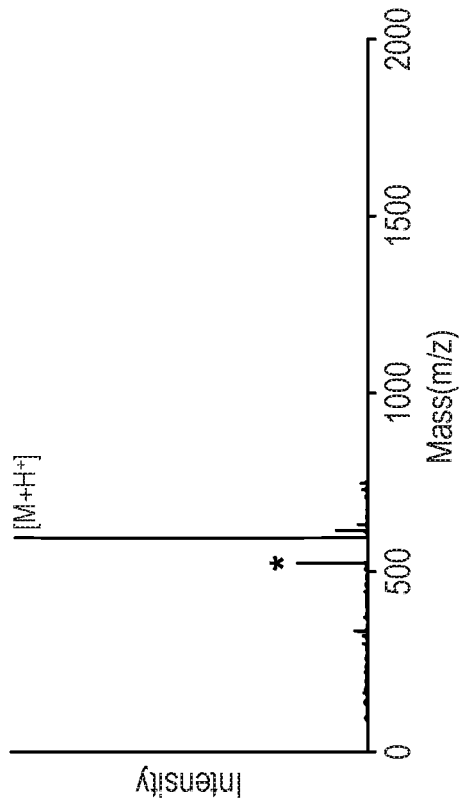
FIG. 4B depicts ESI-MS of purified AWKG-MEGA (SEQ ID NO:2). Calcd. [M+H$^+$] 592.7 Da, obsd. 592.3 Da.
Figure 4D:
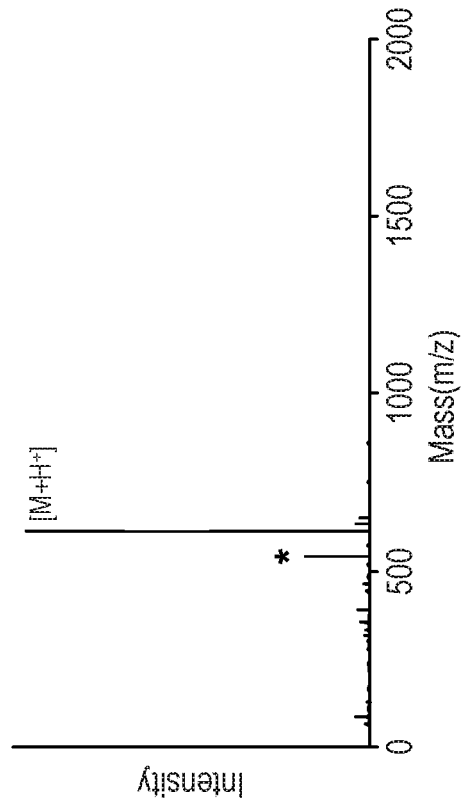
FIG. 4D depicts ESI-MS of purified AWKA-MEGA (SEQ ID NO:3). Calcd. [M+H$^+$] 606.7 Da, obsd. 606.5 Da.
Figure 4A:
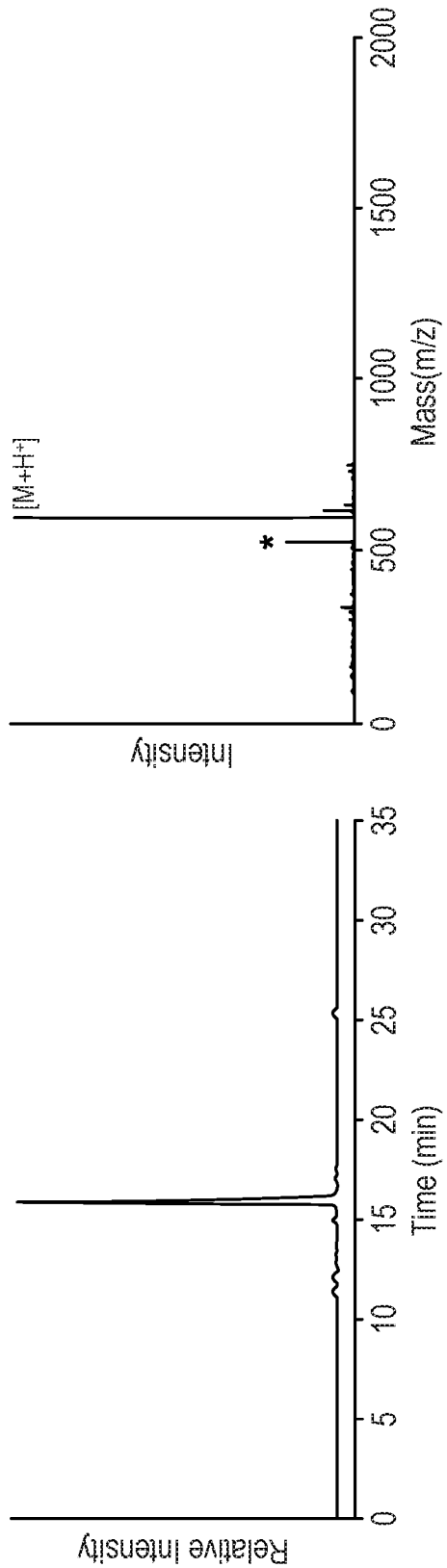
FIG. 4A depicts purified AWKG-MEGA (SEQ ID NO:2).
Figure 4C:
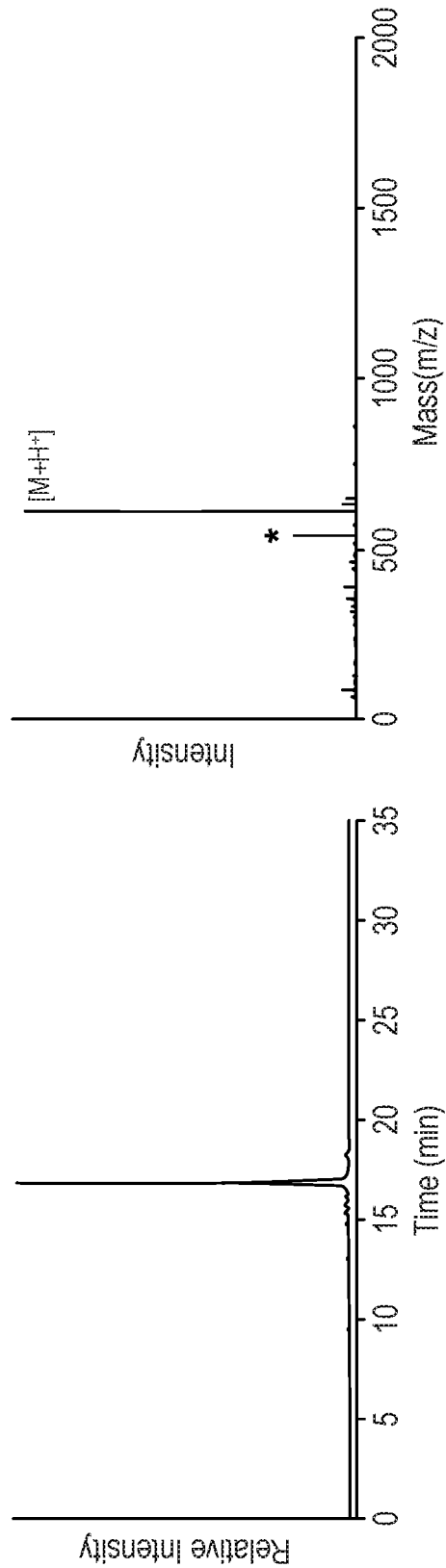
FIG. 4C depicts purified AWKA-MEGA (SEQ ID NO:3).
Figure 4U:
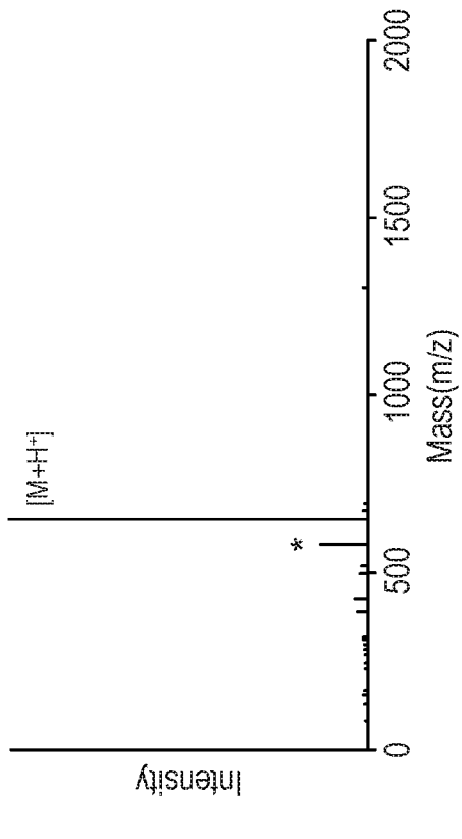
FIG. 4U depicts purified AWKD-MEGA (SEQ ID NO:6).
Figure 4V:
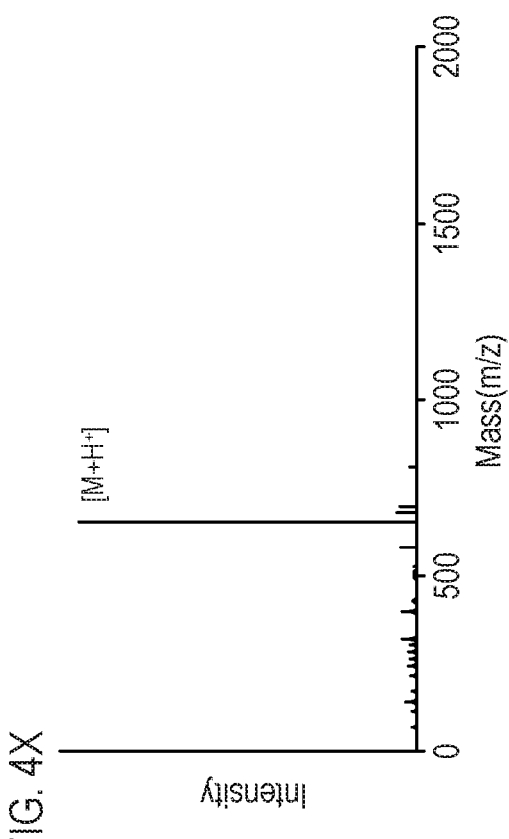
FIG. 4V depicts ESI-MS of purified AWKD-MEGA (SEQ ID NO:6). Calcd. [M+H$^+$] 650.8 Da, obsd. 650.4 Da.
Figure 4W:
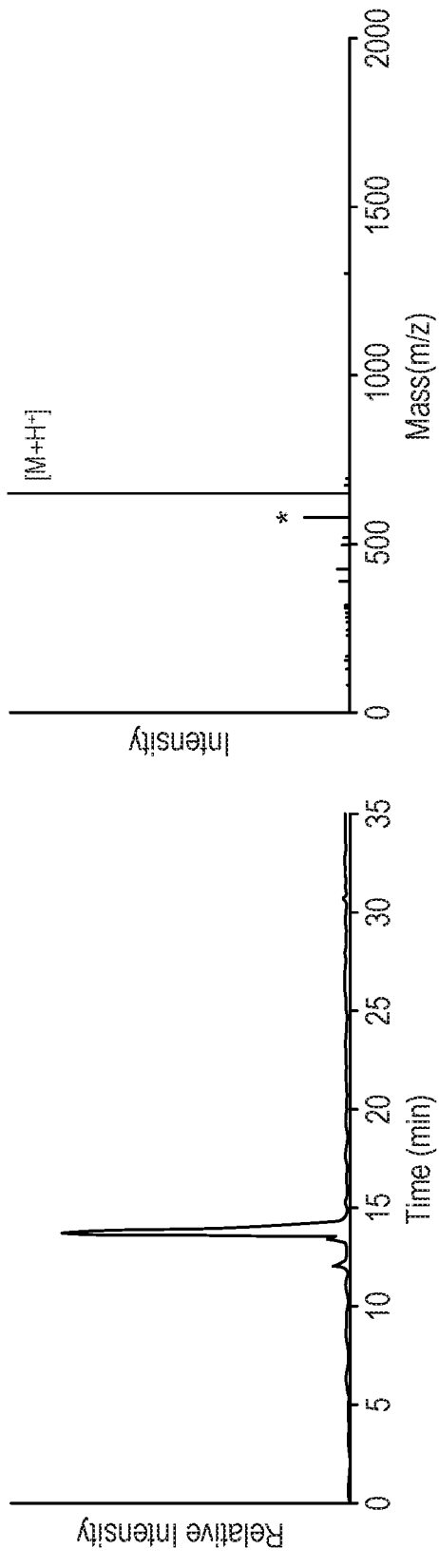
FIG. 4W depicts purified AWKK-MEGA (SEQ ID NO:13).
Figure 4X:
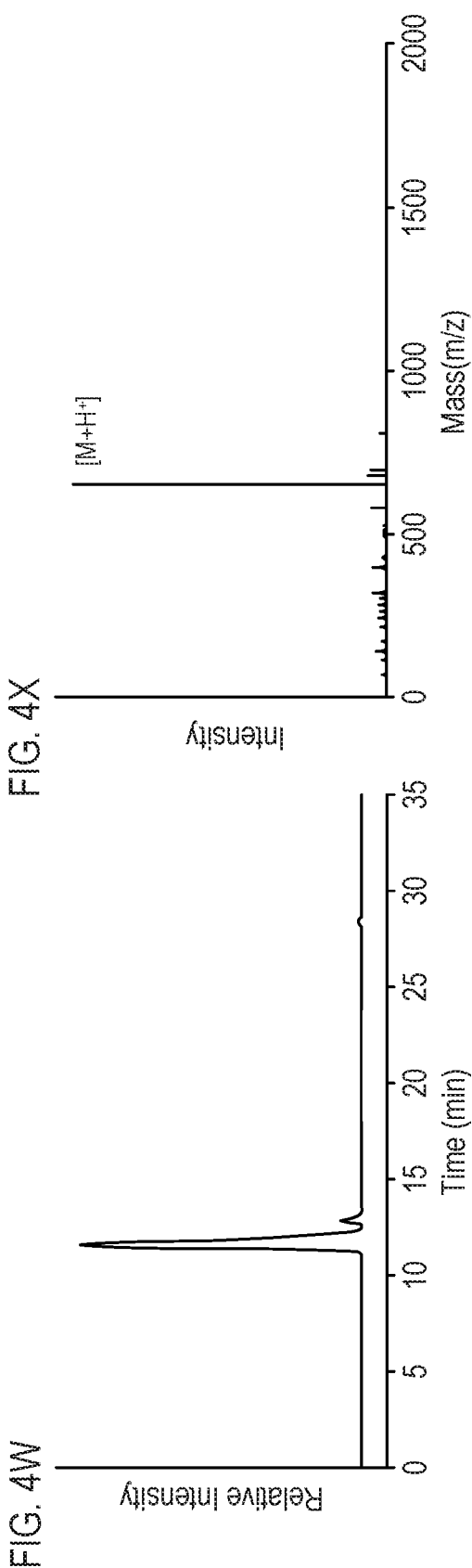
FIG. 4X depicts ESI-MS of purified AWKK-MEGA (SEQ ID NO:13). Calcd. [M+H$^+$] 664.8 Da, obsd. 664.6 Da.
Figure 4Y:
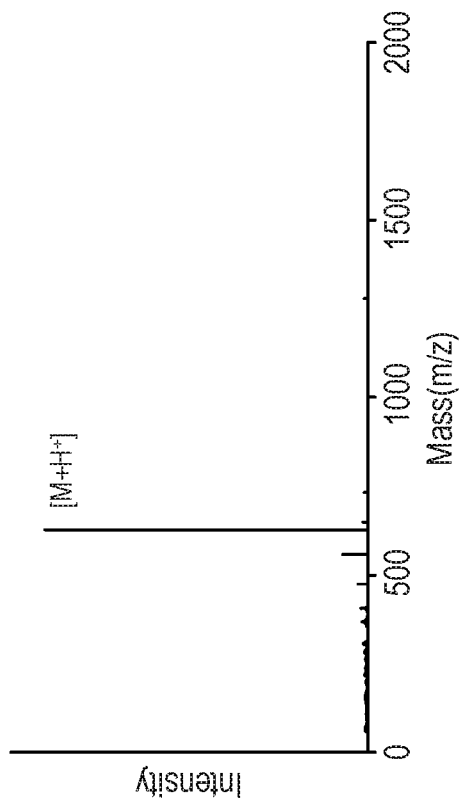
FIG. 4Y depicts purified AWKC-MEGA (SEQ ID NO:14).
Figure 4Z:
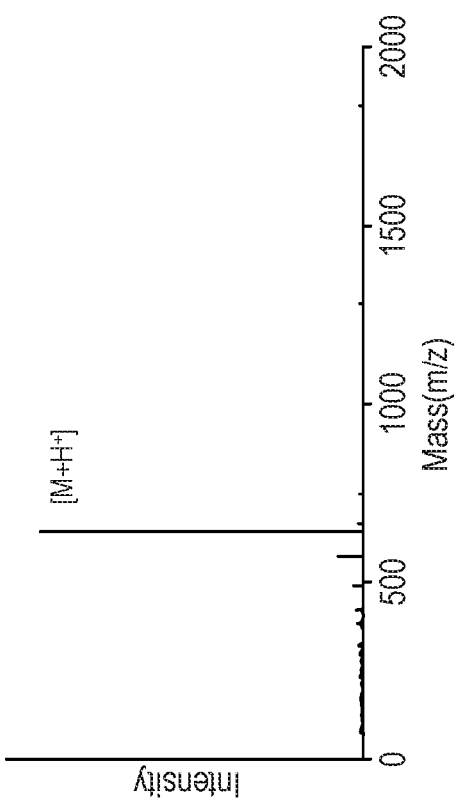
FIG. 4Z depicts ESI-MS of purified AWKC-MEGA (SEQ ID NO:14). Calcd. [M+H$^+$] 639.8 Da, obsd. 639.5 Da.
Figure 4A:
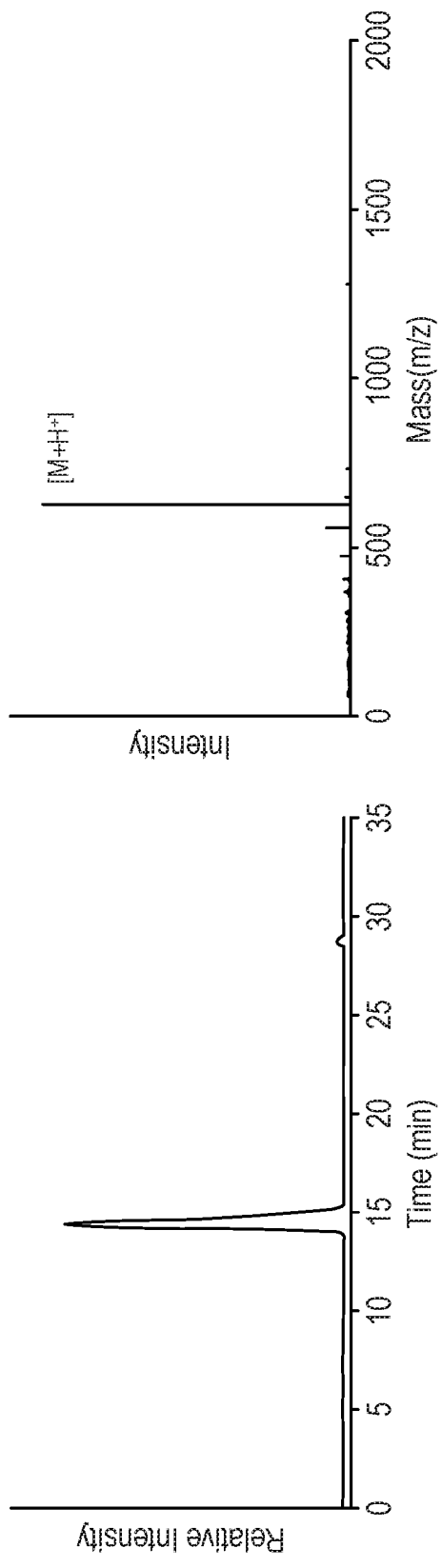
Figure 4B:
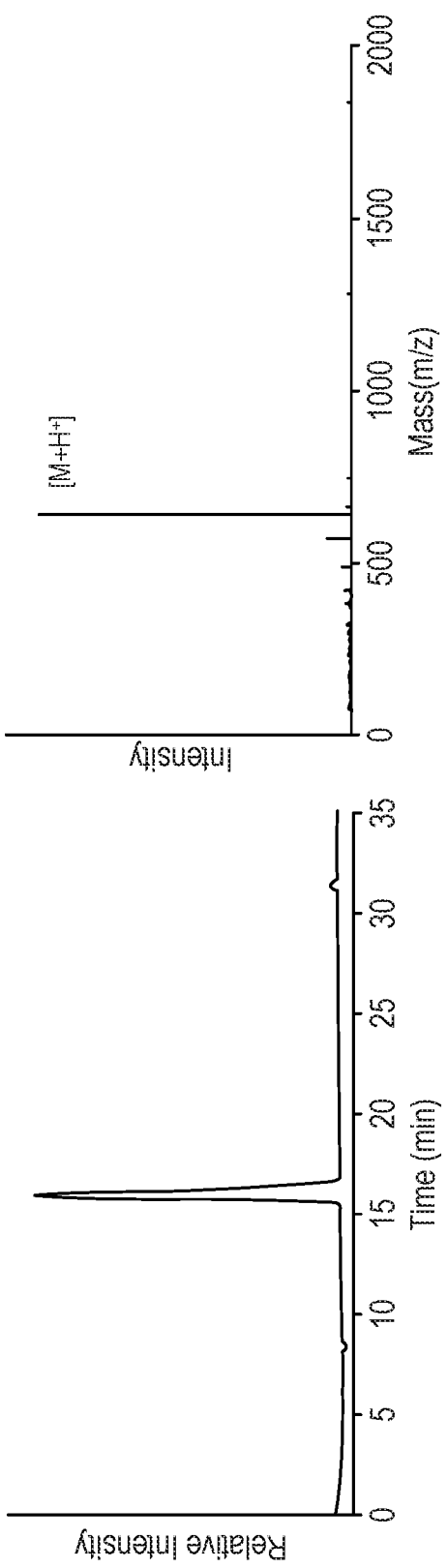
Figure 5:
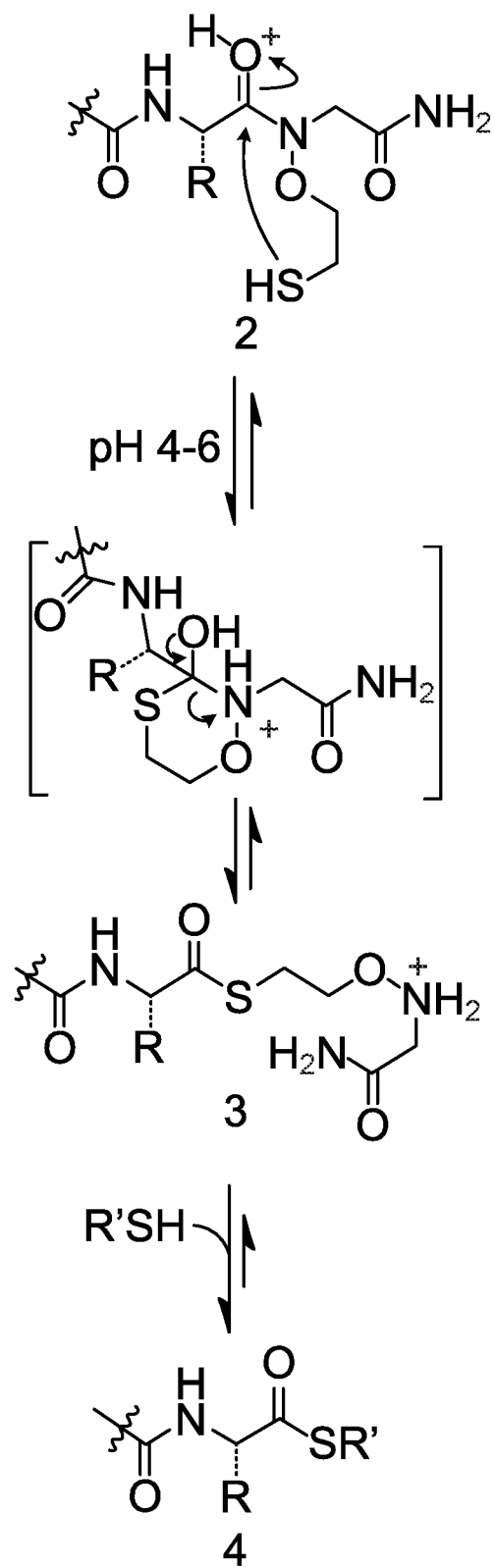
FIG. 5 is a proposed mechanism of thioester formation from peptide-MEGA.
Figure 6A:
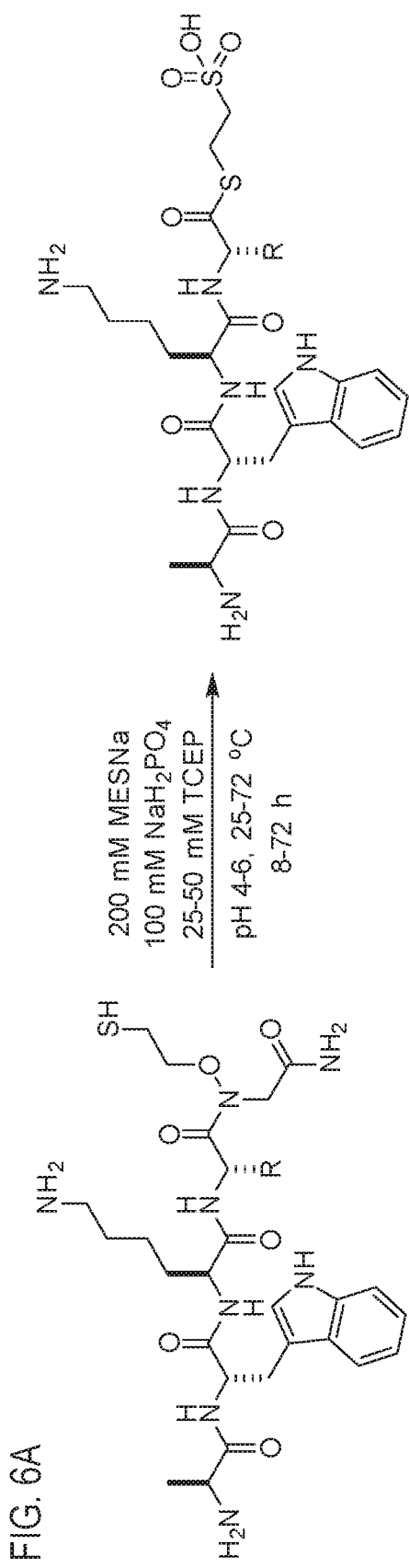
FIG. 6A is a general scheme for peptide-MEGA thioesterification.
Figure 6B:
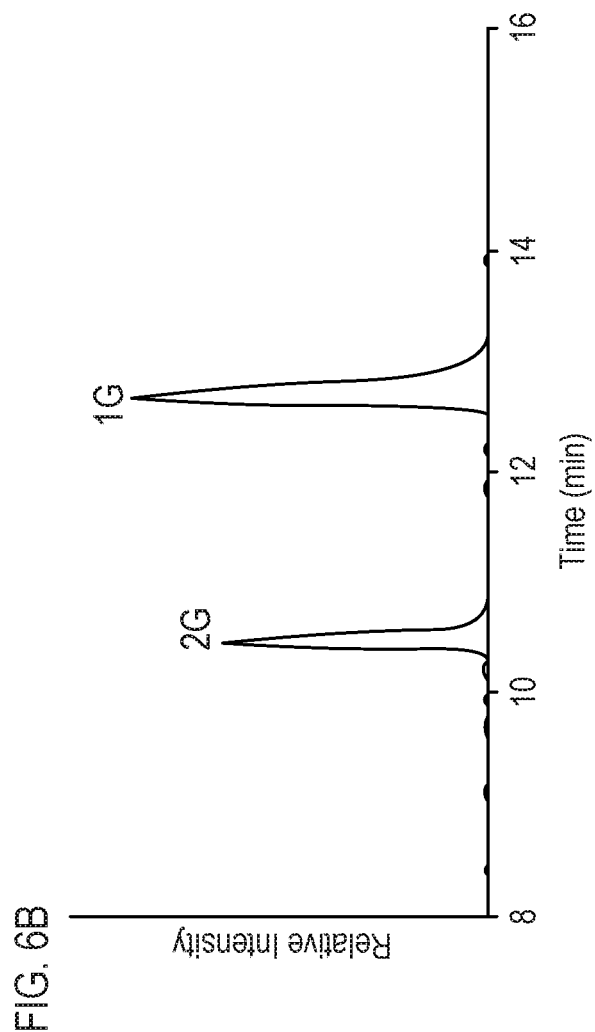
FIG. 6B depicts AWKG-MEGA (SEQ ID NO:2) thioesterification, 200 mM MESNa, pH 5.6, 25° C.

After coupling the first amino acid, a series of 4-mer peptides with the sequence AWKX-MEGA (SEQ ID NO:1) was synthesized to assess the C-terminal amino acid compatibility of MEGA (see FIGS. 2 and 4A-4BB and Table 1). Acidolytic cleavage from the resin and purification by RP-HPLC yielded good quantities of 14 different AWKX-MEGA (SEQ ID NO:1) peptides. Furthermore, the high purity of each crude peptide indicated that the N—O bond was stable throughout manual peptide synthesis and cleavage from the solid support (see FIGS. 2 and 3A-3N and Table 1). AWKX-MEGA (SEQ ID NO:1) peptides were subsequently tested for the production of isolable $\alpha$-thioesters. It was envisioned that thioester formation from the N-oxyamide 2 (see FIG. 5) may proceed by an N-to-S acyl shift to form the rearranged thioester 3. Collapse of the tetrahedral intermediate provides the initial thioester 3 and addition of an excess of external thiol promotes thiol exchange to generate a stable, isolable thioester 4 (see FIG. 5). Although thioesterification proceeds through a 6-membered cyclic intermediate, rather than the 5-membered intermediate for N-alkylated Cys (see Erlich, L. A., et al. Org. Biomol. Chem. 2010, 8, 2392) or bis-sulfanylethylamide-based strategies (see Ollivier, N., et al. Org. Lett. 2010, 12, 5238), the good aminooxy leaving group enabled thioesterification at mildly acidic pH and room temperature for the AWKG-MEGA (SEQ ID NO:2) peptide (see FIGS. 6A and 6B). This is in contrast with pH ~1 used for thioesterification from N-alkylated Cys (see Erlich, L. A., et al. Org. Biomol. Chem. 2010, 8, 2392).

Example 8—Optimization of Thioesterification Conditions

Figure 8A:
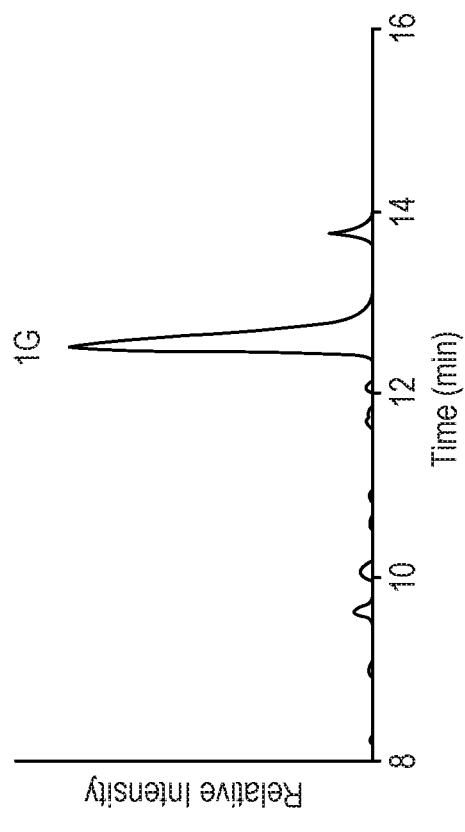
FIG. 8A depicts AWKG-MEGA (SEQ ID NO:2) thioesterification, 200 mM 2,2,2-trifluoroethanethiol, pH 5.6, 25° C.
Figure 8C:
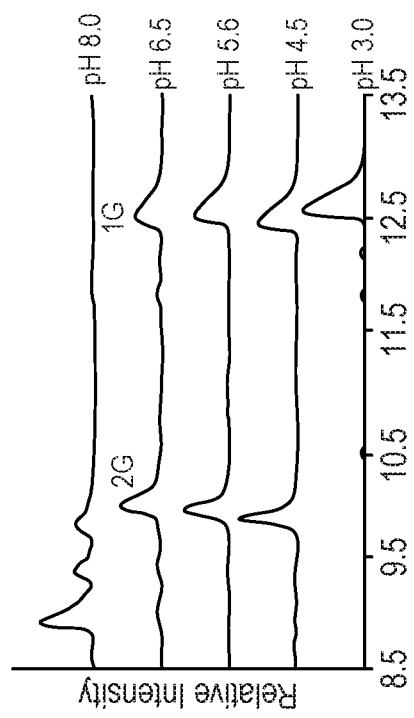
FIG. 8C depicts 24 hour time-points of AWKG-MEGA (SEQ ID NO:2) thioesterification with MESNa at varying pH and 25° C.
Figure 8B:
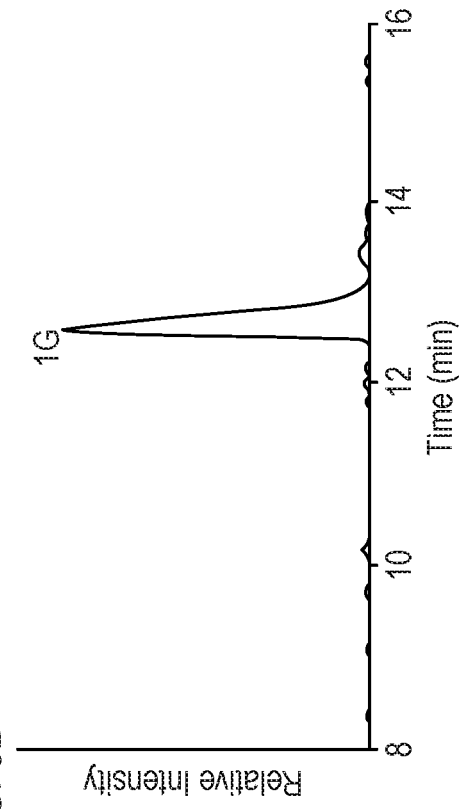
FIG. 8B depicts AWKG-MEGA (SEQ ID NO:2) thioesterification, 200 mM 3-mercaptopropionic acid, pH 5.6, 25° C.

Thioesterification conditions were further optimized for various AWKX-MEGA (SEQ ID NO:1) peptides. It was observed that the nature of the C-terminal amino acid, thiol nucleophile, pH, and reaction temperature significantly influenced thioester yields (see FIGS. 7A-7C and Table 2). Transthioesterification was particularly sensitive to the external thiol employed. While the sodium salt of 2-mercaptoethanesulfonic acid (MESNa) led to the highest yields for all amino acids tested, other commonly employed thiols such as 3-mercaptopropionic acid and 2,2,2-trifluoroethanethiol did not yield significant quantities of the corresponding $\alpha$-thioesters (see FIGS. 8A and 8B).

Figure 9A:
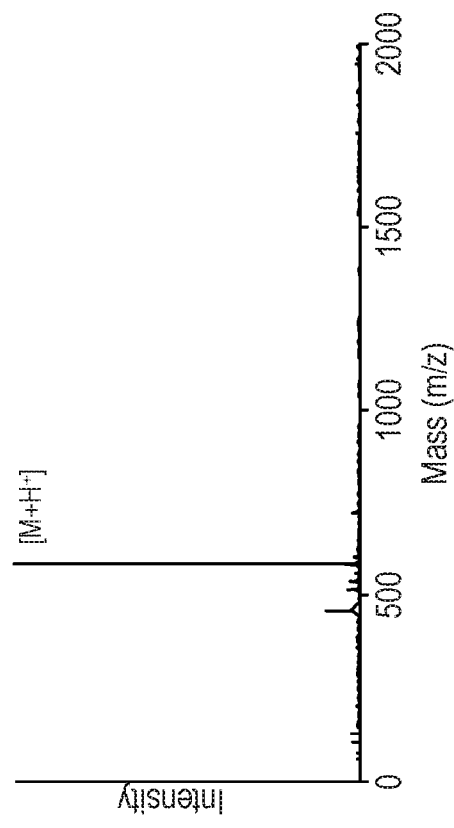
FIG. 9A depicts an AWKG-MEGA (SEQ ID NO:2) thioesterification time-course.
Figure 9B:
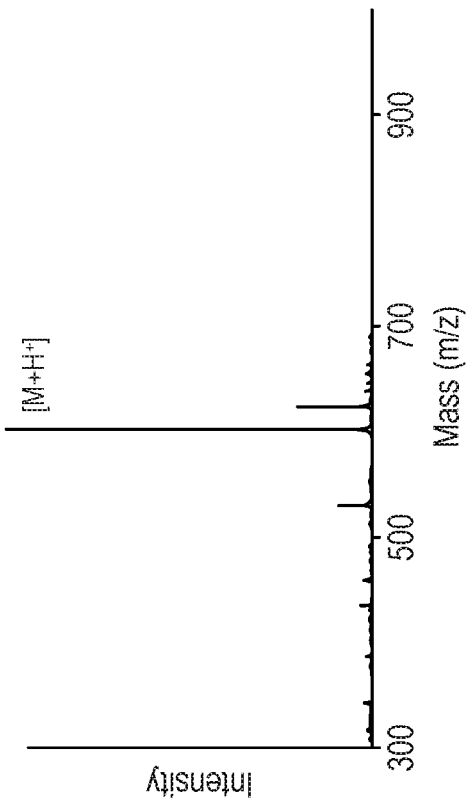
FIG. 9B depicts ESI-MS of AWKG-MES (SEQ ID NO:2) thioester. Calcd. [M+H$^+$] 584.7 Da, obsd. 584.1 Da.
Figure 9C:
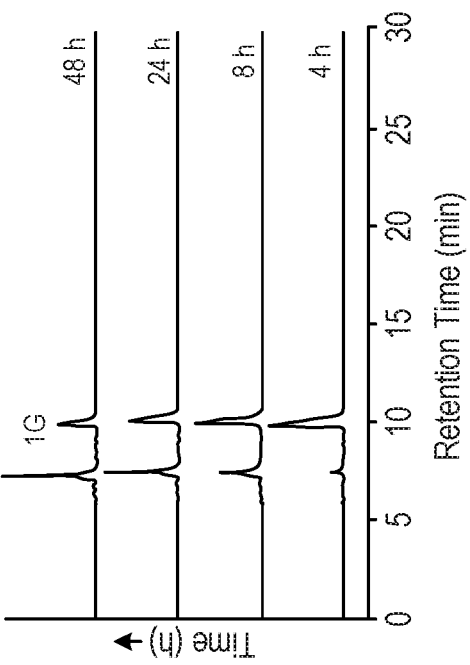
FIG. 9C depicts an AWKA-MEGA (SEQ ID NO:3) thioesterification time-course.
Figure 9D:
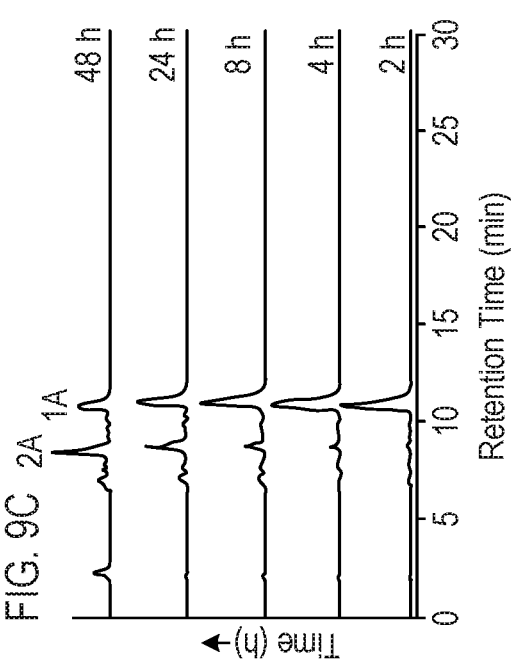
FIG. 9D depicts ESI-MS of AWKA-MES (SEQ ID NO:3) thioester. Calcd. [M+H$^+$] 598.7 Da, obsd. 598.3 Da.
Figure 9E:
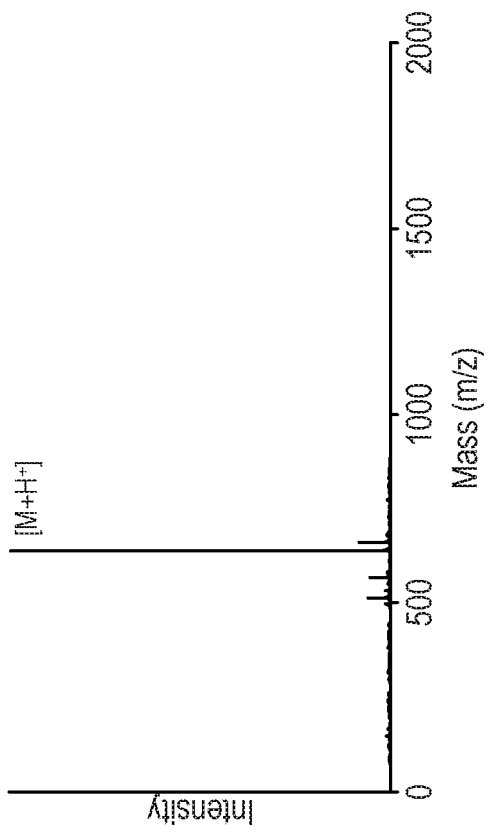
FIG. 9E depicts an AWKL-MEGA (SEQ ID NO:4) thioesterification time-course.
Figure 9F:
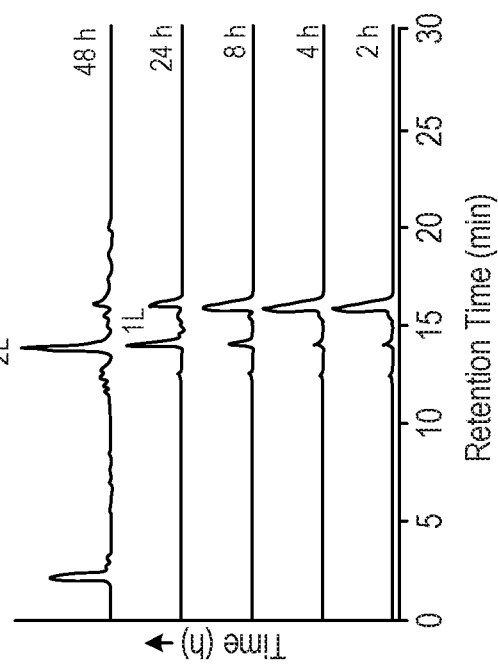
FIG. 9F depicts ESI-MS of AWKL-MES (SEQ ID NO:4) thioester. Calcd. [M+H$^+$] 640.8 Da, obsd. 640.4 Da.
Figure 9G:
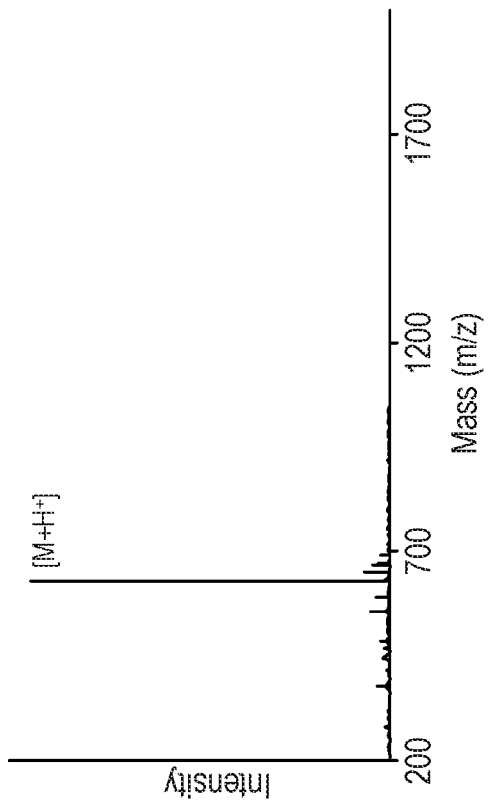
FIG. 9G depicts an AWKV-MEGA (SEQ ID NO:5) thioesterification time-course.
Figure 9H:
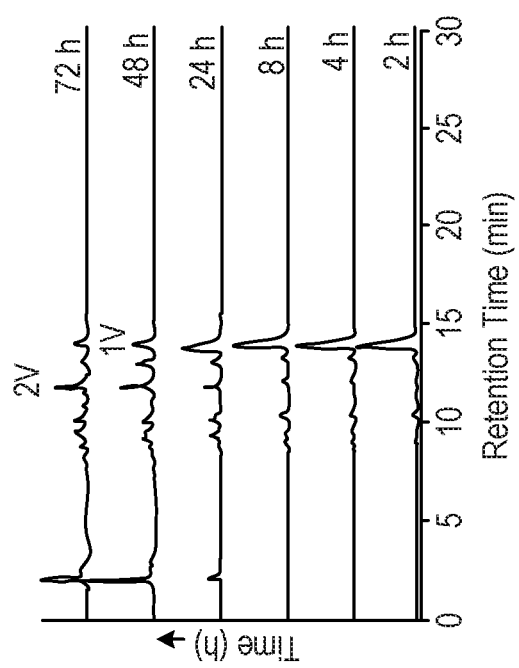
FIG. 9H depicts ESI-MS of AWKV-MES (SEQ ID NO:5) thioester. Calcd. [M+H$^+$] 626.8 Da, obsd. 626.4 Da.
Figure 9M:
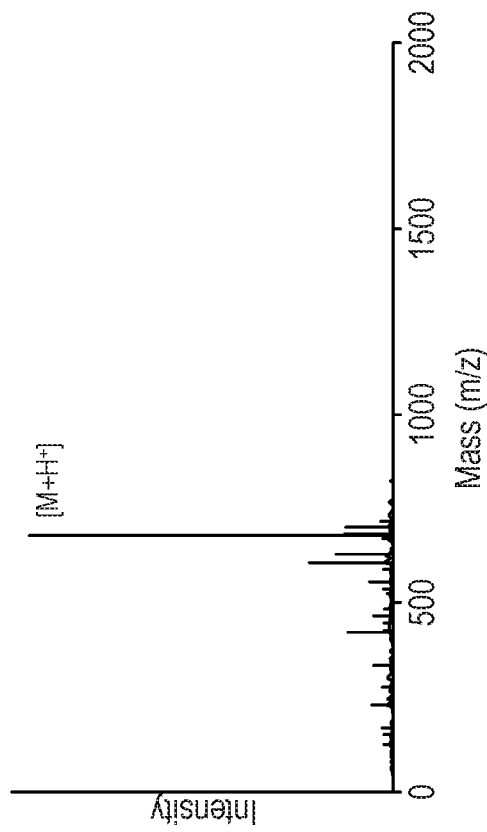
FIG. 9M depicts an AWKR-MEGA (SEQ ID NO:9) thioesterification time-course.
Figure 9O:
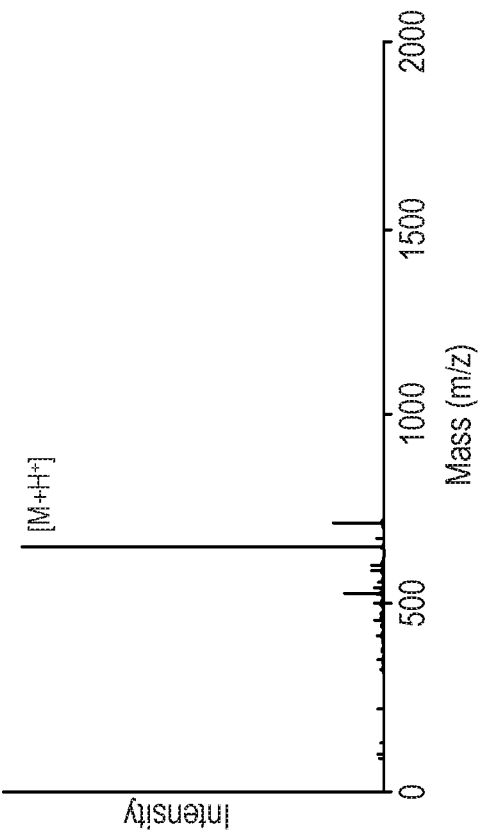
FIG. 9O depicts an AWKQ-MEGA (SEQ ID NO:8) thioesterification time-course.
Figure 9N:
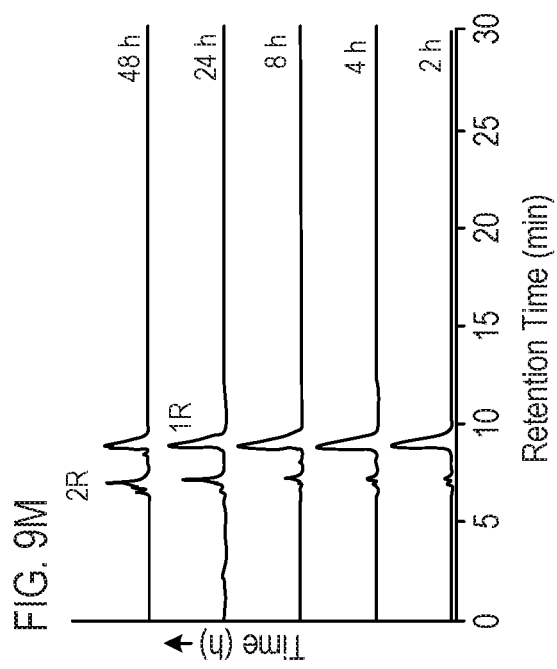
FIG. 9N depicts ESI-MS of AWKR-MES (SEQ ID NO:9) thioester. Calcd. [M+H⁺] 683.8 Da, obsd. 683.5 Da.
Figure 9P:
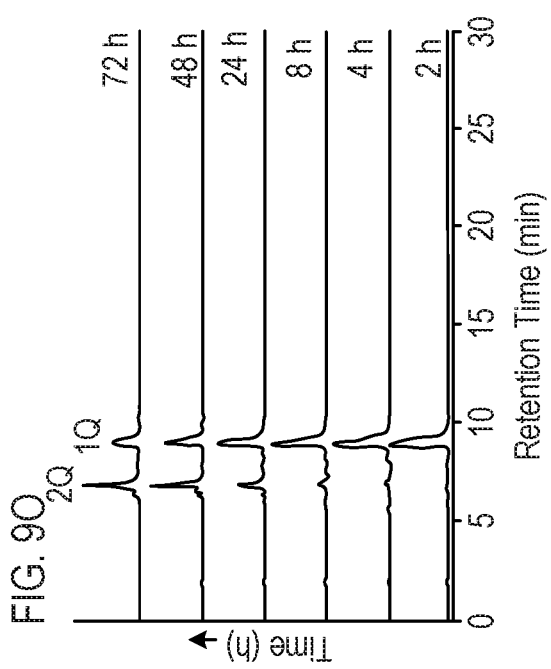
FIG. 9P depicts ESI-MS of AWKQ-MES (SEQ ID NO:8) thioester. Calcd. [M+H⁺] 655.8 Da, obsd. 655.3 Da.
Figure 9R:
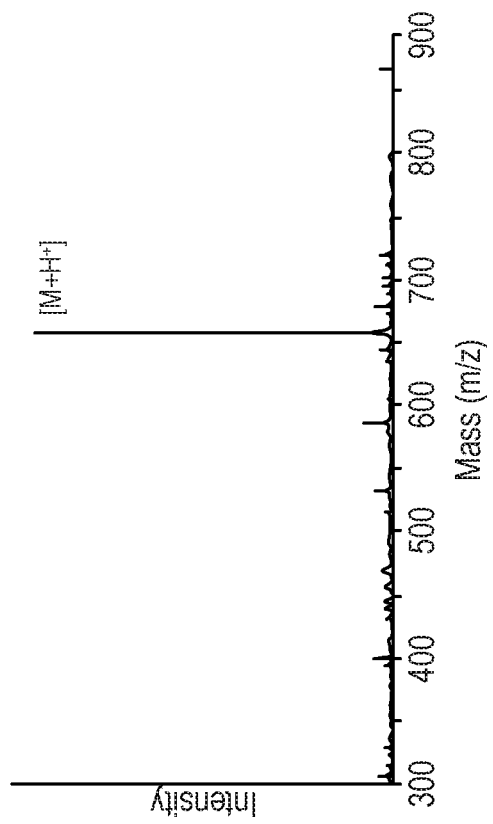
FIG. 9R depicts ESI-MS of AWKK-MES (SEQ ID NO:13) thioester. Calcd. [M+H⁺] 656.8 Da, obsd. 656.8 Da.
Figure 9T:
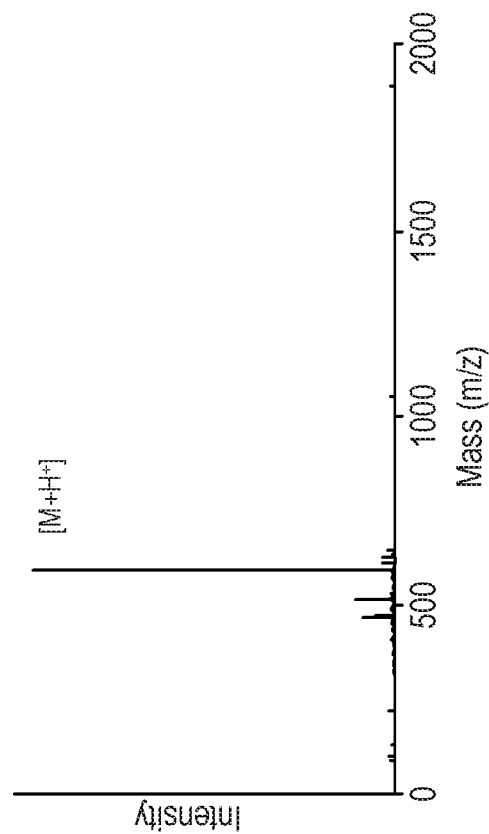
FIG. 9T depicts ESI-MS of AWK(D-A)-MES (SEQ ID NO:12) thioester. Calcd. [M+H⁺] 599.7 Da, obsd. 599.8 Da.
Figure 9Q:
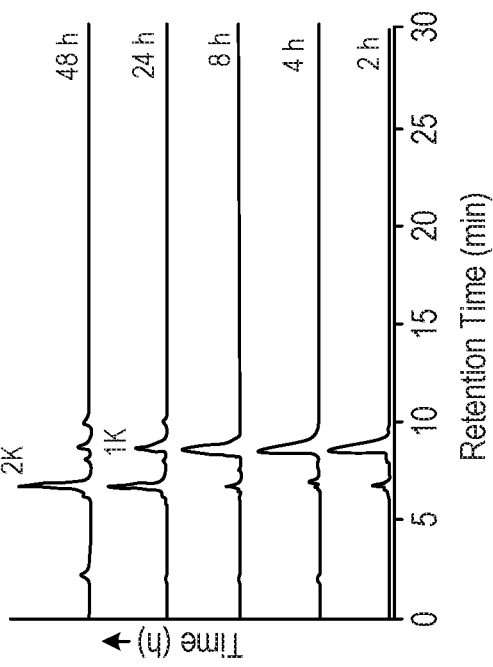
FIG. 9Q depicts an AWKK-MEGA (SEQ ID NO:13) thioesterification time-course.
Figure 9S:
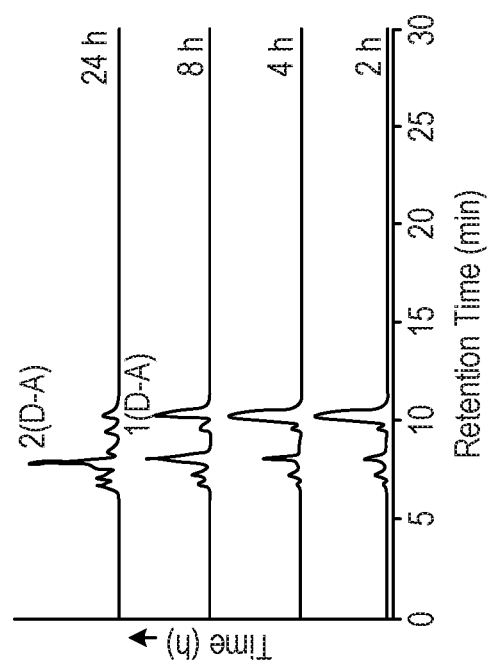
FIG. 9S depicts an AWK(D-A)-MEGA (SEQ ID NO:12) thioesterification time-course.
Figure 9Z:
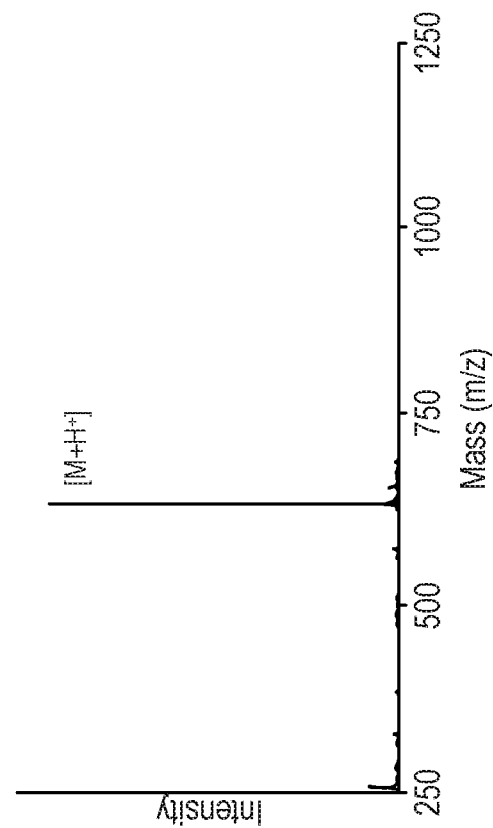
FIG. 9Z depicts ESI-MS of AWK(D-C)-MES (SEQ ID NO:15) thioester. Calcd. [M+H⁺] 631.8 Da, obsd. 631.1 Da. For FIGS. 9A-9Z, 1=AWKX-MEGA (SEQ ID NO:1) and 2=AWKX-MES (SEQ ID NO:1) thioester. RP-HPLC performed on C18 analytical column, 10-60% B, 30 minute gradient.
Figure 9Y:
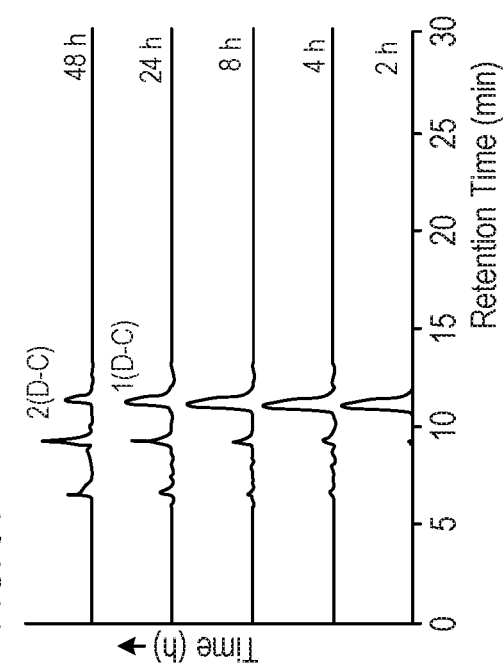
FIG. 9Y depicts an AWK(D-C)-MEGA (SEQ ID NO:15) thioesterification time-course.
Figure 10:
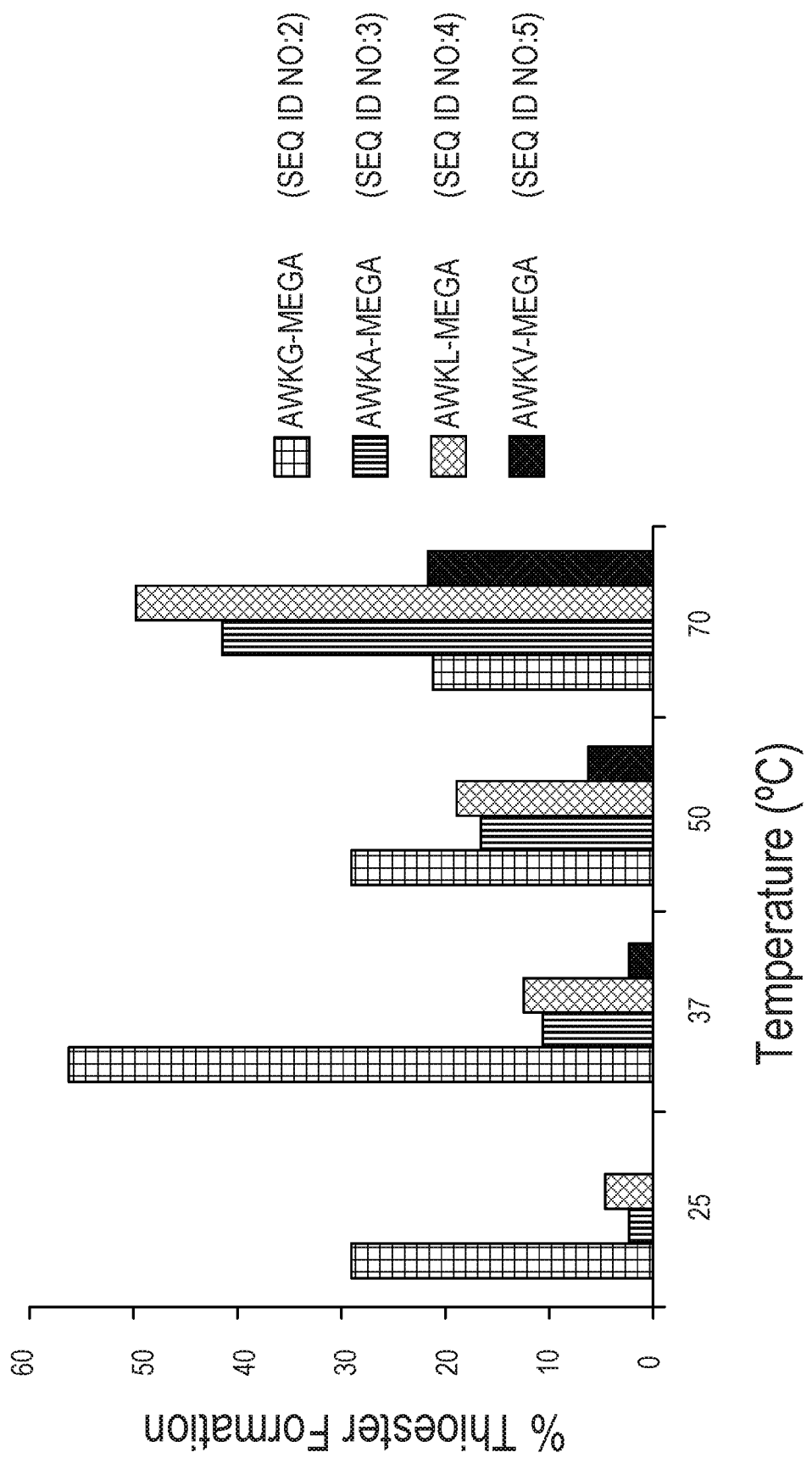
FIG. 10 is a histogram depicting the temperature-dependence of AWKX-MEGA (SEQ ID NO:1) thioesterification. The histogram shows the percentage of AWKX-MES (SEQ ID NO:1) thioester formed at 24 hours under optimized temperatures and pH 5.6 for the given AWKX-MEGA (SEQ ID NO:1) peptides. Percent thioester formation was determined by RP-HPLC peak integration at 280 nm.

Thioesterification yields were best under mildly acidic conditions (pH 4.0-6.0), and no reaction was observed at pH<4. Mildly basic reaction conditions, pH 7.0-8.0, yielded a mixture of thioester and hydrolyzed products at elevated temperatures (see FIG. 8C). Consistent with previous reports with N-alkylated Cys (see Erlich, L. A., et al. Org. Biomol. Chem. 2010, 8, 2392), AWKX-MEGA (SEQ ID NO:1) peptides exhibited slow thioesterification kinetics at room temperature when X was not Gly. However, elevated temperatures improved yields for all peptide thioesters (see Table 2 and FIGS. 9A-9Z). Even for the AWKG-MEGA (SEQ ID NO:2) peptide, increasing the reaction temperature from 25° C. to 37° C. led to a concomitant increase in thioester yield from 29% to 60% (see FIG. 10).

Steric hindrance in β-branched C-terminal amino acids generally reduces reaction rates during NCL (see Hackeng, T. M., et al. Proc. Natl. Acad. Sci. U.S.A. 1999, 96, 10068). Hence, AWKV-MEGA (SEQ ID NO:5) and AWKT-MEGA (SEQ ID NO:11) were tested in thioesterification reactions. While Val produced only a modest 26% yield, Thr generated significantly more of the corresponding α-thioester (see Table 2, entries 8 and 14). Without being bound by any one particular theory, hydrogen bonding with the hydroxyl group of Thr may limit conformational freedom in the MEGA side-chain and enhance its reactivity. The lack of hydrogen bonding with the Val side-chain can preclude such conformational stabilization and can result in lower yields. Overall, β-branching in the C-terminal amino acid proved a greater hindrance toward thioesterification than absolute bulk of the side-chain, as seen by the good yields for AWKF (SEQ ID NO:7) and AWKL (SEQ ID NO:4) thioesters in comparison with AWKV (SEQ ID NO:5) (see Table 2, entries 1, 3, and 14).

TABLE 2

Optimized Thioesterification Conditions for AWKX-MEGA (SEQ ID NO: 1) Peptides

| Entry | X | Temperature (° C.) | pH | Reaction Time (h) | Yield (%)[a] |
|---|---|---|---|---|---|
| 1 | L | 70 | 4.5 | 48 | 67.8 |
| 2 | K | 70 | 4.5 | 48 | 67.5 |
| 3 | F | 70 | 4.5 | 48 | 65.8 |
| 4 | G | 37 | 5.6 | 72 | 60.5 |
| 5 | D-A | 70 | 5.6 | 24 | 57.1 |
| 6 | Q | 50 | 4.5 | 72 | 48.8 |
| 7 | A | 70 | 5.6 | 24 | 45.2 |
| 8 | T | 70 | 4.5 | 48 | 43.1 |
| 9 | S | 50 | 4.5 | 48 | 42.8 |
| 10 | R | 70 | 5.6 | 72 | 41.1 |
| 11 | D-C | 50 | 4.5 | 48 | 38.3 |
| 12 | D | 50 | 5.6 | 8 | 32.5 |
| 13 | C | 50 | 4.5 | 48 | 32.5 |
| 14 | V | 70 | 5.6 | 72 | 26.3 |

[a]Based on RP-HPLC peak integration at 280 nm.

Figure 11:
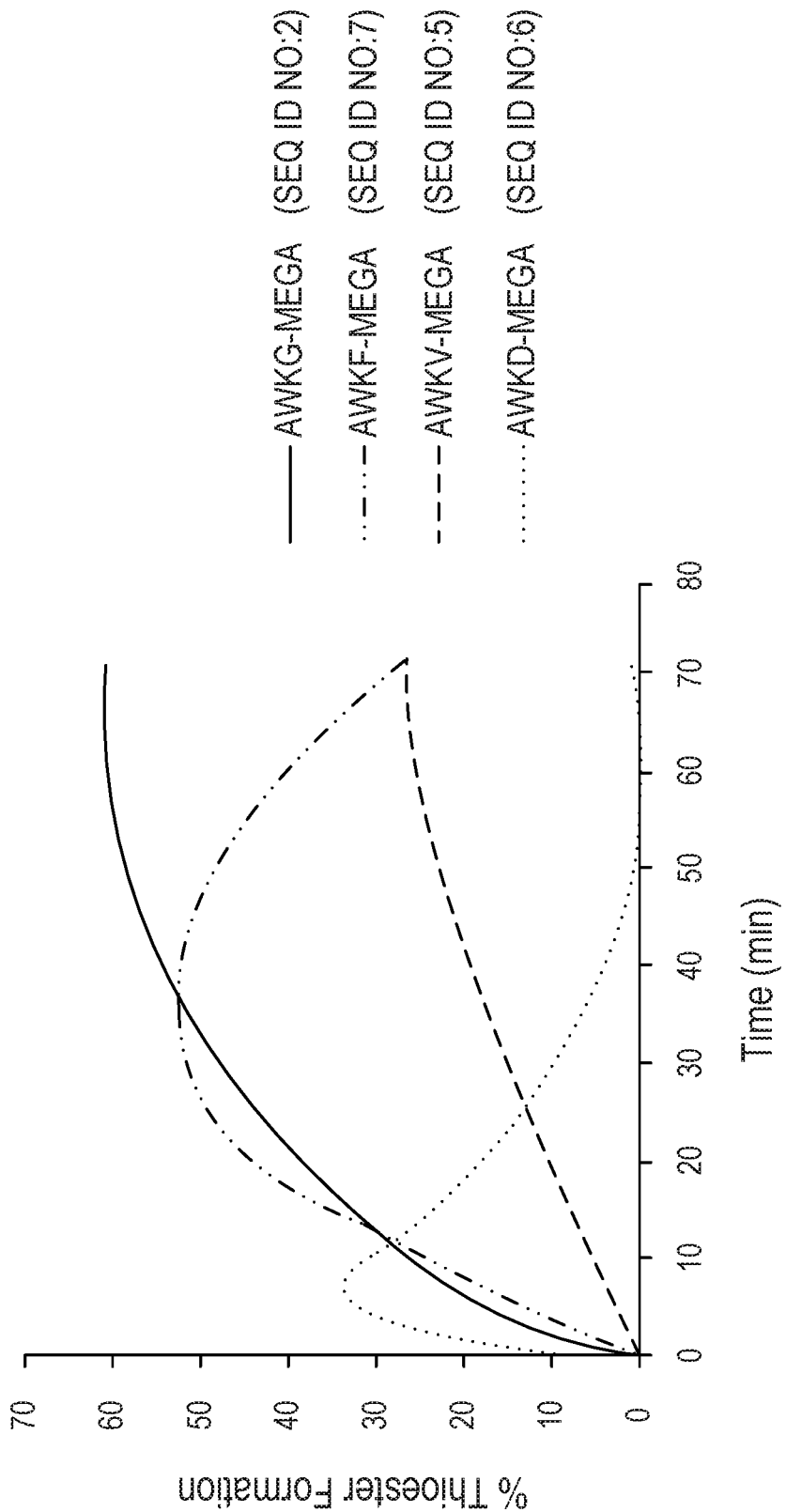
FIG. 11 is a graph depicting a time-course of thioester formation for AWKX-MEGA (SEQ ID NO:1) peptides. Reactions were performed under optimized temperatures at pH 5.6 for each peptide. The final percent thioester formed at each time-point was determined by RP-HPLC peak integration at 280 nm.
Figure 12A:
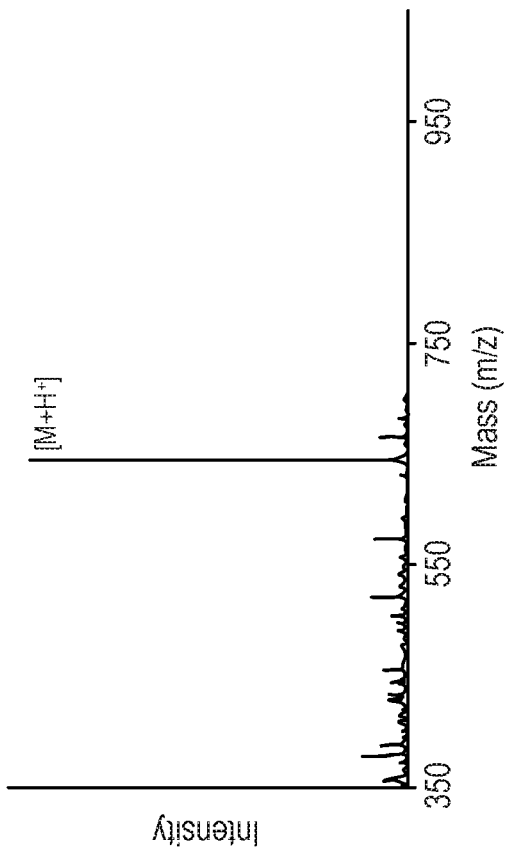
FIG. 12A depicts an AWKD-MEGA (SEQ ID NO:6) thioesterification time-course.
Figure 12B:
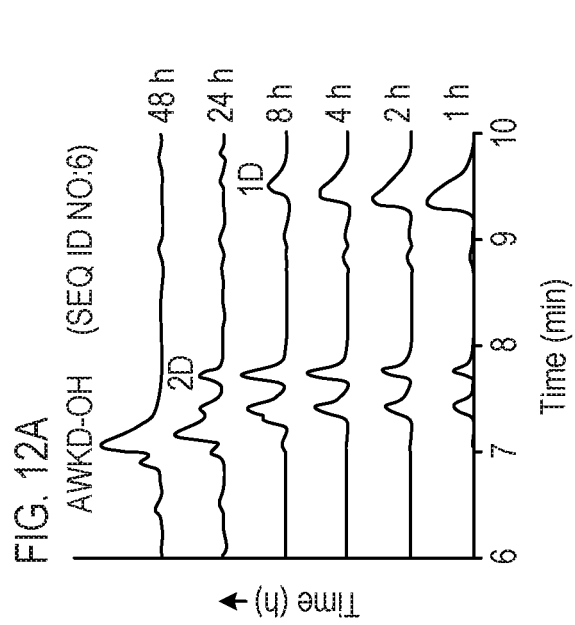
FIG. 12B depicts ESI-MS of AWKD-MES (SEQ ID NO:6) thioester. Calcd. [M+H⁺] 642.7 Da, obsd. 642.3 Da.
Figure 12C:
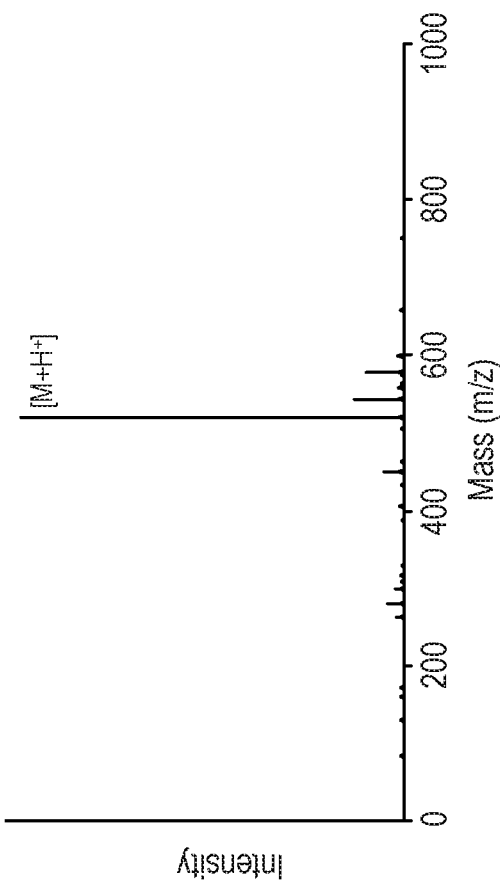
FIG. 12C depicts ESI-MS of AWKD-OH (SEQ ID NO:6) by-product. Calcd. [M+H⁺] 518.5 Da; obsd. 518.4 Da. For FIGS. 12A-12C, 1=AWKD-MEGA (SEQ ID NO:6), 2=AWKD-MES (SEQ ID NO:6) thioester. RP-HPLC performed on C18 analytical column, 10-60% B, 30 minute gradient.
Figure 13A:
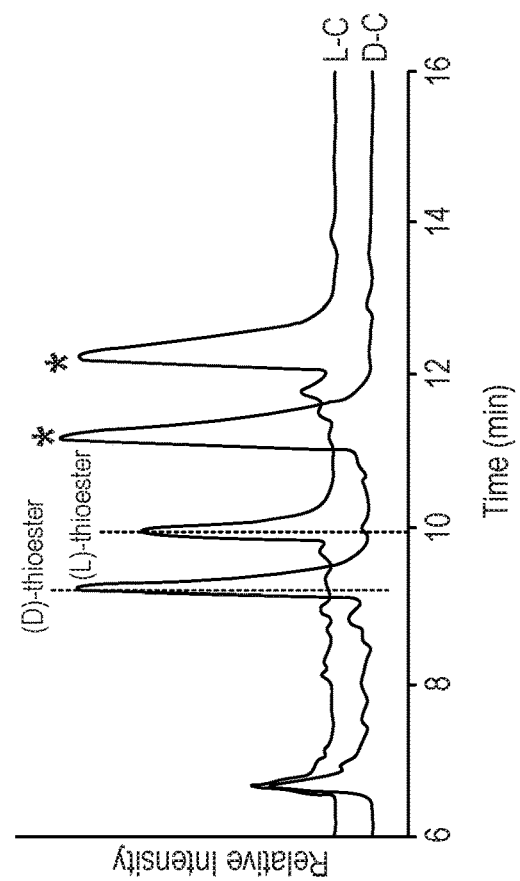
FIG. 13A depicts overlaid C18 analytical RP-HPLC of AWK(D-A)-MES (SEQ ID NO:12) and AWKA-MES (SEQ ID NO:3) thioesters formed at 8 hours. 0.6% and 1.3% epimerization were observed for AWK(D-A)-MEGA (SEQ ID NO:12) and AWKA-MEGA (SEQ ID NO:3), respectively.
Figure 13B:
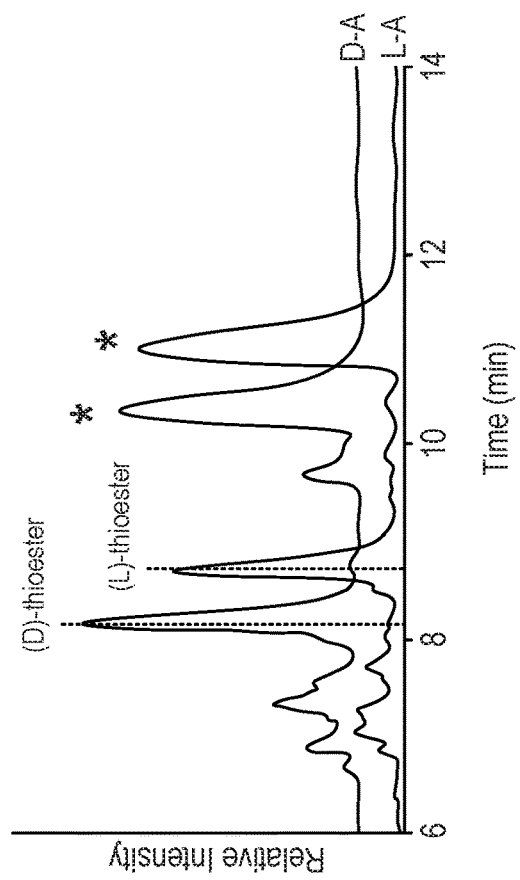
FIG. 13B depicts overlaid C18 analytical RP-HPLC of AWK(D-C)-MES (SEQ ID NO:15) and AWKC-MES (SEQ ID NO:14) thioesters formed at 24 hours; 0.8% and 1.1% epimerization were observed for AWK(D-C)-MEGA (SEQ ID NO:15) and AWKC-MEGA (SEQ ID NO:14), respectively. For FIGS. 13A and 13B, RP-HPLC: 10-60% B, 30 minute gradient. *=AWKX-MEGA (SEQ ID NO:1) starting material.

Although the AWKD-MEGA (SEQ ID NO:6) peptide showed good initial kinetics of thioesterification, a drop in thioester product recovered after >8 hours was observed (see FIG. 11). Without being bound by any one particular theory, MS characterization of the reaction products at 24 hours suggested the formation of a C-terminal aspartic anhydride, followed by its hydrolysis to aspartate (see FIGS. 12A-12C). Accordingly, some C-terminal amino acids with nucleophilic side-chains may cyclize upon incubation at elevated temperatures for extended periods of time. However, a peptide with C-terminal Lys produced the corresponding thioester in good yield (see Table 2, entry 2). The potential for C-terminal epimerization during thioesterification was also addressed. The D-epimers of AWKA-MEGA (SEQ ID NO:3) and AWKC-MEGA (SEQ ID NO:14) were synthesized and converted to their respective thioesters (see Tables 1 and 2 and FIGS. 13A and 13B). Cys was chosen as it can be particularly prone to racemization in its activated form (see Han, Y., et al. J. Org. Chem. 1997, 62, 4307). All diastereomeric thioesters displayed different RP-HPLC retention times upon co-injection, and an average of <1 epimerization was observed throughout the time-course of thioesterification. Thus, the MEGA linker approach leads to minimal epimerization for Ala and Cys, and hence good overall thioesterification yields.

Example 9—Use of MEGA for Longer Sequences

To test the utility of MEGA for longer sequences, the 35-mer peptide p53(1-35)-MEGA (SEQ ID NO:21) was prepared via microwave-assisted automated SPPS on a LIBERTY BLUE™ peptide synthesizer (CEM™ Corporation, Matthews, N.C.) (see FIG. 14A). Initial attempts revealed that 90° C. coupling and deprotection cycles with 20% (v/v) piperidine in DMF led to significant N—O bond cleavage and reduced yields. This issue was addressed by decreasing coupling and deprotection temperatures to 50° C., and employing 5% (w/v) piperazine and 0.1 M HOBt in DMF as a less basic mixture for Fmoc-deprotection. Under these optimized conditions, N—O bond cleavage was completely eliminated from the crude peptide product and pure p53(1-35)-MEGA (SEQ ID NO:21) was obtained in 22% isolated yield (see FIGS. 14B and 14C). The final peptide was subjected to thioesterification and generated the corresponding MESNa thioester in 75% yield (see FIGS. 14D and 14E). The fact that MEGA-linked resin can be compatible with microwave-assisted SPPS may facilitate the synthesis of otherwise challenging sequences in higher yields and purity (see Bacsa, B., et al. Nat. Protoc. 2007, 2, 2222).

Example 10—One-Pot Intermolecular NCL with MEGA

Figure 15:
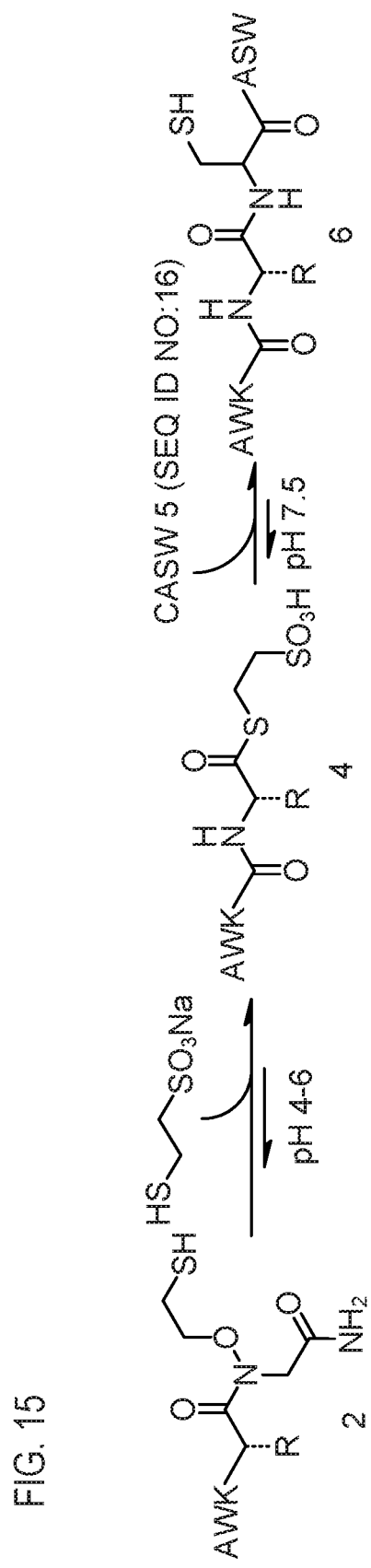
FIG. 15 is a scheme for one-pot NCL of AWKX-MEGA (SEQ ID NO:1) peptides.
Figures 17A, 17B, 17C:
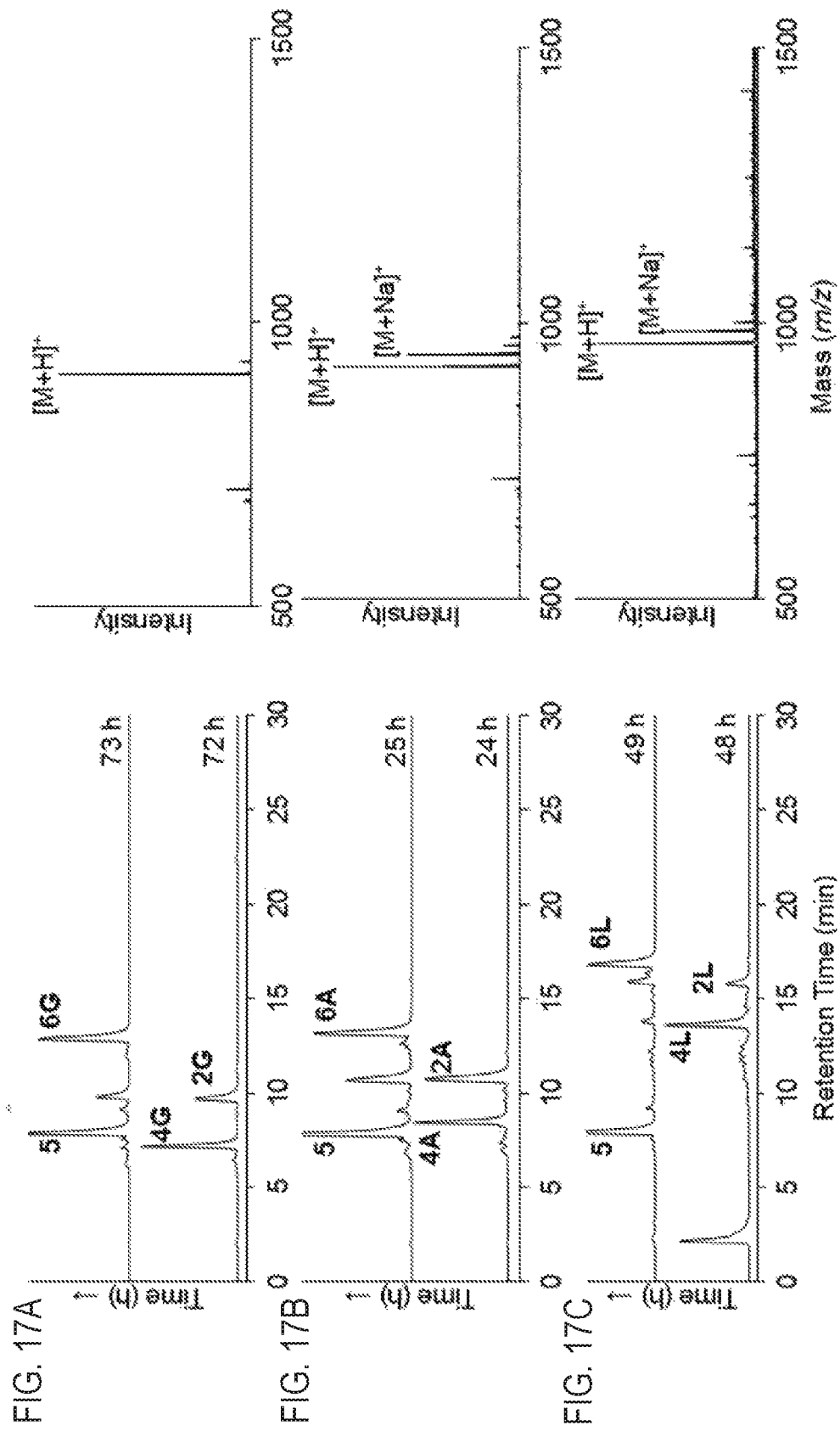
FIG. 17A is a C18 RP-HPLC time-course of NCL for AWKG-MEGA (SEQ ID NO:2) (left) and ESI-MS of isolated AWKGCASW (SEQ ID NO:17) (right). Calcd. [M+H]⁺ 907.6 Da, obsd. 907.9 Da. RP-HPLC: 10-60% CH₃CN in water, 30 minute gradient.
FIG. 17B is a C18 RP-HPLC time-course of NCL for AWKA-MEGA (SEQ ID NO:3) (left) and ESI-MS of isolated AWKACASW (SEQ ID NO:18) (right). Calcd. [M+H]⁺ 921.9 Da, obsd. 921.7 Da. RP-HPLC: 10-60% CH₃CN in water, 30 minute gradient.
FIG. 17C is a C18 RP-HPLC time-course of NCL for AWKL-MEGA (SEQ ID NO:4) (left) and ESI-MS of isolated AWKLCASW (SEQ ID NO:19) (right). Calcd. [M+H]⁺ 963.2 Da, obsd. 963.8 Da. RP-HPLC: 10-60% CH₃CN in water, 30 minute gradient.
Figure 18B:
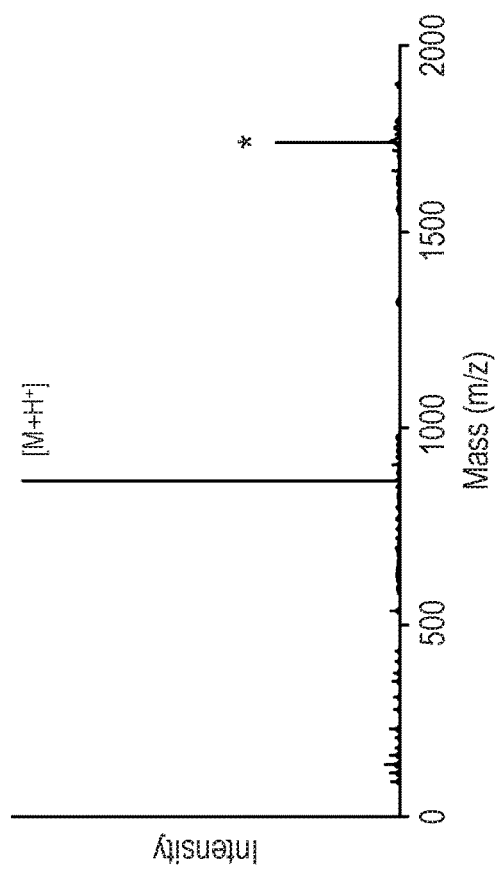
FIG. 18B depicts ESI-MS of purified CASHEW-MEGA (SEQ ID NO:20) peptide. Calcd. [M+H⁺] 864.0 Da, obsd. 864.0 Da. *=Symmetric disulfide of CASHEW-MEGA (SEQ ID NO:20).
Figure 18A:
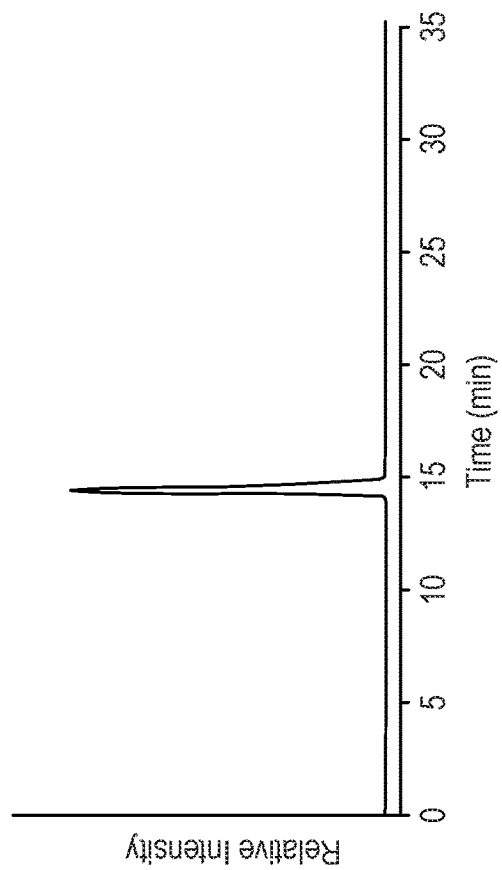
FIG. 18A is a C18 analytical RP-HPLC chromatogram of purified CASHEW-MEGA (SEQ ID NO:20) peptide, 0-73% B, 30 minute gradient.
Figure 19B:
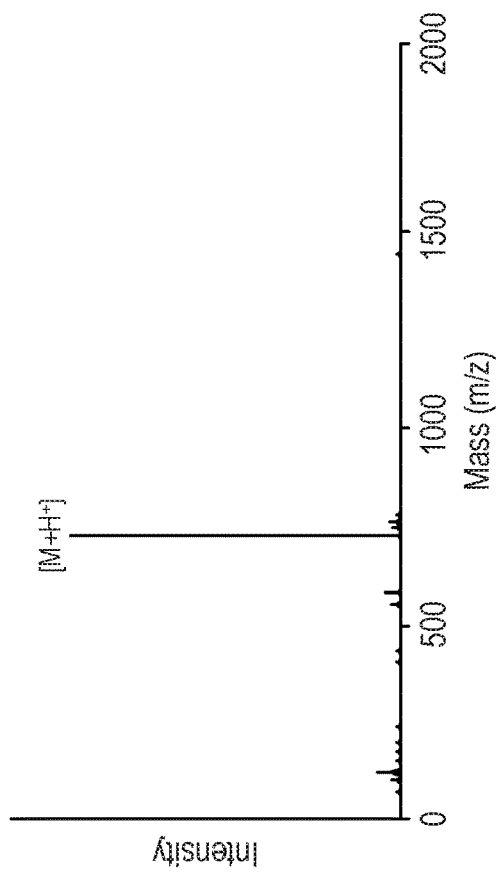
FIG. 19B depicts ESI-MS of purified CRGD(D-F)-MEGA peptide. Calcd. [M+H⁺] 728.8 Da, obsd. 728.7 Da.
Figure 19A:
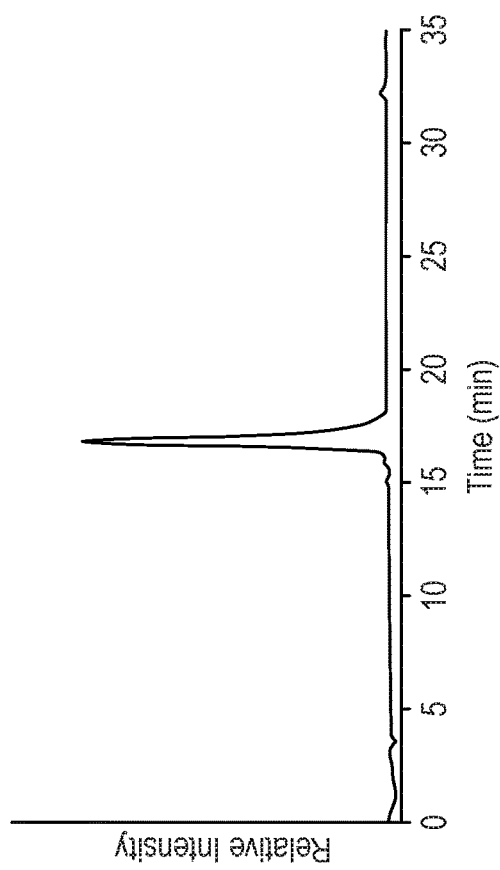
FIG. 19A is a C18 analytical RP-HPLC chromatogram of purified CRGD(D-F)-MEGA peptide, 0-73% B, 30 minute gradient.

With the successful synthesis of thioesters of varying lengths, the scope for one-pot NCL between AWKX-MEGA (SEQ ID NO:1) peptides and an N-terminal Cys-containing peptide, CASW (5) (SEQ ID NO:16) was next investigated (see FIGS. 15, 16A, and 16B). First, AWKX-MEGA (SEQ ID NO:1) thioesterification was undertaken with optimized conditions (see Table 2), followed by the addition of 5 at pH 7.5. NCL proceeded rapidly at room temperature to generate the peptide AWKXCASW (6) (SEQ ID NO:26) in 1 hour with minimal thioester hydrolysis (see FIGS. 17A-17C). The ability to directly use thioesters generated with MEGA in NCL, without intermediate purification, may be particularly attractive for higher overall yields of ligation products.

Example 11—Peptide Cyclization

Figure 20A:
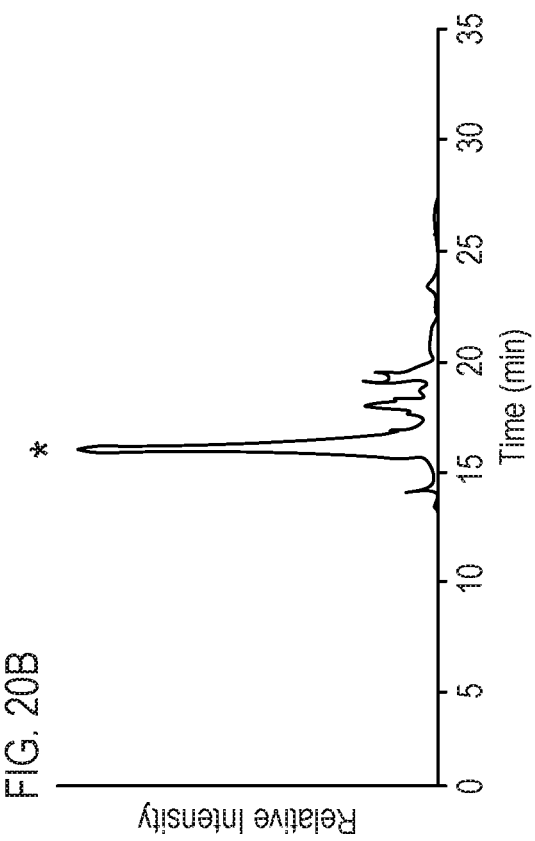
FIG. 20A is an RP-HPLC spectra of crude CRGD(D-F)-MEGA peptide after TFA-cleavage from resin.
Figure 20B:
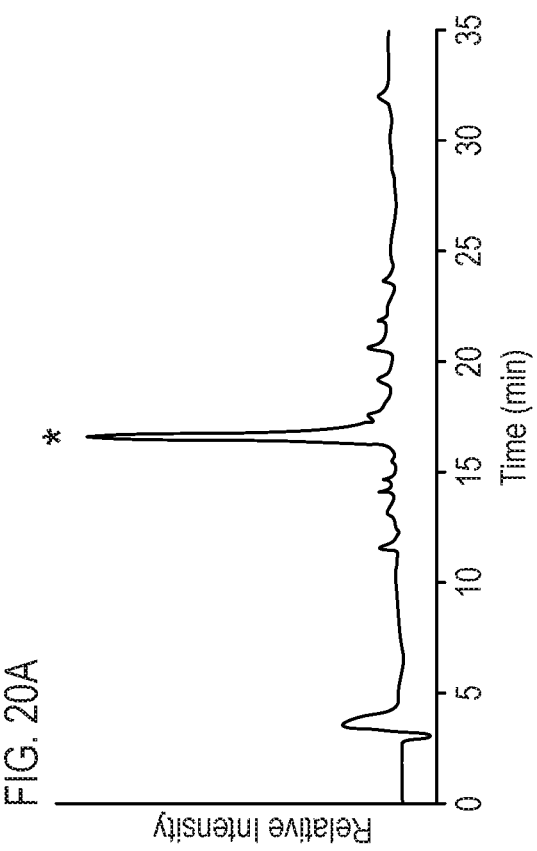
FIG. 20B is an RP-HPLC spectra of crude CASHEW-MEGA (SEQ ID NO:20) peptide after TFA-cleavage from resin. For FIGS. 20A and 20B, RP-HPLC performed on C18 analytical column, 0-73% B, 30 minute gradient. Asterisks indicate the desired product.
Figure 23E:
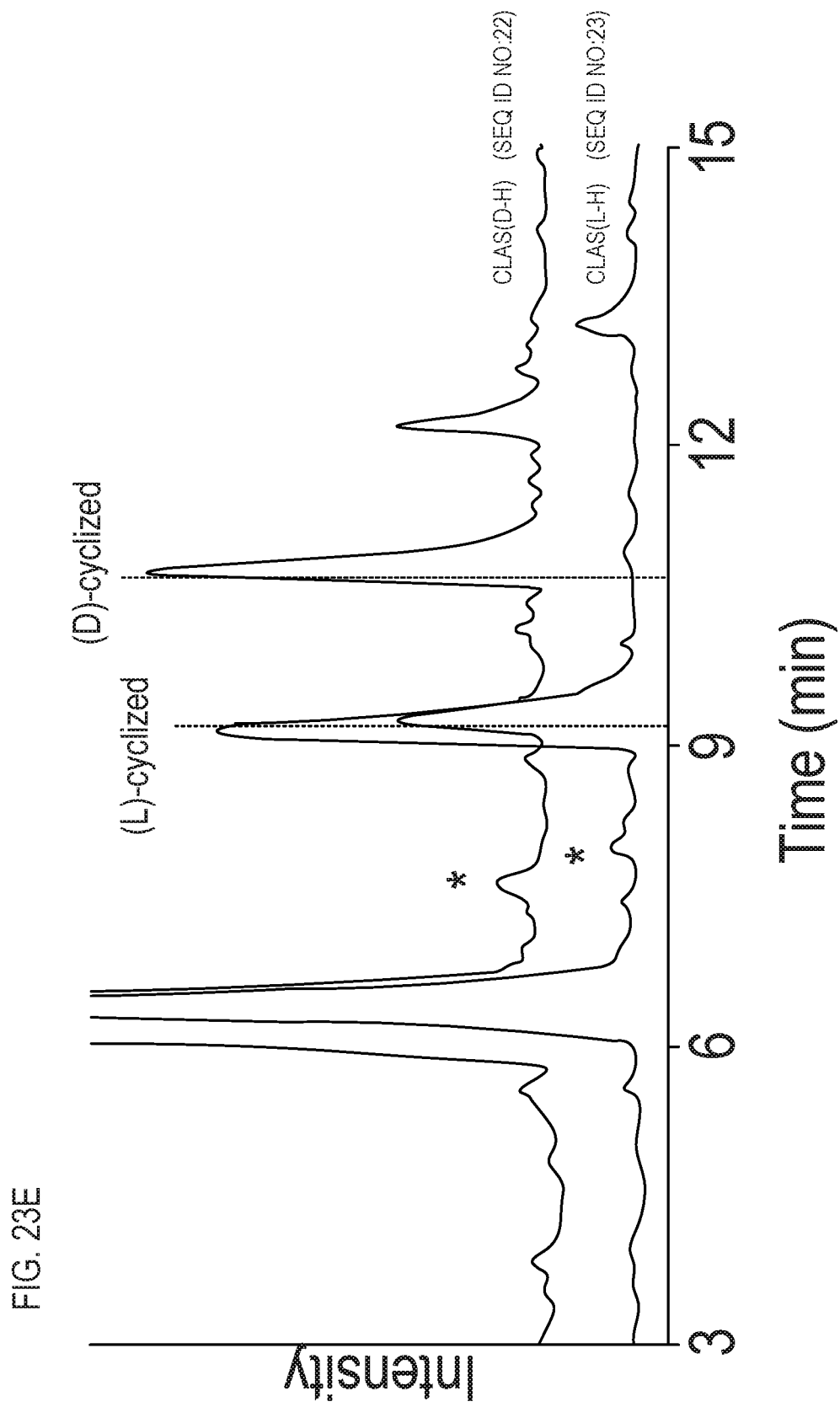
FIG. 23E depicts overlaid C18 analytical RP-HPLC of CLAS(D-H)-MEGA (SEQ ID NO:22) and CLAS(L-H)-MEGA (SEQ ID NO:23) cyclization reactions at 24 hours; 24.8% and 1.8% epimerization were observed for CLAS(D-H)-MEGA (SEQ ID NO:22) and CLAS(L-H)-MEGA (SEQ ID NO:23), respectively. For FIGS. 23A-23E, 1=CLASH-MEGA (SEQ ID NO:24), 2=Cyclized product, *=Unreacted CLASH-MEGA (SEQ ID NO:24). RP-HPLC performed on C18 analytical column, 10-60% B, 30 minute gradient.

Following successful one-pot intermolecular NCL with MEGA as described above, its application for intramolecular NCL to access head-to-tail cyclized peptides was envisioned. Cyclic peptides are useful scaffolds in therapeutic discovery efforts due to their conformational rigidity, which entropically favors enhanced target binding compared to linear peptides. Additionally, the lack of free N- and C-termini in cyclic peptides confers resistance to exopeptidases and enhances membrane permeation (see Wang, C. K., et al. J. Biopolymers 2016, 106, 901). To this end, two short peptides were synthesized, CASHEW-MEGA (SEQ ID NO:20) and CRGD(D-F)-MEGA (see FIGS. 18A-19B). The cyclic form of CRGD(D-F) binds the integrin $\alpha_v\beta_3$ receptor with nanomolar affinity (see Prante, O., et al. Bioconjug. Chem. 2007, 18, 254). Both peptides were prepared by automated SPPS in overall isolated yields of 56% and 45%, respectively (see FIGS. 20A and 20B). The peptides were subjected to one-pot thioesterification and cyclization and both reactions proceeded to completion in <8 hours with no significant side-products detected by HPLC and MS (see FIGS. 21A and 21B). Although the synthesis of cyclic peptides by MEGA utilizes the presence of an N-terminal thiol for ligation, the ability to desulfurize Cys (see Yan, L. Z., et al. J. Am. Chem. Soc. 2001, 123, 526), and other thiol-containing Cys surrogates (see Noisier, A. F. M., et al. Amino Acids Pept. Prot. 2014, 39, 1), post-cyclization can provide facile access to a wide range of cyclic peptides that may not have Cys in their primary sequences Example 12—Assessment of Epimerization During Cyclization The extent of epimerization during peptide cyclization was also assessed. C-terminally activated His residues can be particularly prone to epimerization due to the proximity of the imidazole side-chain to the backbone α-hydrogen (see Jones, J. H., et al. Int. J. Pept. Protein Res. 1980, 15, 301). Therefore two epimeric peptides, CLAS(D-H)-MEGA (SEQ ID NO:22) and CLAS(L-H)-MEGA (SEQ ID NO:23), were synthesized and their degree of epimerization during one-pot cyclization was measured (see FIGS. 22A-22D). The diastereomeric cyclic CLASH (SEQ ID NO:24) peptides were well-resolved by RP-HPLC (see FIGS. 23A-23D) and it was found that CLAS(L-H)-MEGA (SEQ ID NO:23) epimerized <2% after 24 hours (see FIG. 23E).

Example 13—Preparation of Sunflower Trypsin Inhibitor-1

Figure 24A:
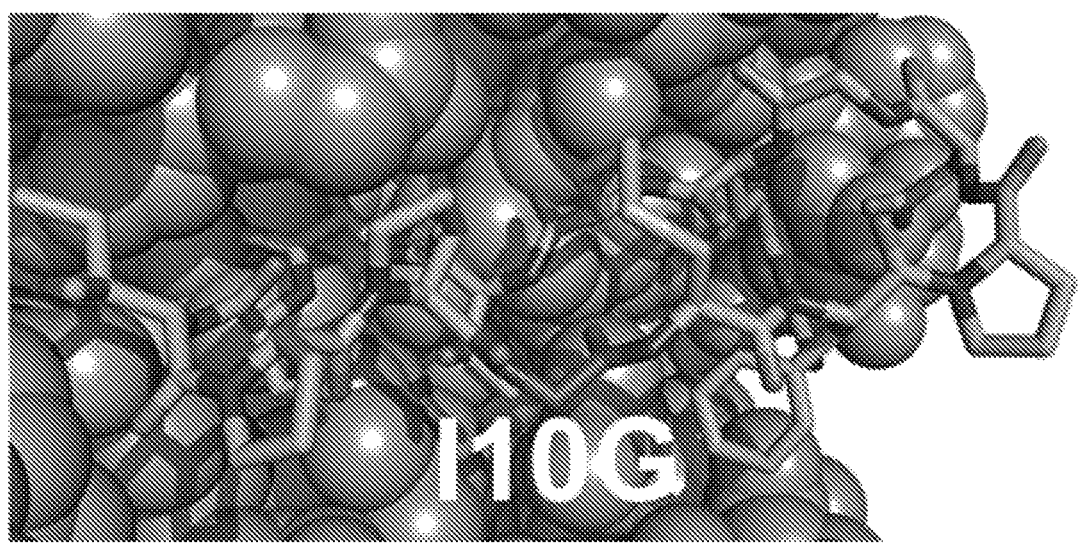
FIG. 24A is a model of SFT-1(I10G) (stick representation) based on the X-ray structure of SFT-1 bound to bovine trypsin (gray spheres). PDB code 1SFI.
Figure 24B:
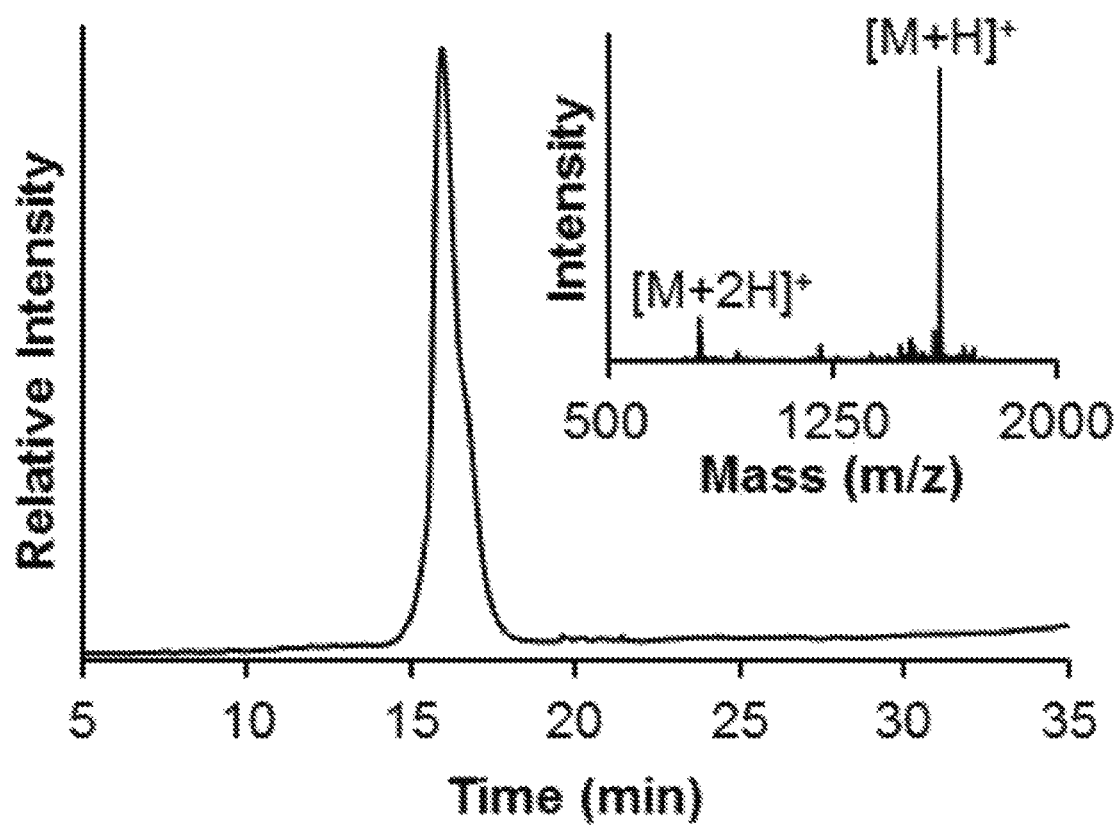
FIG. 24B is a C18 RP-HPLC of SFT-1(I10G)-MEGA (SEQ ID NO:25) peptide. Inset is the ESI-MS of SFT-1 (I10G)-MEGA (SEQ ID NO:25); Calcd. [M+H$^+$] 1,609.9 Da, obsd. 1,609.8±0.2 Da. RP-HPLC: 0-73% CH$_3$CN in water, 30 minute gradient.
Figure 25:
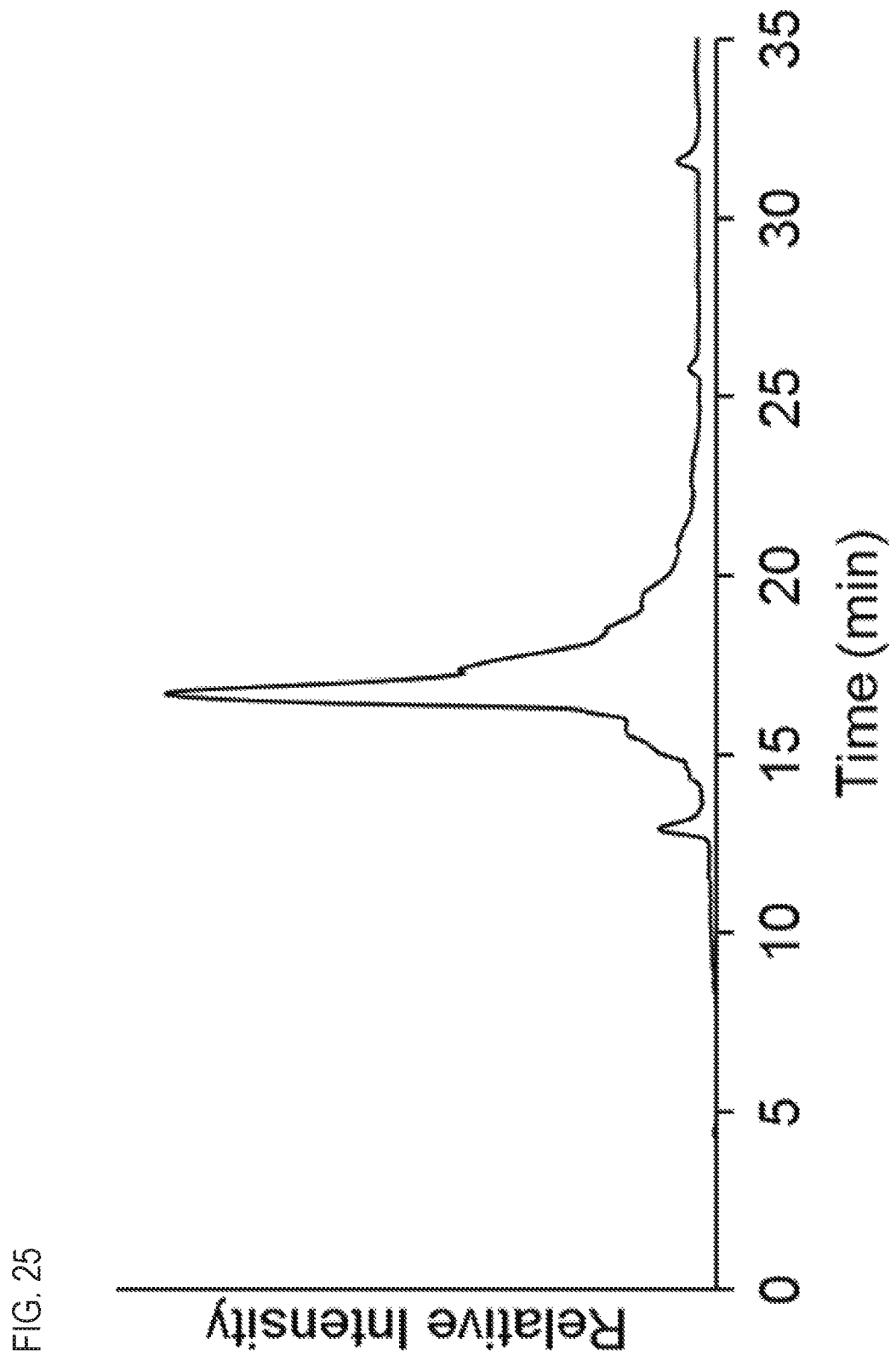
FIG. 25 is an RP-HPLC spectrum of crude SFT-1(I10G)-MEGA (SEQ ID NO:25) peptide after TFA-cleavage from resin. RP-HPLC performed on C18 analytical column, 0-73% B, 30 minute gradient.
Figure 26A:
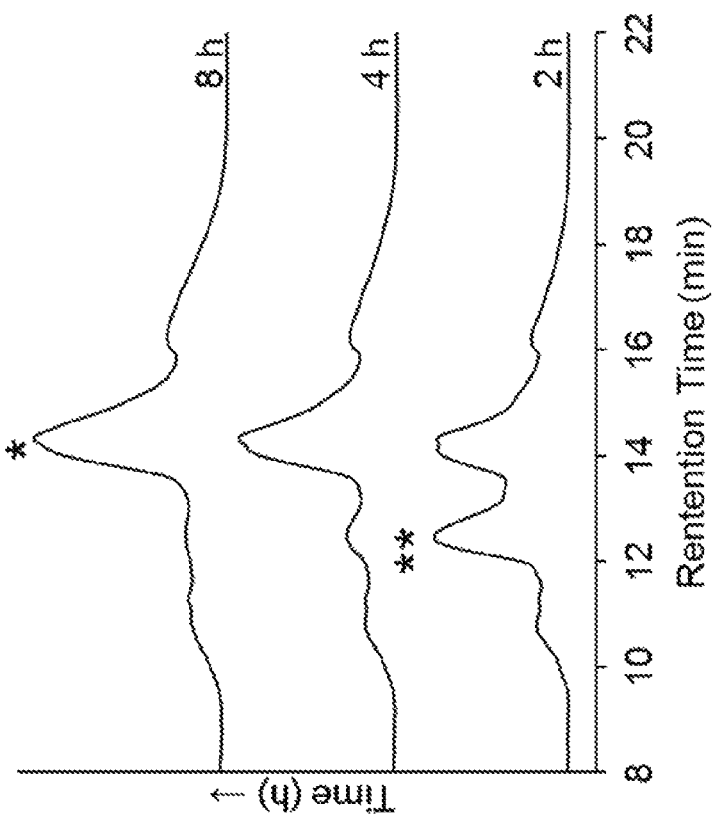

The MEGA strategy was applied toward the Sunflower Trypsin Inhibitor-1 (SFT-1). SFT-1 is a 14-mer cyclic peptide that is structurally constrained by three Pro residues, an extensive hydrogen bond network, and also contains one internal disulfide (see Korsinczky, M. L., et al. J. Curr. Protein Pept. Sci. 2004, 5, 351). SFT-1 is the smallest Bowman-Birk type trypsin inhibitor and analogs of SFT-1 are active against a range of proteases including matriptase and kallikreins (see FIG. 24A). One potent analog of SFT-1, the I10G mutant, was previously obtained using manual peptide synthesis and Boc-chemistry (see Quimbar, P., et al. J. Biol. Chem. 2013, 288, 13885). In order to simplify access to SFT-1(I10G), the linear sequence 14-mer peptide CFP-DGRCTKSIPPG-MEGA (SEQ ID NO:25) was synthesized by automated SPPS (see FIGS. 24B and 25). The purified peptide was incubated in thioesterification buffer for 24 hours at 50° C. to provide the cyclized product in 30% isolated yield after RP-HPLC purification (see FIGS. 26A and 26B). The cyclized peptide was then quantitatively oxidized to the disulfide form by incubation in ammonium bicarbonate buffer overnight (see FIG. 27A). SFT-1 (I10G) was also tested for inhibitory activity against bovine Trypsin by employing the well-characterized substrate N-(α)-benzoyl-L-arginine-4-nitroanilide (BAPNA). Trypsin hydrolyzes BAPNA to release the yellow colored 4-nitroaniline, which is easily detected by its absorbance at 410 nm. Assays were conducted in 96-well plate format with 100 nM Trypsin, 500 µM BAPNA, and varying concentrations of SFT-1 (I10G). Consistent with previous reports, a robust dose-response curve with $IC_{50}=150.2\pm1.1$ nM was observed (see FIG. 27B). Thus, the Fmoc-compatible and automated approach disclosed herein simplified access to a bioactive cyclic peptide.

Unless otherwise indicated, for the examples provided herein, Rink-amide resin (0.30-60 mmol/g substitution) was purchased from CHEM-IMPEX™ (Wood Dale, Ill.). Standard Fmoc-L-amino acids were purchased from AGTC BIOPRODUCTS™ (Wilmington, Mass.) or ANASPEC™ (Fremont, Calif.). All other chemical reagents were purchased from SIGMA-ALDRICH® Chemical Company (St. Louis, Mo.) or FISHER SCIENTIFIC™ (Pittsburgh, Pa.). SPPS was performed manually or on a LIBERTY BLUE™ Automated Microwave Peptide Synthesizer (CEM™ Corporation, Matthews, N.C.) (see Coin, I., et al. Nat. Protoc. 2007, 2, 3247). Analytical reversed-phase HPLC (RP-HPLC) was performed on a VARIAN™ (Palo Alto, Calif.) PROSTAR™ HPLC with a GRACE-VYDAC™ (Deerfield, Ill.) C18 column (5 micron, 150×4.6 mm) employing 0.1% TFA in water (A) and 90% $CH_3CN$, 0.1% TFA in water (B) as the mobile phases. Typical analytical gradients were 0-73% B over 30 minutes at a flow rate of 1 mL/min. Preparative scale purifications were conducted on a GRACE-VYDAC™ C18 column (10 micron, 250×22 mm) at a flow rate of 9 mL/min. Semi-preparative scale purifications were conducted on a GRACE-VYDAC™ C18 column (5 micron, 250×10 mm) at a flow rate of 3.5 mL/min. Mass spectrometric analysis was conducted on a BRUKER™ (Billerica, Mass.) ESQUIRE™ ESI-MS instrument.

Example 14—Synthesis of Trityl-Protected Auxiliary

A trityl-protected auxiliary was synthesized as indicated in the scheme below.

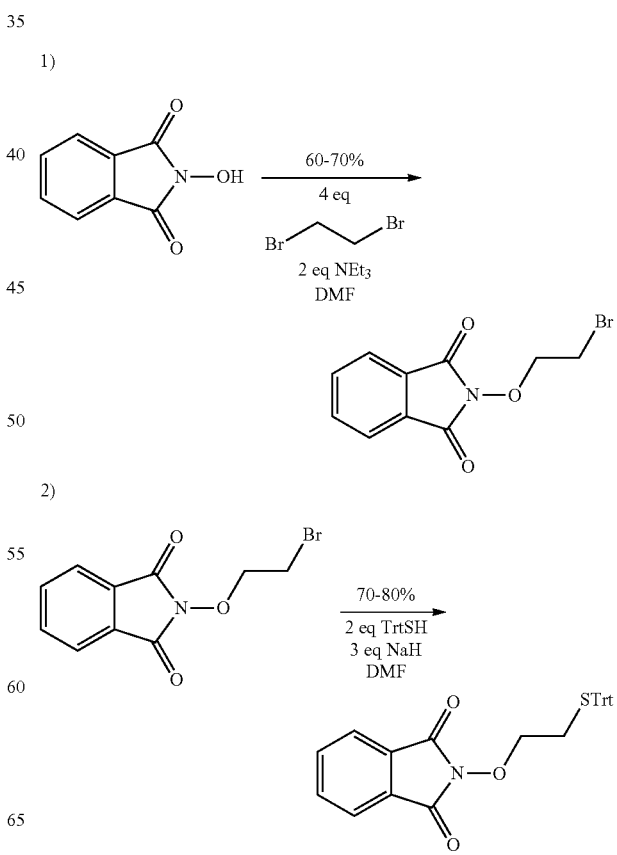

3)

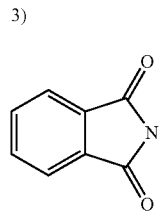 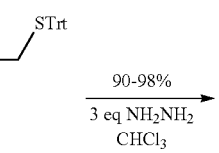

$$\xrightarrow[\text{CHCl}_3]{\text{3 eq NH}_2\text{NH}_2} \text{90-98\%}$$

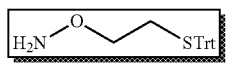

Purification at step 1 of the scheme included recrystallization from 95% ethanol. Purification at step 2 of the scheme included silica gel chromatography, 90:10 hexane:ethyl acetate, 60:40 hexane:ethyl acetate. Purification at step 3 of the scheme included aqueous extraction and concentration.

Example 15—Synthesis of MEGA Resin

MEGA resin was synthesized as depicted in FIG. 28A. A typical first amino acid coupling as used herein is depicted in FIG. 28B.

Example 16—Synthesis of p53(1-35)-MEGA p53(1-35)-MEGA (SEQ ID NO:21) was synthesized using Rink amide resin from CHEM-IMPEX™ (Wood Dale, Ill.). Automated SPPS was conducted under the following conditions: single 10 minute 50° C. cycles, DIC/Oxyma, no microwave deprotection cycles, and 5% piperazine/0.1 M HOBt (see FIGS. 29A-29D).

First amino acid (Leu) loading was ~75% based on a quantitative Kaiser test. With reference to FIG. 30A, automated SPPS was conducted under the following conditions: single 10 minute 50° C. coupling cycles, DIC/Oxyma, no microwave deprotection cycles, and 5% piperazine/0.1 M HOBt.

With reference to FIG. 30B, automated SPPS was conducted under the following conditions: single 10 minute 50° C. coupling cycles, DIC/Oxyma, 50° C. deprotection cycles, and 5% piperazine/0.1 M HOBt.

p53(1-35)-MEGA (SEQ ID NO:21) thioesterification was also assessed. With reference to FIGS. 31A and 31B, a 75% yield was observed based on RP-HPLC peak integration at 280 nm.

Example 17—Synthesis of SFT-1(I10G)-MEGA

SFT-1(I10G)-MEGA (SEQ ID NO:25) was synthesized using Rink amide resin from CHEM-IMPEX™ (Wood Dale, Ill.). Automated SPPS was conducted under the following conditions: single 10 minute 50° C. cycles, DIC/Oxyma, no microwave deprotection cycles, and 20% piperadine (see FIGS. 32A-32D) (see Macmillan, D., et al. Tetrahedron, 2014, 70, 7675-80).

Example 18—Synthesis of SFT-1(I10G)-MEGA on Rink Amide PROTIDE® (LL) Resin

Automated first amino acid (Gly) coupling was conducted under the following conditions: 3×10 minutes 70° C. coupling cycle and HATU/DIEA (not optimized). 50% amino acid loading was observed based on a quantitative Kaiser test. Automated SPPS was conducted under the following conditions: single 10 minute 50° C. coupling cycles, DIC/Oxyma, 50° C. deprotection cycles, and 5% piperazine/0.1 M HOBt (see FIG. 33). FIGS. 34A and 34B depict a SFT-1(I10G)-MEGA (SEQ ID NO:25) cyclization time-course. It is noted that there were two Cys residues.

Example 19—Synthesis of CRGD(D)-F-MEGA on Rink Amide PROTIDE® (LL) Resin

Cyclic CRGD(D)-F is a commercially available integrin binding peptide (ANASPEC™, Fremont, Calif.). A typical first amino acid coupling procedure was used. Automated SPPS was conducted under the following conditions: single 10 minute 50° C. coupling cycles, DIC/Oxyma, 50° C. deprotection cycles, and 5% piperazine/0.1 M HOBt (see FIGS. 35A-35D). FIGS. 36A and 36B depict a CRGD(D)-F cyclization time-course.

Certain embodiments of this disclosure are described herein, including the best mode known to the inventors for carrying out the disclosure. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications is individually incorporated herein by reference in its entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

It will be apparent to those having skill in the art that many changes may be made to the details of the above-described embodiments without departing from the underlying principles of the disclosure. The scope of the present invention should, therefore, be determined only by the following claims.

The invention claimed is:

1. A solid support for use in solid-phase peptide synthesis, the solid support comprising:
   a resin coupled to a linker,
   wherein the linker is at least one of an N-mercaptoethoxyglycine, an N-mercaptopropoxyglycine, and an N-mercaptobutoxyglycine.

2. The solid support of claim 1, wherein the resin is substantially insoluble.

3. The solid support of claim 1, wherein the linker is coupled to a protecting group, and wherein the protecting group is selected from at least one of an ortho-nitrobenzyl group, a trityl group, an acetamidomethyl group, an alkyl thiol group, and an aromatic thiol group.

4. The solid support of claim 3, wherein the protecting group is coupled to the sulfur molecule of the linker.

5. The solid support of claim 1, wherein the resin is selected from at least one of a Rink amide resin, a PAL resin, a PAM resin, a BHA resin, an MBHA resin, a Wang resin, a PHB resin, an HMPA resin, an HMPB resin, an aminomethyl resin, a polystyrene (PS) resin, and a polyethylene glycol-polystyrene (PEG-PS) resin.

6. A kit for solid-phase peptide synthesis, the kit comprising:
   a solid support comprising a resin coupled to a linker, wherein the linker is at least one of an N-mercaptoethoxyglycine, an N-mercaptopropoxyglycine, and an N-mercaptobutoxyglycine;
   a solution comprising a thiol, wherein the pH of the solution is between about 4 and about 7;
   a first plurality of protected amino acids, wherein the protected amino acids of the first plurality of protected amino acids are coupled to a first protecting moiety; and
   a wash buffer.

7. The kit of claim 6, wherein the thiol is at least one of a mercaptoethanesulfonate, an ethanethiol, a glutathione, and an aliphatic thiol.

8. The kit of claim 6, wherein the thiol has a pKa between about 7 and about 10 and a vapor pressure of between about 0 mmHg and about 550 mmHg at 25° C.

9. The kit of claim 6, wherein the first protecting moiety is at least one of a tert-butoxycarbonyl moiety, a 9-fluorenylmethyloxycarbonyl moiety, a trityl moiety, an o-nitrobenzyl moiety, a 2,2,4,6,7-pentamethyldihydrobenzofuran-5-sulfonyl moiety, and a 4-methyltrityl moiety.

10. The kit of claim 6, wherein the pH of the solution is between about 4 and about 6.

11. The kit of claim 6, further comprising:
a second plurality of protected amino acids, wherein the protected amino acids of the second plurality of protected amino acids are coupled to a second protecting moiety, and wherein the first protecting moiety is different from the second protecting moiety.

12. The kit of claim 6, wherein the resin is substantially insoluble.

13. The kit of claim 6, wherein the linker is coupled to a protecting group, and wherein the protecting group is selected from at least one of an ortho-nitrobenzyl group, a trityl group, an acetamidomethyl group, an alkyl thiol group, and an aromatic thiol group.

14. The kit of claim 13, wherein the protecting group is coupled to the sulfur atom of the linker.

15. The kit of claim 6, wherein the resin is selected from at least one of a Rink amide resin, a PAL resin, a PAM resin, a BHA resin, an MBHA resin, a Wang resin, a PHB resin, an HMPA resin, an HMPB resin, an aminomethyl resin, a polystyrene (PS) resin, and a polyethylene glycol-polystyrene (PEG-PS) resin.

16. The kit of claim 6, further comprising instructions for solid-phase peptide synthesis, the instructions comprising the steps of:
introducing the solution to the solid support such that a plurality of thioesters are generated on the solid support; and
introducing the first plurality of protected amino acids to the plurality of thioesters such that a first portion of the first plurality of protected amino acids is coupled to the solid support.

17. The kit of claim 16, wherein the instructions further comprise the steps of:
introducing the wash buffer to the solid support to remove a second portion of the first plurality of amino acids that are not coupled to the solid support;
introducing a de-protecting reagent to the solid support to remove a portion of the first protecting moieties from the first portion of the first plurality of protected amino acids to generate a first plurality of de-protected amino acids; and
introducing the second plurality of protected amino acids to the solid support such that a portion of the second plurality of protected amino acids is coupled to a portion of the first plurality of de-protected amino acids.

18. A method of solid-phase peptide synthesis, the method comprising:
providing a solid support comprising a resin coupled to a protected linker, wherein the protected linker is selected from at least one of a protected N-mercaptoethoxyglycine, a protected N-mercaptopropoxyglycine, and a protected N-mercaptobutoxyglycine;
introducing a solution having a pH between about 4 and about 7 to the solid support to generate a plurality of thioesters on the solid support, wherein the solution comprises a thiol;
introducing a first plurality of protected amino acids to the solid support to couple a first portion of the first plurality of protected amino acids to the solid support, wherein the protected amino acids of the first plurality of protected amino acids are coupled to a first protecting moiety;
introducing a wash buffer to the solid support to remove a second portion of the first plurality of protected amino acids that are not coupled to the solid support;
introducing a de-protecting reagent to the first portion of the first plurality of protected amino acids to remove a portion of the first protecting moieties from a portion of the first portion of the first plurality of protected amino acids to generate a first plurality of de-protected amino acids; and
introducing a second plurality of protected amino acids to the solid support to couple a portion of the second plurality of protected amino acids to a portion of the first plurality of de-protected amino acids.

19. The method of claim 18, wherein the thiol is at least one of a mercaptoethanesulfonate, an ethanethiol, a glutathione, and an aliphatic thiol.

20. The method of claim 18, wherein the pH of the solution is between about 4 and about 6, and wherein the temperature of the solution is between about 25° C. and about 80° C.

* * * * *